(12) United States Patent
Davis

(10) Patent No.: US 10,786,497 B2
(45) Date of Patent: Sep. 29, 2020

(54) DISCRETE PEG CONSTRUCTS

(71) Applicant: EquIP, LLC, Plain City, OH (US)

(72) Inventor: Paul D. Davis, Dublin, OH (US)

(73) Assignee: EquIP, LLC, Plain City, OH (US)

( * ) Notice: Subject to any disclaimer, the term of this patent is extended or adjusted under 35 U.S.C. 154(b) by 0 days.

(21) Appl. No.: 14/461,155

(22) Filed: Aug. 15, 2014

(65) Prior Publication Data
US 2015/0065711 A1   Mar. 5, 2015

Related U.S. Application Data

(60) Provisional application No. 61/866,584, filed on Aug. 16, 2013.

(51) Int. Cl.
A61K 47/60    (2017.01)
A61K 49/00    (2006.01)
A61K 31/496   (2006.01)
A61K 51/04    (2006.01)

(52) U.S. Cl.
CPC ............ A61K 31/496 (2013.01); A61K 47/60 (2017.08); A61K 49/0043 (2013.01); A61K 49/0054 (2013.01); A61K 51/0482 (2013.01); Y02A 50/395 (2018.01)

(58) Field of Classification Search
CPC .... C07C 271/00; C08G 61/12; C08G 63/664; C08G 65/48; A61K 38/00
See application file for complete search history.

(56) References Cited

FOREIGN PATENT DOCUMENTS

| WO | WO 2007140282 A1 | * | 12/2007 | ....... A61K 47/48215 |
| WO | WO 2008034120 A2 | * | 3/2008 | ....... A61K 47/48215 |

OTHER PUBLICATIONS

Quanta Biodesign Limited, dPEG, Quanta Biodesign Limited, Dec. 30, 2011.*

* cited by examiner

Primary Examiner — James H Alstrum-Acevedo
Assistant Examiner — Kaipeen E Yang
(74) Attorney, Agent, or Firm — Mueller Law, LLC; Jerry K. Mueller, Jr.

(57) ABSTRACT

Disclosed are linear discrete PEG constructs, which can be created and produced in a precise and reproducible way. Key to being able to do these things, where x in the discrete $PEG_x$ can vary from about 2 to about 64, is that the processes used to make each linear portion is controlled to give essentially one oligomer/one compound. Having a variable length linear discrete PEG construct that is (a) primarily an linear discrete PEG construct with diagnostic or therapeutic groups attached along a chain of attachment cores, which is attached to a preferential locator; (b) is an m-discrete PEG as the terminal construct on the linear portion, and "hidden"; (c or linear discrete PEG with a terminus group that can be either negatively or positively charged, or neutral; and any of the discrete PEG portions can be designed to be cleaved after entering the cell.

13 Claims, 1 Drawing Sheet

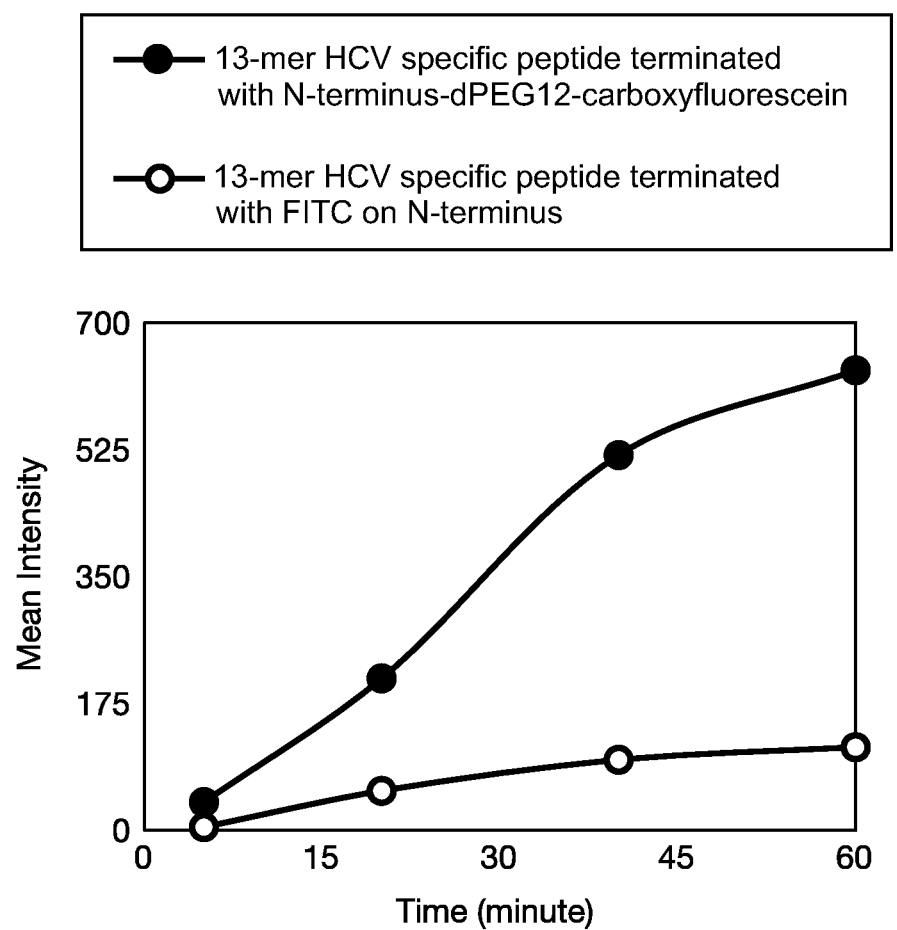

DISCRETE PEG CONSTRUCTS

CROSS-REFERENCE TO RELATED APPLICATIONS

This application claims benefit of U.S. provisional 61/866,584, filed Aug. 16, 2013.

STATEMENT REGARDING FEDERALLY SPONSORED RESEARCH

None.

FIELD OF DISCLOSURE

The present disclosure sets forth substantially pure linear multifunctional based discrete polyethylene glycol construct compositions (dPEG® reagents, a registered trademark of Quanta BioDesign, Ltd., Plain City, Ohio) that can be attached to a large range of useful compounds, primarily of therapeutic or diagnostic significance, in order to significantly effect and control the biodistribution and pharmacokinetics of the useful compounds. These compositions can also be made to attach "A" (biologically active groups) in multiples or in combinations in order to control the total avidity of "A." These compositions can be made as part of dPEG containing templates to enhance the functionality and overall utility of the compositions, e.g., by incorporating both diagnostic and therapeutic functionality. Disclosed also are methods for preparation of the linear multifunctional construct intermediates that can be used to attach other compounds, like toxins or other drugs, to effect a certain action in the body, as well as the compositions themselves, or along chains of AC's as previously disclosed.

As used herein, "dPEG" (and discrete PEG or discrete poly(ethylene) glycol) means a specific and single defined number of ethylene oxide units in a linear construct, e.g., a $dPEG_8$ is an ethylene oxide chain that contains precisely and only 8 ethylene oxide units, in a purity of at least about 90% or can be readily purified to yield such purity. As use herein, "single compound (single molecule compound)" means a compound that is not a mixture, one that is made from chemical procedures (as defined in U.S. Pat. Nos. 7,888,536 and 8,637,711, to make the single product the procedure targets to make. This term is used in contrast to "a polymeric or polydisperse mixture," which is the result of a polymer reaction, and is the case in all of the conventional polymeric PEGylation technology (PEGs) referenced herein. The absolute purity of the dPEG compound is defined further in terms of the particular processes used to produce or purity said compositions to the necessary state as defined by the application.

The advantages of using the discrete PEG construct(s) generally over the conventional polymeric as disclosed/discussed in the "Background" section of Davis, U.S. Patent Publication No. US 2013/0052130 apply to this disclosure.

BACKGROUND

The present disclosure relates to discrete polyethylene glycol (PEG) molecules and more particularly to linear multifunctional based discrete PEG constructs, either alone or used separately on the various preferentially locating carriers or base core constructs.

Many potentially valuable concepts for designing constructs into biological systems have never come to fruition, since most of the available and flexible chemical infrastructures are not extant. That is, such constructs have one or more issues related to being biologically incompatible. Much of the conventional chemistry used, which has potential to add value in that if the chemistry is "conventional", like many therapeutics or diagnostics, creates or exacerbates issues, such as, for example, immunogenicity, hydrophobicity with concomitant solubility and aggregation, are polymeric, creating characterization and reproducibility issues, and the like. Or much of that natural chemistry can simply be too complex, or still have limited design options, e.g., carbohydrates.

As such, it would be a huge benefit in many applications to have nearly complete or completely compatible physical and non-physiological properties with the variation of sizes and functionality to make complex, integrated, and previously unavailable chemical construct end points. The discrete PEG based constructs disclosed herein constitute a significant step in this direction in a vast range of applications and biological, chemical and nanotechnology cores, foundations, or bases. The ability to process and manufacture each base multifunctional linear discrete PEG portion of the overall discrete PEG construct or constructs, as a single compound and in very high oligomeric purity, enables this breadth of highly enabling constructs. The nature of using the linear discrete PEG constructs and with various biological components (as preferential locators), singularly or in multiple or array formats, alone or in combination, alone as biologics or in combination with various nanoparticle constructs of various sizes, gives expected, but unique given the dPEG infrastructure, and many unexpected results in controlling their use to advance the paradigm of designing diagnostic and therapeutic agents to work closer and closer to ideal, where the only action is at the site or location of indication, in vivo or in vitro. Also by adding the apparent size/hydrodynamic volume into the construct via the dPEG will allow for additional advantages in the design of the biologics, e.g., in going from a larger protein, even an antibody or fragment, to a single or array for peptides, the same or different.

In previous disclosures, we have shown and taught how to make linear and branched discrete PEG constructs and disclosed a large range of applications of the branched discrete PEG constructs. These PEG constructs are all included as options in considering the new linear multifunctional based discrete PEG constructs disclosed herein, as well as novel linear/branched combinations, either alone or used separately on the various preferentially locating carriers or base core constructs. References: U.S. Pat. Nos. 7,888,536 and 8,637,711 and U.S. Patent Publication No. US 2013/0052130.

BRIEF SUMMARY

Broadly disclosed are general and "substantially pure" dPEG constructs useful in attaching to a variety of biologically active groups, for example, preferential locators, as well as biologics like enzymes, for use in diagnostics, e.g. imaging, therapeutics, theranostics, and moieties specific for other applications. In its simplest intermediate state, the disclosed dPEG construct is terminated at one end by a chemically reactive moiety, "A", a group that is reactive with a biologic material that creates "A", which is a biologically reactive group, connected through ∼∼∼ to an attachment core (AC) which has attached to it a dPEG-containing chain, indicated by the solid line, ——, having terminal groups, which can be charged, non-reactive or reactable moieties and containing between about 2 and 64 dPEG residues. Also from the attachment core (AC), connected through another ⁓ is attached G, which is a chemical reactable group through which is attached a diagnostic or therapeutic agent. Any chemically reactive or reactable group on the ends may or may not be the same; generally they are different. Connecting these elements is, ⁓, a hydrocarbon chain (aliphatic/alkyl, aromatic/aryl, or aliphatic-aromatic alkyl-aryl) containing a dPEG residue and optionally substituted with O, N, S, Si, Se or P, and optionally having side chains, which may or may not also contain dPEG residues. Optionally the chain can be cleavable. Optionally, there can be more than one attachment core adjacent to the first, attached through a ⁓, which can be the same or different. These side chains are incorporated through specific attachment cores, that can be the same or different.

In one final product form, the chemically reactive moiety has been directly or indirectly attached to a biologically active group—that is, a group that performs a desired function/interaction in vivo, whether as a preferential locator (e.g., an antibody or antibody fragment), a nanoparticle, an enzyme, or other substance. More than one kind of biologically active group could be carried by the disclosed dPEG constructs as part of "A" giving multimeric "A" or bis- or higher heterospecificity (Ref. Davis, U.S. Pub. No. 20130052130, paragraphs (0209)-(0230)). Optionally more than one disclosed dPEG construct is attachable to one biologically active group, and this can occur randomly, yet characterizable or site specifically through design of the biologic.

Such disclosed dPEG constructs generally can be represented by the following:

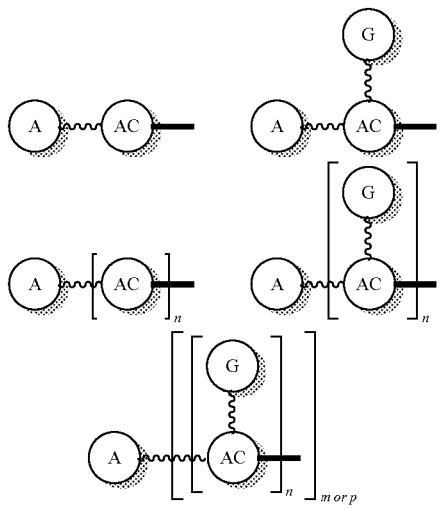

where, A is a chemically reactable group (a group that is reactive or can be made reactive, such as a chemically reactive moiety or a chemically reactive moiety with a protective group); the wavy line, ⁓, as a hydrocarbon chain containing a dPEG residue and optionally substituted with O, N, S, Si, Se or P, and optionally having side chains, which may or may not also contain dPEG residues; and ⎯ or ⁓ as part of

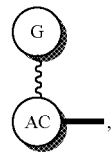

are dPEG-containing chains having terminal reactive or non-reactive groups or functionality. AC is a multifunctional attachment core, often based on a multifunction natural or non-natural amino acid.

One product formed from such intermediate also can be represented by

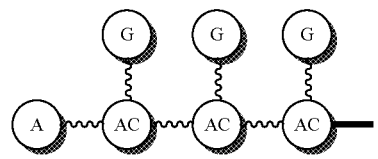

wherein, "A" is now a biologically active group—that is, a group that performs a desired function/interaction in vivo, whether as a preferential locator (e.g., an antibody, fragment, peptide, aptamer, etc.), a nanoparticle, an enzyme, lectin, or other substance of diagnostic or therapeutic significance, e.g., where "A" can also be randomly labeled with a detectable probe, e.g., a radionuclide on the preferential locator.

Disclosed, then are substantially pure compounds represented by:

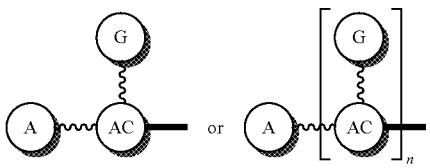

In such structures, A is a biologically active group or a chemically reactive or reactable moiety; the wavy line, ⁓, is a linear discrete polyethylene glycol chain containing between about 4 and 48 discrete ethylene oxide residues optionally substituted with N, S, Si, Se, or P, aryl groups, or alkyl groups; and having chemically reactive or reactable end groups that are independently reactable.

Such substantially pure compounds also can be represented by:

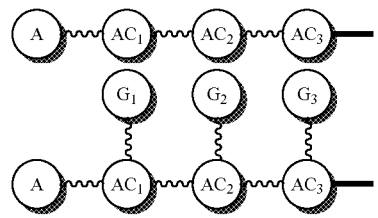

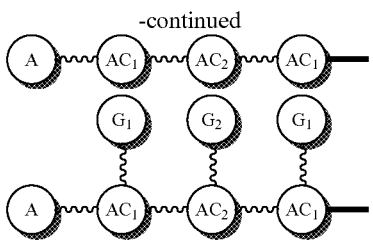

These disclosed compounds are particularly useful for delivering diagnostic and therapeutic agents alone or together in stable and optionally with multiple loading options that take specific advantages of the substantially pure nature of the dPEG and the properties of the linear dPEG itself in in vitro and in vivo applications.

These disclosed compounds also are useful in externally imaging an antibody, antibody fragment, or a peptide attached to an externally imagable radiolabel, where an imaginable radiolabel is attached to and the antibody, antibody fragment, or a peptide, wherein RG is the radiolabel and A is the antibody, antibody fragment, or a peptide.

The basic premise of this disclosure is, then:
Conjugation of these multifunctional dPEG construct modulates the in vivo biodistribution and pharmacokinetics (absorption, distribution, metabolism, excretion) of the biologically active molecule; and
By designing the chemical connections through A (chemically reactable moiety) and within ～～～ and —— and, as the terminal dPEG portion, their attachment within the various versatile multifunctional constructs one can control the architecture and functional multiplicity of the general branched dPEG construct, thereby allowing a variety of in vivo parameters to be designed into the final conjugate, along with the ability to detect or probe with it, and deliver a therapeutic.
And, optionally, these linear dPEG constructs can be used in combination, within branched dPEG constructs to further define the functionality and the stealth properties of the surfaces of various nanoparticles and microparticles for similar applications to give unexpected effects.

Linear dPEG constructs as substantially pure single compounds (and the process optimization to get there) vs. mixtures of the conventional polymeric PEGs!

Keys in this disclosure are the methods for making the disclosed dPEG constructs that are substantially pure compositions. These are built from and comprised of the single compounds components of the linear dPEG components that are synthetically reacted together in combinations currently disclosed or using chemistries known in the art to make these substantially pure dPEG constructs. (Ref.: Davis, U.S. Pat. Nos. 7,888,536 and 8,637,711). The single component nature of the component linear and branched core dPEGs species (Davis, U.S. Pub. No. 20130052130) or moieties allows for the building of increasingly complex linear dPEG constructs as disclosed in this application as the substantially pure constructs. These constructs depending on the total number of individual linear dPEG component portions, ～～～ and ——, can range in purity of about 60% to 99% or higher.

In making the disclosed dPEG constructs the goal is to begin with essentially pure components with respect to the oligomer purity. The processes for making these can be controlled to where it can be up to greater than 99%. When it is at this level of purity, the disclosed dPEG constructs and their ultimate oligomeric purity is controlled by the efficiency and effectiveness of each step and the purification as is known in the art of organic chemistry. However when the oligomeric purity is less than 99%, then the purity of the final construct will be controlled largely by that purity, though not all constructs will be necessarily from the same oligomeric pure batch. But for instance, if for a 4 component-branched dPEG construct built from component parts that are 98% pure alone, the oligomeric purity of the final construct would still in theory be 92%. As compared to the conventional polymeric PEGs, the discussion of purity is nearly meaningless, but it is noted briefly below as contrast to the novel nature of the dPEG constructs disclosed herein and the methods for their preparation.

It is important to briefly contrast this to the conventional polymeric PEGs. To make a simple point, let us look as some highly hypothetical mixtures, very "pure" by polymer standards. Also, in the art, the term "monodispersed" is used to indicate a single component; however, these are still HIGHLY complex mixtures of approximately 20-25 and 30-40 for linear 1000 and 3400 MW polymers. Hence, this term is highly misleading when used in the art. (Ref. Example of a monodisperse polymeric PEG, PDI (polydispersity index)=1.01, FIG. 2 in reference, Y. Li, et al., "MALDI-TOF Mas Spectral Characterization of Polymers Containing an Azide Group: Evidence of Metastable Ions," Macromolecules, 43(14), 6225-6228(2010)).

The following, again, are very simple and completely hypothetical examples of the complexity imparted by just a linear polymer, and exacerbated by building these into component constructs as disclosed herein. Remembering that with a single component linear dPEG component, the final disclosed component dPEG construct is substantially pure and through the use of the taught methods can be essentially a single component.

Consider an example of a construct containing just 3 components. The most prominent component would have a "purity" of less than 50%, the other two making up the balance. To take these to a three-component construct, the final process mixture would now have 7 components. For a more realistic monodisperse with a linear component of about 1000, with "only" 20 components, the final 3-component construct would have at least 60 components! And this is for a so-called "monodisperse" system.

Another simple example of having just 5 components and converting this into a more typical 4 branched dPEG construct, which has been disclosed previously, or a multifunctional linear dPEG option disclosed herein, would in this highly hypothetical polymer give a combined mixture in the 5 component construct of 17 components. Hence the purity of a single component would likely be less than 6%.

From this simple analysis of the "purity" of the polymeric PEGs, it is apparent that there are hugely difficult characterization issues, but additionally the insolvable issue of reconciling the range of MW leading to a large range of PK and BD properties imparted by this huge mass of different biologically active agents all built in by the range of components in the polymer mixture. This does not address the primary issue on polymerization, which is the challenge of mixture process reproducibility.

In contrast, it can be seen with Avipep's dPEGylated diabody in vivo diagnostic product with of 4× m-dPEG$_{24}$ (four single chain linear dPEGs), where they see just ONE peak in the mass spec. (Ref. FIG. 14 in Hudson, et al., "Immuno-conjugates and Methods for Producing them," US 2010/0164068 A1 Jun. 28, 2012. This specifically is something that the FDA is very intrigued with in this instance in particular.) The single peak in dramatic contrast to what one sees when a conventional polymeric PEG is attached. In fact, in a perusal of the published literature one will not see published images of these data, as they are highly complex and generally bimodal. One can anticipate this by an example where just the MALDI mass spectra of a 5 kDa polydisperse polymer raw material in the m-PEG(5 kDa) amine, is contrasted to a linear dPEG. In the former one can see peaks going below 2 kDa and above 7 kDa, representing over 100 components, which the dPEG is a single peak. (See FIG. 2 in Anna Mero, Barbara Spolaore, Francesco M. Veronese and Angelo Fontana, "Transglutaminase-Mediated PEGylation of Proteins: Direct Identification of the Sites of Protein Modification by Mass Spectrometry using a Novel Monodisperse PEG," *Bioconjugate Chem.*, 2009, 20 (2), pp 384-389.)

In a previous publication, we have extolled the benefits of having PEGylation constructs that are branched discrete PEG constructs in particular, in order to give them the size that would allow for having discrete PEGylation constructs that are single molecules, as opposed to polymers, in order to modulate the pharmacokinetics to the particular requirement of various biologically active materials.

In addition to modulation of pharmacokinetics, the discrete PEG has the potential for the ability of building more enabling discrete PEGylation constructs by taking advantage of the linear discrete PEG constructs as essentially single molecules (Davis, U.S. Pat. Nos. 7,888,536 and 8,637,711), and thereby building or designing them into discrete PEG constructs incorporating one or more of the other properties of polyethylene glycol beyond just the ability to make the biologic look bigger to the host, while providing the additional capability of loading the therapeutic or diagnostic without having this exacerbate the properties of the biologic, but rather enhance them with the type of discrete construct designed and disclosed herein.

These properties could be one or more of the following, but not limited to, those that have been exhibited for polyethylene glycols: (a) stealth (e.g., stealth liposomes, stealth liposomes and long circulating nanoparticles: critical issues in pharmacokinetics, opsonization and protein-binding properties, S. M. Moghimia and J. Szebenib, Progress in Lipid Research, 42 (2003) 463-478); (b) improved biodistribution (In this specific case, by choosing an optimal discrete PEG for the peptide substrate, Ref. Real-Time Video Imaging of Protease Expression In Vivo, X. Chen, et al., Theranostics, 1 (2011) 18-27); (c) increased stability by protecting the diagnostic or therapeutic from the environment or reducing aggregation, and the like (Ref.: Polymer conjugates: nanosized medicines for treating cancer, Maria J. Vicent and Ruth Duncan, Trends in Biotechnology, 24 (2006) 39-47); (d) reduced immunogenicity by and while hiding the therapeutic; and (e) reduced toxicity (Ref.: The Impact of PEGylation on Biological Therapies, F. M. Veronese and Anna Mero, Biodrugs, 22 (2008) 315-329). These are known properties of the polyethylene glycol, but having a construct that incorporates the diagnostic or the therapeutic, or both, or multiples of either, would provide a significant enhancement to the current design options in the diagnostic and therapy industries.

Above, we have presented compelling and unexpected data about the properties of the disclosed linear and dPEG constructs.

DETAILED DESCRIPTION

Definitions (General)

The following definitions of terms as used herein are listed below:

Unless defined otherwise, all technical and scientific terms used herein generally have the same meaning as commonly understood by one of ordinary skill in the art to which this disclosure belongs. Generally, the nomenclature used herein and the laboratory procedures in cell culture, protein engineering, molecular genetics, organic chemistry and nucleic acid chemistry, and hybridization described below are those well-known and commonly employed in the art. Standard techniques are used for nucleic acid and peptide synthesis. Generally, enzymatic reactions, protein and related modification and crosslinking chemistry and purification steps are performed according to the manufacturers specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well-known and commonly employed in the art. Standard techniques, or modifications thereof, are used for chemical syntheses and chemical analyses.

"Substantially pure"—This purity is like that of traditional chemical synthesis where the components, which create the various discrete polyethylene glycol (discrete PEG) constructs, are each single compounds. The linear discrete PEG constructs are built from combinations of the individually pure components, ∼∼∼ and ——, in a like manner. The ∼∼∼ and —— are primarily composed of a discrete PEG and derivative made via the processes developed in U.S. Pat. Nos. 7,888,536 and 8,637,711. Additional purification to remove non-discrete PEG impurities can be carried out using conventional purification methodologies where necessary and optimized, especially recrystallization. Thus, the disclosed discrete PEG compounds and constructs typically are synthesized in a purity of greater than 60% for those with more complex molecular architecture and often greater than 80% or 90% or above for those with less complicated molecular architecture, especially those that are linear with a side chain G. Methods can generally be developed to make the various disclosed discrete PEG constructs of purities exceeding 97% or 98%. Even 60% purity is exceedingly higher than the simplest linear monodisperse mixture, where "purity" of the average component is much less than a few % in the best case (PDI=1.01), which are still extremely polydisperse by nature of the polymerization processes by which they are made.

"Wavy line", "∼∼∼". The wavy line, ∼∼∼, is a linear chain containing a discrete polyethylene glycol (discrete PEG) residue optionally substituted with N, S, Si, Se, or P, and optionally having linear side chains. Such wavy line may contain aryl groups, alkyl groups, amino acids, and the like. The end components of ∼∼∼ have independently chemically reactable or reactive moieties at each end. These are incorporated such that each end can be reacted independently during its incorporation to any discrete PEG construct or intermediates in the process of building the same. When the ends of the wavy line are chemically reactive groups, they can be reactive on their own, or can be masked groups, e.g., an azide as an amine, or protected reactable groups that must be converted to chemically reactive groups. The chemical construction of these compositions can have multiple wavy lines, the same or different. When they are different, the end groups, "A" must not react at the same time, and can be biorthogonal, or other combinations of masked or protected reactable groups known in the art. (Ref.: E. M. Sletten and C. R. Bertozzi, "Biorthogonal Chemistry: Fishing for Selectivity in a Sea of Functionality," Angew. Chem. Int. Ed., 48, 6974-6998(2009); G. Hermanson, Bioconjugate Techniques, 2$^{nd}$ Edition, Academic Press, 2008; T. Greene and P. Wutz, Greene's Protective Groups in Organic Synthesis, 4$^{th}$ ed., Wiley, 2007.) The use is the same as that disclosed in our U.S. Pat. Nos. 7,888,536 and 8,637,711. Some of the more preferred options are shown but not limited to those in Tables 1 and 2 in U.S. Pub. No. 20130052130, paragraphs (0102) and (0103). The chemically reactable or chemically reactive moieties as end groups on the wavy line also can be converted to biologically active groups. Generally this will be a final step or series of steps in the building of the compositions in this disclosure.

Furthermore, the wavy line ∼∼∼, which in the art also is termed a linker or spacer or spacer arm, means a chemical moiety comprising a covalent bond or a chain of atoms that covalently attaches a "preferential locator", like an antibody, or to a diagnostic or therapeutic group, like a drug moiety. Exemplary linker abbreviations include: MC=6-maleimido-caproyl, MPS=maleimidopropanoyl, val-cit=valine-citrulline, dipeptide site in protease-cleavable linker, ala-phe=alanine-phenylalanine, dipeptide site in protease-cleavable linker, PAB=paminobenzyloxycarbonyl, SPP=N-Succinimidyl 4-(2-pyridylthio) pentanoate, SMCC=N-Succinimidyl 4-(N maleimidomethyl) cyclohexane-I carboxylate, SIAB=NSuccinimidyl (4-iodo-acetyl) aminobenzoate, and these and others known in the art can be and preferred to be used in the disclose composition containing a linear discrete PEG, as well as those containing discrete PEG constructs described and defined below.

The wavy line ∼∼∼ also is defined such that it contributes important properties to be incorporated into or as part of the composition, as part of controlling and including the length and size of the discrete PEG. These also have practical considerations as they variably control the accessibility for reaction and also the dynamics and size on the final construct, as well as other design functions desirable to the application, e.g., cleavable/releasable, multifunctional. And the optimal lengths of the wavy line are preferred in this disclosure, where for discrete PEG$_x$, x is preferred from 2 to 72, more preferred from 8-24. The inherent properties of the discrete PEG as a type of PEG are known in the art.

The wavy line is defined to optionally incorporate a bond or chemical construct known in the art that will result in a cleavable bond or construct. Also see Tables 1 and 2 below for the preferred chemistries to use in this disclosure as part of the definition for the wavy line, ∼∼∼.

"Solid line," "——" solid lines, ——, are discrete PEG-containing chains that have between about 2 and 64 ethylene oxide residues and have a terminal moiety that is not an ethylene oxide. Optionally containing non-discrete PEGs, including a dPEG chain with an amide or similar bond, but a chain having only discrete PEGs is preferred. The terminal group generally will be a methyl group or methoxy group, or a charged group. The composition of the end groups on the solid line can be different. Both ends, independently, also could be chemically reactable group(s) or chemically reactive moiety(s), such that they can be incorporated into a linear or multifunctional composition during a synthetic process, or are as defined above. The solid line can contain aryl, alkyl, etc. groups, but it is preferred that it be a "simple" linear discrete PEG. On occasion, the solid line could incorporate a wavy line or be incorporated into a wavy line.

"A" can be a "biologically active group" or a "chemically reactive moiety" or a "chemically reactable moiety."

"A" as a "Chemically reactive moiety"—a "chemically reactive moiety" is one that will react as it is presented to and allowed to react in the chemical process. This is to be distinguished from a "chemically reactable group" can be used interchangeably, but is a chemical reactive group that is masked, like an azide, reducible to an amine, or a protected "chemically reactive group."

As used herein, or A—chemically reactive moiety—when two chemically reactive moieties are present in a construct, they are optimally designed to have complimentary reactivity. Hence the A's as "chemically reactive moieties" are a pair of reactive chemical moieties that will by the nature of atoms (well known in the art) react with one another, and designed to only react with each other under the predetermined process conditions in building the linear discrete PEG construct. They are selected from various chemistries known in the art in such a way to give ∼∼∼ the desired chemical, physical or steric properties desired for a particular application as it is built into various discrete PEG constructs architectures. Including and optionally giving the ends or a position in ∼∼∼ the propensity to now be a releasable. Some preferred options are listed, but not limited to, Tables 1 and 2 in U.S. Pub. No. 20130052130, paragraphs (0102) and (0103).

When the wavy line is being incorporated initially to a linear dPEG construct and both ends are "A", the same is true as the intermolecular reactability above.

Other A's include other sulfhydryl/thiol specific like iodo(halo)acetamides, vinyl sulfone, ETAC (that can react to two thiols, that can be the same or two different in a bispecific application, or bridge a disulfide); aminooxy derivatives to react with carbonyls like ketones and aldehydes; acetylides that can react with azides via a copper catalyzed or copper free click reactions.

"Chemically reactive moiety" also is a reactive functional group, and as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989). The reactive functional groups may be protected or unprotected (see, for example, Greene's Protective Groups in Organic Synthesis, Peter G. M. Wuts and Theodora W. Greene, John Wiley and Sons, 2007.

The term "Chemically reactable group" as "A" and as used herein is a masked or protected "chemically reactive group" and used such that where more than one "A" is in a method for making the various discrete PEG constructs, these do not interfere in the successful outcome of the syntheses. These options for having "chemically reactable groups" in the presence of "chemically reactive groups" are well known in the art. Many of these are shown below in Tables 1 and 2 in U.S. Pub. No. 20130052130, paragraphs (0102) and (0103).

Most of the chemically reactive moieties most preferred in this disclosure can be found in application in the representative references by Hermanson and Bertozzi, but not limited to these, and many are well known to those skilled in the art. (Ref.: .Bioconjugate Techniques, Greg T. Hermanson, Elsevier, $3^{rd}$ edition, 2013; ISBN 978-0-12-382239-0; b) "Biorthogonal Chemistry: Fishing for Selectivity in a Sea of Functionality," Ellen M. Sletten and Carolyn R. Bertozzi, *Angewandte Chemie Int. Ed.*, 2009, 48, 6974-6998.)

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include, for example, acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl, benzyl, benzoyl, tetrahydropyranyl, and trialkylsilyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitro ethyl and the like. For a general description d and l or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process (Ref.: Greene's Protective Groups in Organic Synthesis, Peter G. M. Wuts and Theodora W. Greene, John Wiley and Sons, 2007.

"A" as a "Biologically active group"—This is a biologically active group that is either able to target (preferential locator) a particular compound that is matched to A with a specific non-covalent affinity, e.g., or one that can interact with a target in specific and complementary ways, e.g., enzyme inhibitor peptide (A) to an enzyme released at a disease sight. Any of these biologically active groups inhibitor can be delivered with a radiolabel or a toxic drug that would kill the target, or can deliver a detectable probe as a diagnostic agent, or both.

"A" as a biologically active group is introduced into the discrete PEG constructs by the many chemistries known in the art, e.g., references: E. M. Sletten and C. R. Bertozzi, "Biorthogonal Chemistry: Fishing for Selectivity in a Sea of Functionality," Angew. Chem. Int. Ed., 48, 6974-6998 (2009); G. Hermanson, Bioconjugate Techniques, 3rd Edition, Academic Press, 2013. In addition the option for incorporating a cleavable chemistry into the linkage formed also is a preferred option. This could include but not limited to a cleavable peptide, a disulfide, or a hydrazine.

As used herein, "A" can be a targeting agent, or carrier with targeting agent (e.g., a nanoparticle that has the targeting agents attached to the particle with various linear discrete PEG constructs), the targeting agent matched to a particular target. A can be, e.g., a MMP (matrix metalloprotease) inhibitor substrate, an RGD peptide, antibody, antibody fragment, engineered scaffold, liposome, a PLGA, silica or a metal nanoparticle, such as gold or silver, all well known in the art or targeting for diagnostics and therapeutics. "A" can be a cell surface and matrix antigen, transport protein, receptor protein, an antibody, antibody fragment, engineered antibody, engineered fragment, peptide, peptide substrate, peptomimetic substrate, cytokine, aptamer, siRNA, vitamin, steroid, a nanoparticle, microparticle, engineered molecular scaffold that contains multiple functionalities, or an engineered chemically reactable group.

When there is more than one "A" as a "biologically active group", the term used is a multivalent group. The "A" independently can be the same or different depending on the intent and need of the particular application of "A". E.g., Two different "A's" give a bispecific interaction, or where "A" is the same, a single interaction can be enhanced, but in both cases there can be a very large advantage over having just one "A" and the design of the ~~~~ can control that synergy of having more than one "A," as disclosed in Davis, U.S. Pub. No. 20130052130 paragraphs (0209)-(0230).

The term, Terminal moiety, as used herein in this disclosure, is defined in terms of the group at the end of the solid line, ——, in a linear discrete PEG construct. Preferred groups are the methyl or methoxy, and the carboxyl/carboxylate, optionally other negatively charged groups, like a sulfonate. In certain cases, the terminal group can be a positively charged group, like guanidine, amine and the like, including short peptides. These groups may control cell penetration either positively or to prevent it, as well as the orientation and geometry of the variously disclosed discrete PEG constructs. Having multiple charged terminal groups, especially the carboxyl, is optimal in controlling the biodistribution, to unexpectedly increasing the apparent size of multiple linear discrete PEG constructs, and thereby give "small" dPEG constructs that will not go out the kidney and stay out of other organs, as well and thereby control much of the biodistribution of multiple linear discrete PEG constructs having "A" with a biologically active group attached and thereby direct the biologically active group to a preferred location very specifically while carrying a diagnostic or therapeutic or both groups.

Charged group: A charged group or groups are functional groups that have a net positive or negative charge. The presence and nature of the charge is generally dictated by the pH of the environment in which the group is found. E.g., at physiological pH of just above 7 the amine group is positive and the carboxylate is negative, as are the phosphate and sulfonate groups. Other positively charged groups may include guanidine. The preferred function is the same as for the terminal group, where the preferred terminal group is negatively charged, more preferred the carboxyl group, but optionally having a positive charge. Some discrete PEG constructs may be designed having both negative and positive charges in them by design. For therapeutic design a methoxy group is optionally preferred.

AC or

is an attachment core: The attachment core is a group, generally with a carbon core, but the core could also be N, Si, Se, or P, that has the potential of being incorporated into a linear template, where there is more than one

, which independently can be the same or different, and can be separated by a discrete PEG and ⌇⌇⌇. The

has an additional functional group that can be reactive or is reactable with another group to incorporate the

into the template construct as part of a more useful and versatile linear discrete PEG construct composition.

can be incorporated before the template is constructed, as part of

or can be added after the template is built. The latter would be preferred when the

and

are the same, and the former when the

and

are different.

G or

(DG and TG) is a group that is attached to

via ⌇⌇⌇ and can be a chemically reactable or reactive moiety to which is attached a diagnostic or therapeutic group or a basic linear discrete PEG construct. The templates can look like the following,

to which

are added, and in this case the

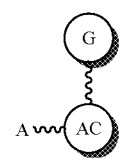

will be the same, or they can be built from the individual pieces, to give an

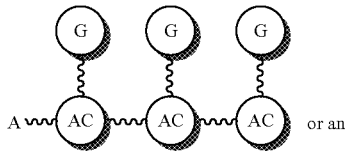 or an

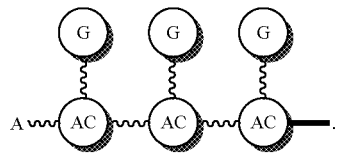.

When the

are the same, the disclosure herein uses the term, homotemplate or homomer or homomeric template; and when the

are different, we herein use the terms heterotemplate or heteromer or heteromeric template.

can be any side functional amino acid, natural or unnatural, preferred are the lysine, tyrosine, or aspartic acid, but not limited to. Disclosed herein is the versatility of the tyrosine as a multifunctional core, especially to include discrete PEGs on the phenolic OH, and especially for creating novel and versatile

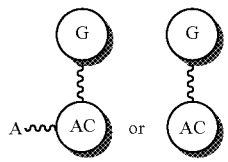

constructs. G can also have a linear m-dPEG$_x$ attached to it, that preferably is cleavable, where x can vary from 2 to 48 units.

As used herein, "G" means a protected or masked reactive chemical moiety; "reactive chemical moiety"=group of atoms that will react with another group of atoms to form the desired chemical bond or bonds based on the electronic and/or steric nature of the reacting group of atoms. "G" has the same options at "A" (chemically reactive group above), but have defined it separately to distinguish it as reactive functionality coming off of template AC's wavy lines. (Refs.: (a) March's Advanced Organic Chemistry: Reactions, Mechanism and Structure, Michael B. Smith and Jerry March, John Wiley & Sons, 2001; and (b) Greene's Protective Groups in Organic Synthesis, Peter G. M. Wuts and Theodora Greene, 4$^{th}$ ed., John Wiley & Sons, 2007.) "G" is convertible to a "G" that can be a "DG", diagnostic group, or a "TG", a therapeutic group, but is not limited to groups with just these functionality and applicability.

Diagnostic Group

The term "diagnostic group", abbreviated "DG," which is used interchangeably with "detectable label" is intended to mean a moiety having a detectable physical, chemical, or magnetic property. This includes such labels as biotin and its derivatives, which are matched with the entire range of streptavidin conjugates, dyes, fluorescent and chromogenic, radioisotopes as labels, including chelating groups such as DOTA and NOTA derivative. In all of these cases the use of the linear discrete PEG in the attachment chemistry is preferred. (Refs.: D. Scott Wilbur, "Chemical and Radiochemical Considerations in Radiolabeling with alpha-Emitting Radionuclides," Current Radiopharmaceuticals, 4, 214-247(2011); M. Famulok, et al., "Functional Aptamers and Aptazymes in Biotechnology, Diagnostics, and Therapy," Chem. Rev., 107(9), 3715-3743(2007); S. S. Kelkar and T. M. Reineke, "Theranostics: Combining Imaging and Therapy," Bioconjugate Chemistry, 22, 1879-1903); "Molecular Probes Handbook, A Guide to Fluorescent Probes and Labeling Technologies," 11$^{th}$ Edition, Iain Johnson and M. Spence, Ed., ISBN-10: 0982927916.

A novel DOTA derivative that can be used to make a wide range of useful chelating reagents to create a diagnostic group as an imaging agent, especially incorporating various discrete PEG constructs as wavy lines, to control where it is place in the diagnostic or imaging system and can be used as effective parts of linear discrete PEG constructs.

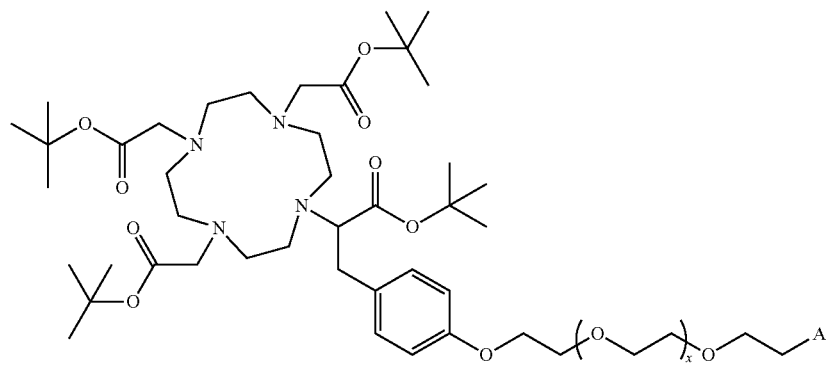
DOTA/DOTA-TBE-Tyr(-dPEG$_x$-A)-OH/TBE; x = 4, 8, 12, 24, 36
(G)⌇⌇A; (G) = Tyrosine-DOTA = DG or TG
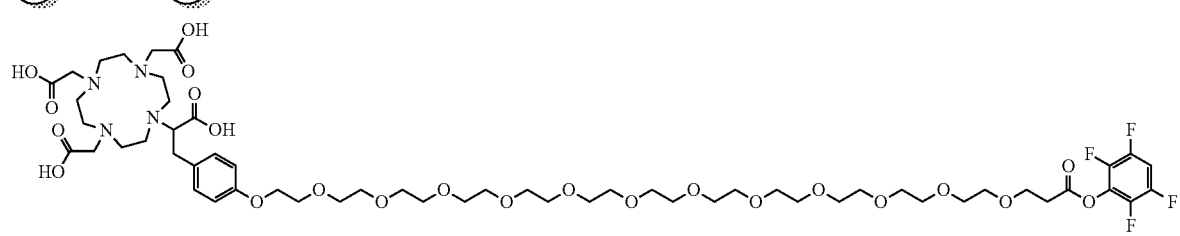
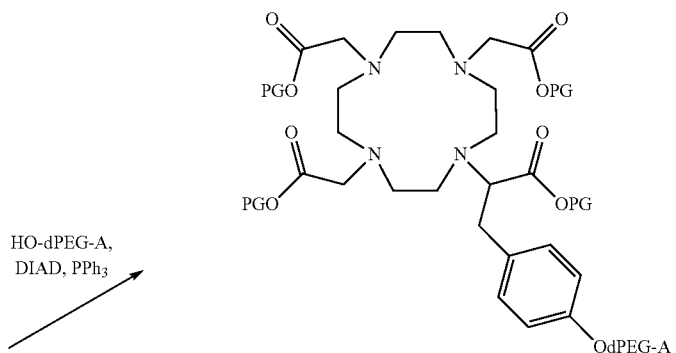
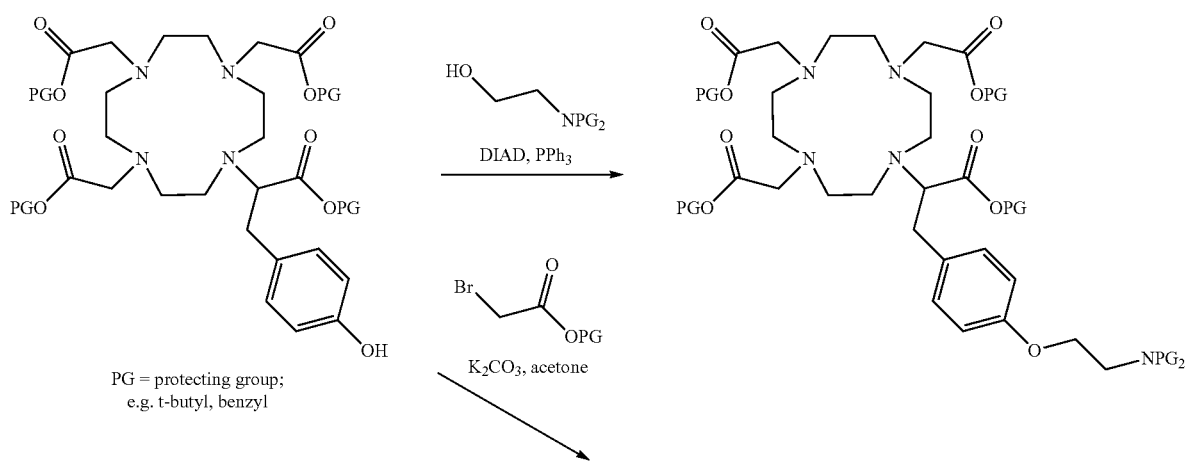
PG = protecting group;
e.g. t-butyl, benzyl

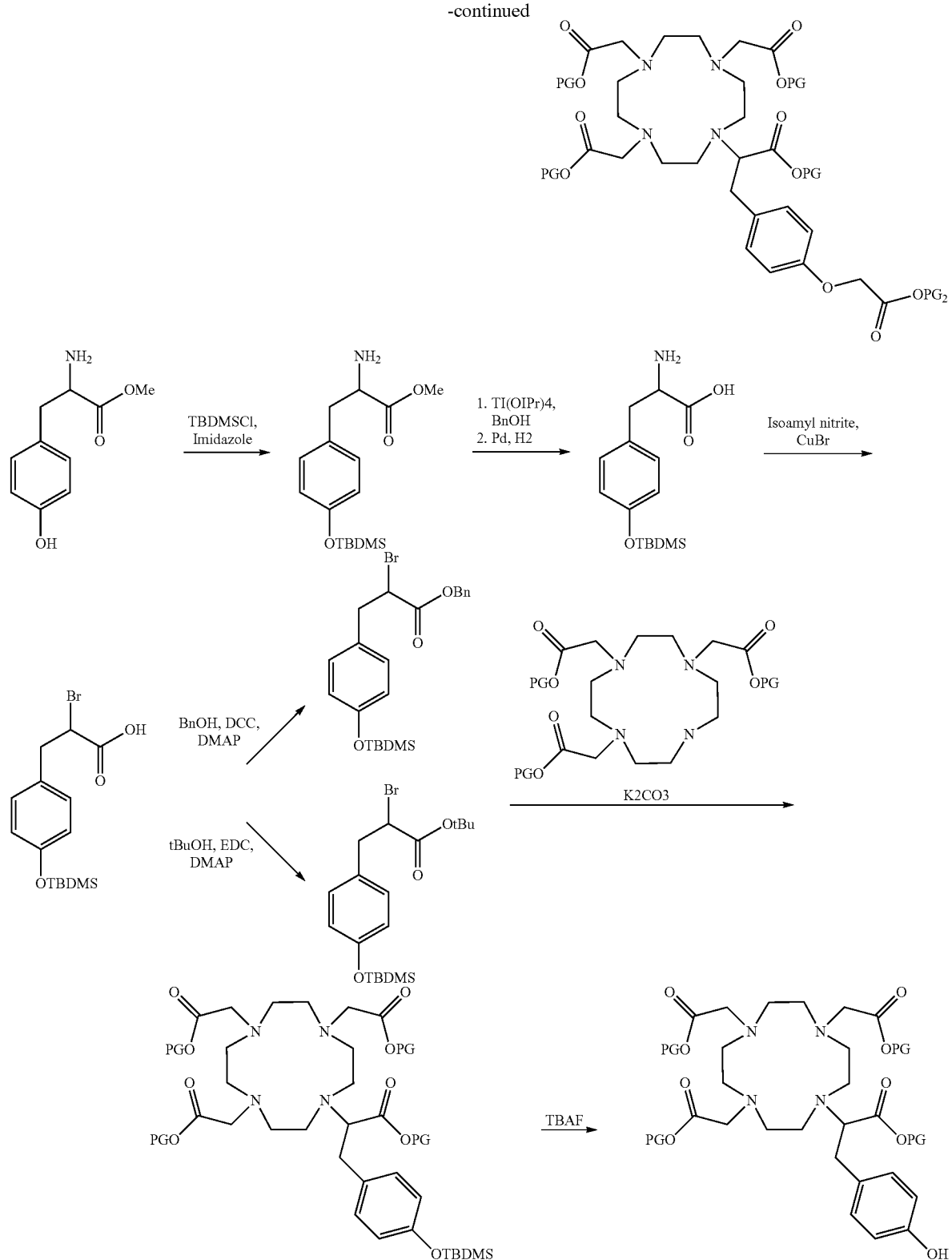

TG (Therapeutic Group)

The term "therapeutic (group)" abbreviated "TG," is intended to mean a compound that, when present in a therapeutically effective amount, produces a desired therapeutic effect on a mammal. For treating carcinomas, it is desirable that the therapeutic agent also be capable of entering the target cell. A therapeutic group can be from among the cytotoxins. Herein, the term "cytotoxin" is intended to mean a therapeutic agent having the desired effect of being cytotoxic to cancer cells. Cytotoxic means that the agent arrests the growth of or kills the cells. Exemplary cytotoxins include, by way of example and not limitation, combretastatins, duocarmycins, the CC-1065 anti-tumor antibiotics, anthracyclines, and related compounds. Other cytotoxins include mycotoxins, ricin and its analogues, calicheamycins, doxirubicin and maytansinoids. A good recent review reference on natural products and their potential impact on new anti-cancer drugs is referenced here. ("Impact of Natural Products on Developing New Anti-Cancer Agents," David J. Newman, et al., *Chemical Reviews,* 2009, 109, 3012-3043)

As used herein, the term "therapeutic group" is any compound that is a "drug", "anticancer agent", "chemotherapeutic agent", "antineoplastic", and "antitumor agent" are used interchangeably and refer to agent(s) (unless further qualified) that have the property of inhibiting or reducing aberrant cell growth, e.g., a cancer. The foregoing terms also are intended to include cytotoxic, cytocidal, or cytostatic agents. The term "agent" includes small molecules, macromolecules (e.g., peptides, proteins, antibodies, or antibody fragments), and nucleic acids (e.g., gene therapy constructs), recombinant viruses, nucleic acid fragments (including, e.g., synthetic nucleic acid fragments). (Ref.: M. Famulok, "Functional Aptamers and Atazymes in Biotechnology, Diagnostics, and Therapy," Chem. Rev., 107(9), 3715 (2007)

Therapeutic groups also can be radionuclides (Ref. (a) D. Scott Wilbur, "Chemical and Radiochemical Considerations in Radiolabeling with -Emitting Radionuclides," Current Radiopharmaceuticals, 4, 214-247(2011); (b) Monoclonal antibody and peptide-targeted radiotherapy of cancer, R. M. Reilly, ed., J. Wiley and Sons, 2010, ISBN 978-0-470-24372-5; (c) Targeted Radionuclide Therapy, Tod W. Speer, ed., Lippincott, 2011, ISBN 978-0-7817-9693-4.)

Nanoparticle

As used herein, the term "nanoparticles" refers to particles of about 0.1 nm to about 1 μm, 1 nm to about 1 μm, about 10 nm to about 1 μm, about 50 nm to about 1 μm, about 100 nm to about 1 μm, about 250-900 nm in size, or, advantageously, about 600-800 nm. The nanoparticles may comprise macromolecules, gene therapy constructs, or chemotherapeutic agents, for example.

As used herein, the term "microparticles" refers to particles of about 0.1 μm to about 100 μm, about 0.5 μm to about 50 μm, 0.5 μm to about 20 μm in size, advantageously, particles of about 1 μm to about 10 μm in size, about 5 μm in size, or mixtures thereof. The microparticles may comprise macromolecules, gene therapy constructs, or chemotherapeutic agents, for example.

The term "cleavable group" is intended to mean a moiety that can be unstable in vivo. Preferably the "cleavable group" allows for activation of the marker or therapeutic agent by cleaving the marker or agent from the rest of the conjugate. Operatively defined, the linker is preferably cleaved in vivo by the biological environment. The cleavage may come from any process without limitation, e.g., enzymatic, reductive, pH, etc. Preferably, the cleavable group is selected so that activation occurs at the desired site of action, which can be a site in or near the target cells (e.g., carcinoma cells) or tissues such as at the site of therapeutic action or marker activity. Such cleavage may be enzymatic and exemplary enzymatically cleavable groups include natural amino acids or peptide sequences that end with a natural amino acid, and are attached at their carboxyl terminus to the linker. While the degree of cleavage rate enhancement is not critical to the disclosure, useful examples of cleavable linkers are those in which at least about 10% of the cleavable groups are cleaved in the blood stream within 24 hours of administration, most preferably at least about 35%. Included in this term is the option of having a "self immolative spacer". The term "self-immolative spacer" refers to a bifunctional chemical moiety that is capable of covalently linking two chemical moieties into a normally stable tripartite molecule. The self-immolative spacer is capable of spontaneously separating from the second moiety if the bond to the first moiety is cleaved. Listed are references representing the range of cleavable chemistries potentially applicable in this disclosure, which can be utilized with the benefit by incorporation into the wavy or solid lines, especially containing discrete PEGs, as part of a linear dPEG or the attachment core.

a. "Releasable PEGylation of proteins with customized linkers," David Filpula and Hong Zhao, Advances in Drug Delivery Reviews, 2008, 60, 29-49.
b. "A Mild Chemically Cleavable Linker System for Functional Proteomic Applications," Steven H. L. Verhelst, Marko Fonovic', and Matthew Bogyo, Angew. Chem. Int. Ed. 2007, 46, 1-4.
c. "Enzyme-Catalyzed Activation of Anticancer Prodrugs," MARTIJN ROOSEBOOM, JAN N. M. COMMANDEUR, AND NICO P. E. VERMEULEN, Pharmacol Rev 56:53-102, 2004.
d. "Elongated Multiple Electronic Cascade and Cyclization Spacer Systems in Activatible Anticancer Prodrugs for Enhanced Drug Release," Hans W. Scheeren, et al., *J. Org. Chem.* 2001, 66, 8815-8830.
e. "Controlled Release of Proteins from Their Poly(Ethylene Glycol) Conjugates: Drug Delivery Systems Employing 1,6-Elimination," Richard B. Greenwald, et al., Bioconjugate Chem. 2003, 14, 395-403.

The term "pro drug" and the term "cleavable moiety" often can be used herein interchangeably. Both refer to a compound that is relatively innocuous to cells while still in the conjugated form, but which is selectively degraded to a pharmacologically active form by conditions, e.g., enzymes, located within or in the proximity of target cells. (Ref.: P. J. Sinko, et al., "Recent Trends in Targeted Anticancer Prodrug and Conjugate Design," Curr. Med. Chem., 15(18), 1802-1826(2008); S. S. Banerjee, et al., Poly(ethylene glycol)-Prodrug Conjugates: Concept, Design, and Applications," J. of Drug Delivery, Article ID 103973 (2012); J. Rautio, et al., "Prodrugs: design and clinical applications," Nature Review, Drug Discovery, 7, 255-270 (2008).)

Preferential locator often can be used largely interchangeably with ligand or "targeting group" and can be either a "diagnostic group" or a "therapeutic group" or the like. Broadly, preferential locators are molecularly targeted agent defined as drugs that target growth factor receptors and signal transduction pathways. NPOA molecule is used for targeting molecular entities, cells, tissues or organs in a biological system. With respect to neoplastic tissue (cancer cells), a "preferential locator" (or "locator") specifically binds a marker produced by or associated with, for example, neoplastic tissue, antibodies and somatostatin congeners being representative such locators. Broader, however, a "locator" includes a substance that preferentially concentrates at the tumor sites by binding with a marker (the cancer cell or a product of the cancer cell, for example) produced by or associated with neoplastic tissue or neoplasms. Appropriate locators today primarily include antibodies (whole and monoclonal), antibody fragments, chimeric versions of whole antibodies and antibody fragments, and humanized versions thereof. It will be appreciated, however, that single chain antibodies (SCAs, such as disclosed in U.S. Pat. No.

4,946,778, incorporated herein by reference) and like substances have been developed and may similarly prove efficacious. For example, genetic engineering has been used to generate a variety of modified antibody molecules with distinctive properties. These include various antibody fragments and various antibody formats. An antibody fragment is intended to mean any portion of a complete antibody molecule. These include terminal deletions and protease digestion-derived molecules, as well as immunoglobulin molecules with internal deletions, such as deletions in the IgG constant region that alter Fc mediated antibody effector functions. Thus, an IgG heavy chain with a deletion of the Fc CH2 domain is an example of an antibody fragment. It is also useful to engineer antibody molecules to provide various antibody formats. In addition to single chain antibodies, useful antibody formats include divalent antibodies, tetrabodies, triabodies, diabodies, minibodies, camelid derived antibodies, shark derived antibodies, and other antibody formats. Aptamers form yet a further class of preferential locators. All of these antibody-derived molecules are example of preferential locators.

Various suitable antibodies (including fragments, single chains, domain deletions, humanized, etc.) include, for example, B72.3, CC49, V59, and 3E8 (see U.S. Pat. No. 8,119,132), all directed against adenocarcinomas.

In addition to antibodies, biochemistry and genetic engineering have been used to produce protein molecules that mimic the function of antibodies. Avimers are an example of such molecules. See, generally, Jeong, et al., "Avimers hold their own", *Nature Biotechnology* Vol. 23 No. 12 (December 2005). Avimers are useful because they have low immunogenicity in vivo and can be engineered to preferentially locate to a wide range of target molecules such as cell specific cell surface molecules. Although such substances may not be subsumed within the traditional definition of "antibody", avimer molecules that selectively concentrate at the sites of neoplastic tissue are intended to be included within the definition of preferential locator. Thus, the terms "locator" was chosen, to include present-day antibodies and equivalents thereof, such as avimers, as well as other engineered proteins and substances, either already demonstrated or yet to be discovered, which mimic the specific binding properties of antibodies in the inventive method disclosed therein. (Refs.: "Engineered protein scaffolds as next-generation antibody therapeutics," Michaela Gebauer and Arne Skerra, *Current Opinion in Chemical Biology,* 2009, 13, 245-255; "Adnectins: engineered target-binding protein therapeutics," D Lipovsek, *Protein Engineering, Design & Selection,* 2010, 1-7.)

For other disease types or states, other compounds will serve as preferential locators.

The term "preferential locator" also can include terms like "targeting group" and "targeting agent" and are intended to mean a moiety that is (1) able to direct the entity to which it is attached (e.g., therapeutic agent or marker) to a target cell, for example to a specific type of tumor cell or (2) is preferentially activated at a target tissue, for example a tumor. The targeting group or targeting agent can be a small molecule, which is intended to include both nonpeptides and peptides. The targeting group also can be a macromolecule, which includes saccharides, lectins, receptors, ligands for receptors, proteins such as BSA, antibodies, and so forth. (Refs.: (a) "Peptides and Peptide Hormones for Molecular Imaging and Disease Diagnosis," Xiaoyuan Chen, et al., *Chemical Reviews,* 2010, 110, 3087-3111; (b) "Integrin Targeted Therapeutics," N. Neamati, et al., *Theranostics,* 2011, 1, 154-188; (c) "Integrin Targeting for Tumor Optical Imaging," Yunpeng Ye, et al., *Theranostics,* 2011, 1, 102-126.)

The term "marker" is intended to mean a compound useful in the characterization of tumors or other medical condition, and is therefore a target for the "preferential locator". E.g., in the cases of the, diagnosis, progression of a tumor, and assay of the factors secreted by tumor cells. Markers are considered a subset of "diagnostic agents." (Ref.: "Antibody-Drug Conjugate Targets," B. A. Teicher, *Current Cancer Drug Targets,* 2009, 9, 982-1004.) Marker is one target, a major target of a preferential locator. The term "ligand" means any molecule that specifically binds or reactively associates or complexes with a receptor, substrate, antigenic determinant, or other binding site on a target cell or tissue. Examples of ligands include antibodies and fragments thereof (e.g., a monoclonal antibody or fragment thereof), enzymes (e.g., fibrinolytic enzymes), biologic response modifiers (e.g., interleukins, interferons, erythropoietin, or colony stimulating factors), peptide hormones, and antigen-binding fragments thereof. (Ref.: U.S. Pat. No. 7,553,816).

The terms "polypeptide," "peptide" and "protein" are used interchangeably herein to refer to a defined polymer of amino acid residues, optionally incorporating a discrete PEG spacer or side chain. The terms apply to defined amino acid polymers in which one or more amino acid residue is an artificial chemical mimetic of a corresponding naturally occurring amino acid, as well as to naturally occurring defined amino acid polymers and non-naturally occurring amino acid sequences.

The term "amino acid" refers to naturally occurring and synthetic amino acids, either of L- or D-stereochemical configurations. (Ref.: U.S. Pat. No. 7,553,816; Chang C. Liu and Peter G. Schultz, "Adding New Chemistries to the Genetic Code," Annu. Rev. Biochem., 79, 413-444(2010)).

The following references are cited as diagnostic, imaging, and therapeutic examples, which alone or in combination, that can be used as the biology and chemistry base into which or upon which, or can be constructed in multiples in addition to a single unit, the discrete PEG constructs taught in this disclosure can be designed to give the unexpected and dramatic improvements that have been shown in some very simple cases. Such references are expressly incorporated into this disclosure by reference.

A's as biologically active species can fall into a number of areas. Many of these have been explored for their use as diagnostic or therapeutic agents and in some cases both applications. Herein we disclose dPEG constructs that can enable many of those that have been studies extensively, but lack the necessary properties to be optimally effect in the said published application, to be significantly more effective and act as sources for future generations of diagnostics and therapeutic agents.

For peptides in particular, but also for other "smaller" biologics that act as biologically active materials or preferential locators, the herein disclosed dPEG constructs can be matched with the various dPEG constructs disclosed in Davis, U.S. Pub. No. 2013/0052130, where these biologically active materials can be constructs as multiples the same, or as heterospecific materials. These are specifically disclosed in paragraphs (0209)-(0230).

Below are listed references for "A" as a peptide(s) as the biologically active moiety for the dPEG constructs disclosed herein, especially preferred when the "A"'s are used as the embodiments in Davis, U.S. Pub. No. 2013/0052130, paragraphs (0209)-(0230).

1. Disabling ErbB Receptors with Rationally Designed Exocyclic Mimetics of Antibodies: Structure-Function Analysis, Alan Berezov, Hong-Tao Zhang, Mark I. Greene, and Ramachandran Murali, *J. Med. Chem.* 2001, 44, 2565-2574.
2. Noberini R, Mitra S, Salvucci O, Valencia F, Duggineni S, et al. (2011) PEGylation Potentiates the Effectiveness of an Antagonistic Peptide That Targets the EphB4 Receptor with Nanomolar Affinity. PLoS ONE 6(12): e28611. doi:10.1371/journal.pone.0028611.
3. Structure-Activity Relationships of Linear and Cyclic Peptides Containing the NGR Tumor-homing Motif, Giorgio Colombo, Flavio Curnis, Giacomo M. S. De Mori, Anna Gasparri, Cristina Longoni, Angelina Sacchi, Renato Longhi, and Angelo Corti, THE JOURNAL OF BIOLOGICAL CHEMISTRY Vol. 277, No. 49, Issue of December 6, pp. 47891-47897, 2002.
4. Identification of a high affinity TAG-72 binding peptide by phage display selection, Nan Xiao, Dengfeng Cheng, Yi Wang, Ling Chen, Xinrong Liu, Shuping Dou, Guozheng Liu, Minmin Liang, Donald J. Hnatowich, Mary Rusckowski, Cancer Biology & Therapy 11:1, 22-31; Jan. 1, 2011).
5. Peptide-based radiopharmaceuticals and cytotoxic conjugates: Potential tools against cancer, S. M. Okarvi, Cancer Treatment Reviews (2008) 34, 13-26.
6. Radiolabeled Peptides: Valuable Tools for the Detection and Treatment of Cancer, M. Fani, H. R. Maecke, S. M. Okarvi Theranostics, 2012; 2(5):481-501. doi: 10.7150/thno.4024.
6. Synthesis of Peptide Radiopharmaceuticals for the Therapy and Diagnosis of Tumor Diseases, Mazen Jamous, Uwe Haberkorn and Walter Mier, *Molecules* 2013, 18, 3379-3409; doi:10.3390/molecules18033379.
7. Synthesis of Target-Specific Radiolabeled Peptides for Diagnostic Imaging Jakub Fichna and Anna Janecka, *Bioconjugate Chem.* 2003, 14, 3-17.
8. Disabling ErbB Receptors with Rationally Designed Exocyclic Mimetics of Antibodies: Structure-Function Analysis, Alan Berezov, Hong-Tao Zhang, Mark I. Greene, and Ramachandran Murali, *J. Med. Chem.* 2001, 44, 2565-2574.
9. Mechanistic Studies of a Peptidic GRP78 Ligand for Cancer Cell-Specific Drug Delivery, Ying Liu, Sebastian C. J. Steiniger, YoungSoo Kim, Gunnar F. Kaufmann, Brunhilde Felding-Habermann, and Kim D. Janda, Molecular Pharmaceutics, 2007, 4(3), 435-447.
10. Radiolabeled Cyclic RGD Peptides as Radiotracers for Imaging Tumors and Thrombosis by SPECT, Yang Zhou, Sudipta Chakraborty and Shuang Liu, Theranostics, 1, 58-82 (2011).
11. Luteinizing Hormone Release and gonadotropin-releasing Hormone (GnRH) Receptor Internalization: Independent Actions of GnRH, P. Michael Conn and Eli Hazum, Endocrinology, 109 (6), 2040-2045 (1981).
12. Molecular Targeting of BCL2 and BCLXL Proteins by Synthetic BCL2 Homology 3 Domain Peptide Enhances the Efficacy of Chemotherapy, Sonia S. Dharap, Pooja Chandna, Yang Wang, Jayant J. Khandare, Bo Qiu, Stanley Stein, and Tamara Minko, THE JOURNAL OF PHARMACOLOGY AND EXPERIMENTAL THERAPEUTICS Vol. 316, No. 3, 94243/3081337; JPET 316: 992-998, 2006.
13. Novel Polymeric Prodrug with Multivalent Components for Cancer Therapy, Jayant J. Khandare, Pooja Chandna, Yang Wang, Vitaly P. Pozharov, and Tamara Minko 0022-3565/06/3173-929-937, THE JOURNAL OF PHARMACOLOGY AND EXPERIMENTAL THERAPEUTICS Vol. 317, No. 3; 98855/3108030; JPET 317:929-937, 2006.
14. Targeted Proapoptotic Anticancer Drug Delivery System, Pooja Chandna, Maha Saad, Yang Wang, Elizabeth Ber, Jayant Khandare, Alexandre A. Vetcher, Viatcheslav A. Soldatenkov, and Tamara Minko, MOLECULAR PHARMACEUTICS VOL. 4, NO. 5, 668-678 (2007).
15. Tumor-specific targeting of an anticancer drug delivery system by LHRH peptide, S. S. Dharap, Y. Wang, P. Chandna, J. J. Khandare, B. Qiu, S. Gunaseelan, P. J. Sinko, S. Stein, A. Farmanfarmaian, and T. Minko, 12962-12967_PNAS_Sep. 6, 2005_vol. 102_no. 36.
16. Cyclotides, a novel ultrastable polypeptide scaffold for drug discovery Andrew Gould, Yanbin Ji, Teshome L. Aboye, and Julio A. Camarero, Curr Pharm Des. 2011 December; 17(38): 4294-4307.
17. Integrin Targeted Delivery of Chemotherapeutics, Kai Chen and Xiaoyuan Chen Theranosttiics 2011; 1:189-200.
18. Integrin Targeted Delivery of Radiotherapeutics, Zhaofei Liu, Fan Wang and Xiaoyuan Chen, Theranostics, 2011; 1:201-210.
19. Integrin Targeting for Tumor Optical Imaging, Yunpeng Ye and Xiaoyuan Chen, Theranostics 2011; 1:102-126.
20. Multimodality Imaging of Integrin $\alpha v\beta 3$ Expression, Yin Zhang, Yunan Yang, Weibo Cai, Theranostics 2011; 1:135-148.
21. Synthesis and Evaluation of a Bimodal CXCR4 Antagonistic Peptide, Joeri Kuil, Tessa Buckle, Hushan Yuan, Nynke S. van den Berg, Shinya Oishi, Nobutaka Fujii, Lee Josephson, and Fijs W. B. van Leeuwen, dx.doi.org/10.1021/bc2000947|Bioconjugate Chem. 2011, 22, 859-864.
22. Incorporation of Monodisperse Oligoethyleneglycol Amino Acids into Anticonvulsant Analogues of Galanin and Neuropeptide Y Provides Peripherally Acting Analgesics, Liuyin Zhang, Brian D. Klein, Cameron S. Metcalf, Misty D. Smith, Daniel R. McDougle, Hee-Kyoung Lee, H. Steve White, and Grzegorz Bulaj; dx.doi.org/10.1021/mp300236v; Mol. Pharmaceutics 2013, 10, 574-585.
23. Design of a Modular Tetrameric Scaffold for the Synthesis of Membrane-Localized D-Peptide Inhibitors of HIV-1 Entry J. Nicholas Francis, Joseph S. Redman, Debra M. Eckert, and Michael S. Kay; dx.doi.org/10.1021/bc300076f|Bioconjugate Chem. 2012, 23, 1252-1258.
24. 99mTc-Labeled Bombesin(7-14)NH2 with Favorable Properties for SPECT Imaging of Colon Cancer, Jiyun Shi, Bing Jia, Zhaofei Liu, Zhi Yang, Zilin Yu, Kai Chen, Xiaoyuan Chen, Shuang Liu, and Fan Wang, *Bioconjugate Chem.* 2008, 19, 1170-1178.
25. Tumor Uptake of the RGD Dimeric Probe 99mTc-G3-2P4-RGD2 is Correlated with Integrin rv_3 Expressed on both Tumor Cells and Neovasculature, Zhaofei Liu, Bing Jia, Jiyun Shi, Xiaona Jin, Huiyun Zhao, Fang Li, Shuang Liu, and Fan Wang, *Bioconjugate Chem.* 2010, 21, 548-555.
26. [111In-DOTA]Somatostatin-14 analogs as potential pan-somatostatin-like radiotracers—first results of a preclinical study, Aikaterini Tatsi, Theodosia Maina, Renzo Cescato, Beatrice Waser, Eric P Krenning, Marion de Jong, Paul Cordopatis, Jean Claude Reubi and Berthold A Nock Tatsi et al., EJNMMI Research 2012, 2:25.
27. 68Ga-DOTA-Tyr3-Octreotide PET for Assessing Response to Somatostatin-Receptor-Mediated Radionuclide Therapy, Michael Gabriel, Andreas Oberauer, Georg Dobrozemsky, Clemens Decristoforo, Daniel Putzer, Dorota Kendler, Christian Uprimny, Peter Kovacs, Reto Bale, and Irene J. Virgolini, J Nucl Med 2009; 50:1427-1434; DOI: 10.2967/jnumed.108.053421.
28. Conventional and High-Yield Synthesis of DTPA-Conjugated Peptides: Application of a Monoreactive DTPA to DTPA-D-Phe1-octreotide Synthesis, Yasushi Arano, Hiromichi Akizawa, Takashi Uezono, Kenichi Akaji, Masahiro Ono, Susumu Funakoshi, Mitsuru Koizumi, Akira Yokoyama, Yoshiaki Kiso, and Hideo Saji, Bioconjugate Chem. 1997, 8, 442-446.
29. Improvement of Pharmacokinetics of Radioiodinated Tyr3-Octreotide by Conjugation with Carbohydrates, Margret Schottelius, Hans-Jurgen Wester, Jean Claude Reubi, Reingard Senekowitsch-Schmidtke, and Markus Schwaiger, *Bioconjugate Chem.* 2002, 13, 1021-1030.
30. Novel, Potent, and Radio-Iodinatable Somatostatin Receptor 1 (sst1) Selective Analogues, Judit Erchegyi, Renzo Cescato, Christy Rani R. Grace, Beatrice Waser, Véronique Piccand, Daniel Hoyer, Roland Riek, Jean E. Rivier, and Jean Claude Reubi, *J. Med. Chem.* 2009, 52, 2733-2746.
31. Ring Size of Somatostatin Analogues (ODT-8) Modulates Receptor Selectivity and Binding Affinity, Judit Erchegyi, Christy Rani R. Grace, Manoj Samant, Renzo Cescato, Veronique Piccand, Roland Riek, Jean Claude Reubi, and Jean E. Rivier, *J. Med. Chem.* 2008, 51, 2668-2675.
32. N-Terminal Sugar Conjugation and C-Terminal Thr-for-Thr(ol) Exchange in Radioiodinated Tyr3-octreotide: Effect on Cellular Ligand Trafficking in Vitro and Tumor Accumulation in Vivo, Margret Schottelius, Jean Claude Reubi, Veronique Eltschinger, Markus Schwaiger, and Hans-Jurgen Wester, *J. Med. Chem.* 2005, 48, 2778-2789.
33. One-Step 18F-Labeling of Carbohydrate-Conjugated Octreotate-Derivatives Containing a Silicon-Fluoride-Acceptor (SiFA): In Vitro and in Vivo Evaluation as Tumor Imaging Agents for Positron Emission Tomography (PET), Carmen Wangler, Beatrice Waser, Andrea Alke, Ljuba Iovkova, Hans-Georg Buchholz, Sabrina Niedermoser, Klaus Jurkschat, Christian Fottner, Peter Bartenstein, Ralf Schirrmacher, Jean-Claude Reubi, Hans-Jurgen Wester, and Björn Wängler *Bioconjugate Chem.* 2010, 21, 2289-2296.
34. Antagonist Binding Affinity and Selectivity, Christy Rani R. Grace, Judit Erchegyi, Manoj Samant, Renzo Cescato, Veronique Piccand, Roland Riek, Jean Claude Reubi, and Jean E. Rivier, *J. Med. Chem.* 2008, 51, 2676-2681.
35. Synthesis and biological activities of potent peptidomimetics selective for somatostatin receptor subtype 2, Lihu Yang, Scott C. Berk, Susan P. Rohrer, Ralph T. Mosley, Liangqin Guo, Dennis J. Underwood, Byron H. Arison, Elizabeth T. Birzin, Edward C. Hayes, Sudha W. Mitra, Rupa M. Parmar, Kang Cheng, Tsuei-Ju Wu, Bridgette S. Butler, Forrest Foor, Alexander Pasternak, Yanping Pan, Maria Silva, Roger M. Freidinger, Roy G. Smith, Kevin Chapman, James M. Schaeffer, And Arthur A. Patchett, *Proc. Natl. Acad. Sci. USA, Vol.* 95, pp. 10836-10841, September 1998.
36. Flexible antibodies with nonprotein hinges, Daniel J. CAPON, Naoki KANEKO, Takayuki YOSHIMORI, Takashi SHIMADA, Florian M. WURM, Peter K. HWANG, Xiaohe TONG, Staci A. ADAMS, Graham SIMMONS, Taka-Aki SATO and Koichi TANAKA, Proc. Jpn. Acad., Ser. B 87 (2011) 603-616.
37. Dimeric peptide agonists of the GLP-1 receptor, Novo Nordisk, Inc., US Pat. Appl., 2009/0062192 Mar. 5, 2009.
38. 2-Mercaptoacetylglycylglycyl (MAG2) as a Bifunctional Chelator for 99mTc-Labeling of Cyclic RGD Dimers: Effect of Technetium Chelate on Tumor Uptake and Pharmacokinetics, Jiyun Shi, Young-Seung Kim, Sudipta Chakraborty, Bing Jia, Fan Wang, and Shuang Liu, *Bioconjugate Chem.* 2009, 20, 1559-1568 1559.
39. 18F-Labeled Galacto and PEGylated RGD Dimers for PET Imaging of $\alpha v\beta 3$ Integrin Expression, Shuanglong Liu, Zhaofei Liu, Kai Chen, Yongjun Yan, Petra Watzlowik, Hans-Jurgen Wester, Frederick T. Chin, and Xiaoyuan Chen, Mol Imaging Biol. 2010 October; 12(5): 530-538. doi:10.1007/s11307-009-0284-2.
40. 68Ga-labeled cyclic RGD dimers with Gly3 and PEG4 linkers: promising agents for tumor integrin $\alpha v\beta 3$ PET imaging, Zhaofei Liu, Gang Niu, Jiyun Shi, Shuanglong Liu, Fan Wang, Shuang Liu, Xiaoyuan Chen, Eur J Nucl Med Mol Imaging (2009) 36:947-957; DOI 10.1007/s00259-008-1045-1
41. Evaluation of 111In-Labeled Cyclic RGD Peptides: Tetrameric not Tetravalent, Sudipta Chakraborty, Jiyun Shi, Young-Seung Kim, Yang Zhou, Bing Jia, Fan Wang, and Shuang Liu, *Bioconjugate Chem.* 2010, 21, 969-978.
42. Improving Tumor Uptake and Pharmacokinetics of 64Cu-Labeled Cyclic RGD Peptide Dimers with Gly3 and PEG4 Linkers, Jiyun Shi, Young-Seung Kim, Shizhen Zhai, Zhaofei Liu, Xiaoyuan Chen, and Shuang Liu, *Bioconjugate Chem.* 2009, 20, 750-759.
43. Improving Tumor-Targeting Capability and Pharmacokinetics of 99mTc-Labeled Cyclic RGD Dimers with PEG4 Linkers, Lijun Wang, Jiyun Shi, Young-Seung Kim, Shizhen Zhai, Bing Jia, Huiyun Zhao, Zhaofei Liu, Fan Wang, Xiaoyuan Chen, and Shuang Liu, VOL. 6, NO. 1, 231-245 MOLECULAR PHARMACEUTICS 2009.
44. Radiolabeled Cyclic RGD Peptides as Integrin rv_3-Targeted Radiotracers: Maximizing Binding Affinity via Bivalency, Shuang Liu, *Bioconjugate Chem., Vol.* 20, No. 12, 2009 2100-2213.
45. RGD Dendron Bodies; Synthetic Avidity Agents with Defined and Potentially Interchangeable Effector Sites That Can Substitute for Antibodies, Daniel Q. McNerny, Jolanta F. Kukowska-Latallo, Douglas G. Mullen, Joseph M. Wallace, Ankur M. Desai, Rameshwer Shukla, Baohua Huang, Mark M. Banaszak Holl, and James R. Baker, Jr., *Bioconjugate Chem.* 2009, 20, 1853-1859.
46. Synthesis of DOTA-Conjugated Multimeric [Tyr3]Octreotide Peptides via a Combination of Cu(I)-Catalyzed "Click" Cycloaddition and Thio Acid/Sulfonyl Azide "Sulfo-Click" Amidation and Their in vivo Evaluation, Cheng-Bin Yim, Ingrid Dijkgraaf, Remco Merkx, Cees Versluis, Annemarie Eek, Gwenn E. Mulder, Dirk T. S. Rijkers, Otto C. Boerman, and Rob M. J. Liskamp, J. Med. Chem. 2010, 53, 3944-3953.
47. Versatile Conjugation of Octreotide to Dendrimers by Cycloaddition ("Click") Chemistry to Yield High-Affinity Multivalent Cyclic Peptide Dendrimers, Cheng-Bin Yim, Otto C. Boerman, Monique de Visser, Marion de Jong, Annemarie C. Dechesne, Dirk T. S. Rijkers, and Rob M. J. Liskamp, *Bioconjugate Chem.* 2009, 20, 1323-1331.
48. Design, Synthesis, and Evaluation of Near Infrared Fluorescent Multimeric RGD Peptides for Targeting Tumors, Yunpeng Ye, Sharon Bloch, Baogang Xu, and Samuel Achilefu, *J. Med. Chem.* 2006, 49, 2268-2275.
49. Review: Cell-penetrating peptides and their therapeutic applications, Victoria Sebbage, Bioscience Horizons Volume 2 Number 1 March 2009 10.1093/biohorizons/hzp001 pp. 64-72.

50. Cell-penetrating peptides: from molecular mechanisms to therapeutics, May C. Morris, Sebastien Deshayes, Frederic Heitz and Gilles Divital Biol. Cell (2008) 100, 201-217; doi:10.1042/BC20070116.

51. Dynamic PET and Optical Imaging and Compartment Modeling using a Dual-labeled Cyclic RGD Peptide Probe, Lei Zhu, Ning Guo, Quanzheng Li, Ying Ma, Orit Jacboson, Seulki Lee, Hak Soo Choi, James R. Mansfield, Gang Niu, and Xiaoyuan Chen, Theranostics, 2012; 2(8): 746-756. doi: 10.7150/thno.4762.

Below are listed references for "A" as an antibody fragment, or other engineered proteins, which could benefit when they are used as the biologically active moiety, A, for the dPEG constructs disclosed herein, especially preferred when the "A"'s are used as "A" or as one or more of the embodiments in Davis, U.S. Pub. No. 2013/0052130, paragraphs (0209)-(0230).

52. SPECT and PET Imaging of EGF Receptors with Site-Specifically Labeled EGF and Dimeric EGF, Zoya Levashova, Marina V. Backer, George Horng, Dean Felsher, Joseph M. Backer, and Francis G. Blankenberg, *Bioconjugate Chem.* 2009, 20, 742-749.

53. Site-Specific Conjugation of Monodispersed DOTA-PEGn to a Thiolated Diabody Reveals the Effect of Increasing PEG Size on Kidney Clearance and Tumor Uptake with Improved 64-Copper PET Imaging, Lin Li, Desiree Crow, Fabio Turatti, James R. Bading, Anne-Line Anderson, Erasmus Poku, Paul J. Yazaki, Jenny Carmichael, David Leong, Michael P. Wheatcroft, Andrew A. Raubitschek, Peter J. Hudson, David Colcher, and John E. Shively; dx.doi.org/10.1021/bc100464e|*Bioconjugate Chem.*, 2011, 22 (4), pp. 709-716.

54. Nanobodies—the new concept in antibody engineering, Khalissa Deffar, Hengliang Shi, Liang Li, Xingzhi Wang and Xiaojuan Zhu, African Journal of Biotechnology Vol. 8 (12), pp. 2645-2652, 17 Jun., 2009.

54. Antibody fragments: Hope and hype, Aaron L. Nelson; mAbs 2:1, 77-83; January/February 2010;

55. Biotechnological applications of recombinant single-domain antibody fragments, Ario de Marco, Microbial Cell Factories 2011, 10:44.

56. Improved Tumor Targeting with Chemically Cross-Linked Recombinant Antibody Fragments', David J. King, Alison Turner, Andrew P. H. Farnsworth, John R. Adair, Raymond J. Owens, R. Barbara Pedley.

57. Beeley, Kenny Millar, T. Andrew Millican, Byron A. Boyce, Pan Antoniw, Andrew Mountain, Richard H. J. Begent, Dan Shochat, and Geoffrey T. Yarranton (CANCERRESEARCH54. 6176-6185. Dec. 1, 1994J.

58. Generation and Evaluation of Bispecific Affibody Molecules for Simultaneous Targeting of EGFR and HER2 Lina Ekerljung, Helena Wållberg, Azita Sohrabian, Karl Andersson, Mikaela Friedman, Fredrik Y Frejd, Stefan Ståhl, and Lars Gedda *Bioconjugate Chem.*, 2012, 23 (9), pp. 1802-1811.

59. HAHAHA, HEHEHE, HIHIHI or HKHKHK: influence of position and composition of histidine containing tags on biodistribution of [99mTc(CO)$_3$]+-labeled affibody molecules. Camilla Hofström, Mohamed Altai, Hadis Honarvar, Joanna Strand, Jennie Malmberg, Seyed Jalal Hosseinimehr, Anna Orlova, Torbjörn Gräslund, and Vladimir Tolmachev, *J. Med. Chem.*, DOI: 10.1021/jm400218y.

60. Use of a HEHEHE Purification Tag Instead of a Hexahistidine Tag Improves Biodistribution of Affibody Molecules Site-Specifically Labeled with $^{99m}$Tc, $^{111}$In, and $^{125}$I Camilla Hofström, Anna Orlova, Mohamed Altai, Fredrik Wångsell, Torbjörn Gräslund, and Vladimir Tolmachev, *J. Med. Chem.*, 2011, 54 (11), pp 3817-3826 DOI: 10.1021/jm200065e.

61. Evaluation of Four Affibody-Based Near-Infrared Fluorescent Probes for Optical Imaging of Epidermal Growth Factor Receptor Positive Tumors, Shibo Qi, Zheng Miao, Hongguang Liu, Yingding Xu, Yaqing Feng, and Zhen Cheng, *Bioconjugate Chem.*, 2012, 23 (6), pp. 1149-1156 DOI: 10.1021/bc200596a.

62. Influence of DOTA Chelator Position on Biodistribution and Targeting Properties of 111In-Labeled Synthetic Anti-HER2 Affibody Molecules, Anna Perols, Hadis Honarvar, Joanna Strand, Ramkumar Selvaraju, Anna Orlova, Amelie Eriksson Karlstro☐m, and Vladimir Tolmachev; dx.doi.org/10.1021/bc3002369|*Bioconjugate Chem.* 2012, 23, 1661-1670.

63. Evaluation of Maleimide Derivative of DOTA for Site-Specific Labeling of Recombinant Affibody Molecules, Sara Ahlgren, Anna Orlova, Daniel Rosik, Mattias Sandström, Anna Sjöberg, Barbro Baastrup, Olof Widmark, Gunilla Fant, Joachim Feldwisch, and Vladimir Tolmachev, *Bioconjugate Chem.* 2008, 19, 235-243.

64. Influence of nuclides and chelators on imaging using Affibody molecules: comparative evaluation of recombinant Affibody molecules site-specifically labeled with 68Ga and 111In via maleimido derivatives of DOTA and NODAGA. Mohamed Altai, Joanna Strand, Daniel Rosik, Ram Kumar Selvaraju.

65. Amelie Helen Eriksson Karlström, Anna Orlova, and Vladimir Tolmachev, *Bioconjugate Chem.*, Just Accepted Manuscript•DOI: 10.1021/bc300678y•Publication Date (Web): 24 May 2013.

66. Radiolabeled Affibody-Albumin Bioconjugates for HER2-Positive Cancer Targeting, Susan Hoppmann, Zheng Miao, Shuanglong Liu, Hongguang Liu, Gang Ren, Ande Bao, and Zhen Cheng, dx.doi.org/10.1021/bc100432h|*Bioconjugate Chem.* 2011, 22, 413-421. Engineering in functionality Options for "A" using the option of designing site-specific sites for doing biorthogonal chemistry using one or more, the same or different linear multifunctional linear dPEG constructs disclosed herein, but not limited to the following protein engineering options, both cell based and cell free based expression systems.

67. Adding New Chemistries to the Genetic Code, Chang C. Liu and Peter G. Schultz, Annu. Rev. Biochem., 79 (2010) 413-444.

68. Site-specifically chemical protein conjugation using genetically encoded aldehyde tags, Bertozzi, et al., Nature Protocols, 7 (2012) 1052-1067.

69. E. S. Zimmerman, et al., Bioconjugate Chemistry, 25 (2014) 351-361.

70. Antibody Engineering: Methods and Protocols, P. Chames, ed., 2$^{nd}$, Humana Press, 2012.

71. Cell-free synthetic biology: Thinking outside the cell, C. EricHodgman, MichaelC. Jewett, Hodgman, C. E., Jewett, M. C., Metab. Eng. (2011), doi:10.1016/j.ymben.2011.09.002.

72. Engineered protein scaffolds as next-generation antibody therapeutics, Michaela Gebauer and Arne Skerra, Current Opinion in Chemical Biology, 2009, 13:245-255.

"G" and references to options for radiolabels and chelators.

73. Targeted cancer therapy with a novel low-dose rate-emitting radioimmunoconjugate, Jostein Dahle, Jørgen Borrebk, Thora J. Jonasdottir, Anne Kristine Hjelmerud, Katrine B. Melhus, Øyvind S. Bruland, Oliver W. Press, and Roy H. Larsen, BLOOD, 15 Sep. 2007, VOLUME 110, NUMBER 6, pp. 2049-2056.
74. Cryptate Compounds and methods for Diagnosis and therapy, U.S. Pat. No. 6,869,589.
75. An improved synthesis and biological evaluation of a new cage-like bifunctional chelator, 4-((8-amino-3,6,10,13,16,19-hexaazabicyclo[6.6.6]icosane-1-ylamino) methyl)benzoic acid, for $^{64}$Cu radiopharmaceuticals, Hancheng Cai, Zibo Li, Chiun-Wei Huang, Ryan Park, Anthony H. Shahinian, Peter S. Conti, Nuclear Medicine and Biology 37 (2010) 57-65.
76. Biological Stability Evaluation of the R2β1 Receptor Imaging Agents: Diamsar and DOTA Conjugated DGEA Peptide, Chiun-Wei Huang, Zibo Li, Hancheng Cai, Tony Shahinian, and Peter S. Conti dx.doi.org/10.1021/bc100388g; Bioconjugate Chem. 2011, 22, 256-263.
77. Evaluation of Copper-64 Labeled AmBaSar Conjugated Cyclic RGD Peptide for Improved MicroPET Imaging of Integrin rv_3 Expression, Hancheng Cai, Zibo Li, Chiun-Wei Huang, Anthony H. Shahinian, Hui Wang, Ryan Park, and Peter S. Conti, Bioconjugate Chem. 2010, 21, 1417-1424.
78. Hexadentate Bispidine Derivatives as Versatile Bifunctional Chelate Agents for Copper(II) Radioisotopes, Stefanie Juran, Martin Walther, Holger Stephan, Ralf Bergmann, JoSteinbach, Werner Kraus, Franziska Emmerling, and Peter Comba Bioconjugate Chem. 2009, 20, 347-359 347
79. Synthesis of a novel bifunctional chelator AmBaSar based on sarcophagine for peptide conjugation and 64Cu radiolabelling, Hancheng Cai, John Fissekis and Peter S. Conti Dalton Trans., 2009, 5395-5400.
80. The Efficient Synthesis and Biological Evaluation of Novel Bi-Functionalized Sarcophagine for 64Cu Radiopharmaceuticals, Shuanglong Liu, Dan Li, Chiun-Wei Huang, Li-Peng Yap, Ryan Park, Hong Shan, Zibo Li1, Peter S. Conti, Theranostics, 2012; 2(6):589-596. doi: 10.7150/thno.4295.
81. Peter Conti, Cage-like Bifunctional chelators, Copper-64 Radiopharmaceuticals and PET Imaging using the same, US Pat. App. 2010/0196271 A1 Aug. 5, 2010.
82. Chemical and Radiochemical Considerations in Radiolabeling with alpha-Emitting Radionuclides, D. Scott Wilbur, Current Radiopharmaceuticals, 2011, 4, 214-247.
83. (Bimodal) First bodipy—DOTA derivatives as probes for bimodal imaging, Claire Bernhard, Christine Goze, Yoann Rousselin and Franck Denat, Chem. Commun., 2010, 46, 8267-8269.
84. (multi-NTAs) High-Affinity Adaptors for Switchable Recognition of Histidine-Tagged Proteins, Suman Lata, Annett Reichel, Roland Brock, Robert Tampa', and Jacob Piehler, J. AM. CHEM. SOC. 2005, 127, 10205-10215.
85. Stable and Functional Immobilization of Histidine-Tagged Proteins via Multivalent Chelator Headgroups on a Molecular Poly(ethylene glycol) Brush, Suman Lata and, Jacob Piehler, Analytical Chemistry 2005 77 (4), 1096-1105.
86. Specific and Stable Fluorescence Labeling of Histidine-Tagged Proteins for Dissecting Multi-Protein Complex Formation, Suman Lata, Martynas Gavutis, Robert Tampá, and Jacob Piehler, J. AM. CHEM. SOC. 2006, 128, 2365-2372.
87. Novel Polar Single Amino Acid Chelates for Technetium-99m Tricarbonyl-Based Radiopharmaceuticals with Enhanced Renal Clearance: Application to Octreotide, Kevin P. Maresca, John C. Marquis, Shawn M. Hillier, Genliang Lu, Frank J. Femia, Craig N. Zimmerman, William C. Eckelman, John L. Joyal, and John W. Babich, Bioconjugate Chem. 2010, 21, 1032-1042.
88. The Synthesis and Chelation Chemistry of DOTA-Peptide Conjugates, Luis M. De León-Rodriguez and Zoltan Kovacs, Bioconjugate Chem., Vol. 19, No. 2, 2008, 391-402.
89. Validation of a Novel CHX-A Derivative Suitable for Peptide Conjugation: Small Animal PET/CT Imaging Using Yttrium-86-CHX-A-Octreotide, Thomas Clifford, C. Andrew Boswell, Gráinne B. Biddlecombe, Jason S. Lewis, and Martin W. Brechbiel, J. Med. Chem. 2006, 49, 4297-4304.
90. Synthesis of Highly Iodinated Icosahedral Mono- and Dicarbon Carboranes, Rajiv R. Srivastava, Donald K. Hamlin, and D. Scott Wilbur, J. Org. Chem. 1996, 61, 9041-9044.
91. Reagents for Astatination of Biomolecules. 3. Comparison of closo-Decaborate(2-) and closo-Dodecaborate(2-) Moieties as Reactive Groups for Labeling with Astatine-211, D. Scott Wilbur, Ming-Kuan Chyan, Donald K. Hamlin, and Matthew A. Perry, Bioconjugate Chem. 2009, 20, 591-602.

In the present disclosure, A, AC and G can all be reactable. The current art is expanding its range of options and preferences are for these reactable groups, especially A for conjugating to a biologically active agent. The references listed below are ones representative of, but not limited to, the present art for the options of a reactable A or AC and G with the dPEG constructs disclosed herein.
92. Capture of Peptides with N-Terminal Serine and Threonine: A Sequence-Specific Chemical Method for Peptide Mixture Simplification, Dirk Chelius and Thomas A. Shaler, Bioconjugate Chem. 2003, 14, 205211.
93. New Cyclization Reaction at the Amino Terminus of Peptides and Proteins, Keith Rose, Jianhua Chen, Marina Dragovic, Weiguang Zeng, Damien Jeannerat, Philippe Kamalaprija, and Ulrich Burger, Bioconjugate Chem. 1999, 10, 1038-1043.
94. Synthesis of Peptide-Oligonucleotide Conjugates with Single and Multiple Peptides Attached to 2-Aldehydes through Thiazolidine, Oxime, and Hydrazine Linkages, Timofei S. Zatsepin, Dmitry A. Stetsenko, Andrey A. Arzumanov, Elena A. Romanova, Michael J. Gait, and Tatiana S. Oretskaya, Bioconjugate Chem. 2002, 13, 822830.
95. Review: α☐Oxo Aldehyde or Glyoxylyl Group Chemistry in Peptide Bioconjugation, Ouafa☐a El-Mandi and Oleg Melnyk; dx.doi.org/10.1021/bc300516f|Bioconjugate Chem. 2013, 24, 735-765.
96. Site-Specific One-Pot Dual Labeling of DNA by Orthogonal Cycloaddition Chemistry, Juliane Schoch, Markus Staudt, Ayan Samanta, Manfred Wiessler, and Andres Ja☐schke; dx.doi.org/10.1021/bc300181n|Bioconjugate Chem. 2012, 23, 1382-1386.
97. Sugars and proteins: New strategies in synthetic biology, Benjamin G. Davis Pure Appl. Chem., Vol. 81, No. 2, pp. 285-298, 2009.
98. Enzymatic Deglutathionylation to Generate Interleukin-4 Cysteine Muteins with Free Thiol, Viswanadham Duppatla, Maja Gjorgjevikj, Werner Schmitz, Mathias Kottmair, Thomas D. Mueller, and Walter Sebald; dx.doi.org/10.1021/bc2004389|Bioconjugate Chem. 2012, 23, 1396-1405.
99. Introducing Bioorthogonal Functionalities into Proteins in Living Cells, ZIYANG HAO, SENLIAN HONG, XING CHEN, AND PENG R. CHEN ACCOUNTS OF CHEMICAL RESEARCH, 742-751, 2011, Vol. 44, No. 9.

100. A "Tag-and-Modify" Approach to Site-Selective Protein Modification, JUSTIN M. CHALKER, GONC-ALO J. L. BERNARDES, AND BENJAMIN G. DAVIS, ACCOUNTS OF CHEMICAL RESEARCH, 730-741, 2011, Vol. 44, No. 9.

101. An integrated cell-free metabolic platform for protein production and synthetic biology, Michael C Jewett, Kara A Calhoun, Alexei Voloshin, Jessica J Wuu and James R Swartz, Molecular Systems Biology, 4; Article number 220; doi:10.1038/msb.2008.57.

102. Engineering of Aerococcus viridans L-Lactate Oxidase for Site-Specific PEGylation: Characterization and Selective Bioorthogonal Modification of a S218C Mutant, Birgit Unterweger, Thomas Stoisser, Stefan Leitgeb, Ruth Birner-Gru☐nberger, and Bernd Nidetzky; dx.doi.org/10.1021/bc2006847|Bioconjugate Chem. 2012, 23, 1406-1414.

103. A New Method to Produce MonoPEGylated Dimeric Cytokines Shown with Human Interferon-r2b, Chien-Hsing Chang, Edmund A. Rossi, Thomas M. Cardillo, Diane L. Nordstrom, William J. McBride, and David M. Goldenberg, *Bioconjugate Chem.* 2009, 20, 1899-1907.

104. Bioorthogonal Chemistry: Fishing for Selectivity in a Sea of Functionality, Ellen M. Sletten and Carolyn R. Bertozzi, Angew. Chem. Int. Ed. 2009, 48, 6974-6998.

105. (Cores) Dendrimers Derived from 1 f 3 Branching Motifs, George R. Newkome and Carol Shreiner, *Chem. Rev.* 2010, 110, 6338-6442.

106. Strain-Promoted Alkyne Azide Cycloaddition for the Functionalization of Poly(amide)-Based Dendrons and Dendrimers, Cá tia Ornelas, Johannes Broichhagen, and Marcus Weck, J. AM. CHEM. SOC. 2010, 132, 3923-3931.

107. A Biocompatible Condensation Reaction for the Labeling of Terminal Cysteine Residues on Proteins, Hongjun Ren, Fei Xiao, Ke Zhan, Young-Pil Kim, Hexin Xie, Zuyong Xia, and Jianghong Rao, Angew. Chem. Int. Ed. 2009, 48, 9658-9662.

108. Genetically Encoded 1,2-Aminothiols Facilitate Rapid and Site-Specific Protein Labeling via a Bioorthogonal Cyanobenzothiazole Condensation, Duy P. Nguyen, Thomas Elliott, Matthew Holt, Tom W. Muir, and Jason W. Chin; dx.doi.org/10.1021/ja203111c|J. Am. Chem. Soc. 2011, 133, 11418-11421.

109. A biocompatible condensation reaction for controlled assembly of nanostructures in living cells, Gaolin Liang, Hongjun Ren and Jianghong Rao, NATURE CHEMISTRY|VOL 2|JANUARY 54 2010 *Nature Chemistry* 2, 54-60 (2010); published online 17 Dec. 2009.

110. Application of Strain-Promoted Azide-Alkyne Cycloaddition and Tetrazine Ligation to Targeted Fc-Drug Conjugates, Joshua D. Thomas, Huiting Cui, Patrick, J. North, Thomas Hofer, Christoph Rader, and Terrence R. Burke, Jr.; dx.doi.org/10.1021/bc300052u|Bioconjugate Chem. 2012, 23, 2007-2013.

111. Modular Strategy for the Construction of Radiometalated Antibodies for Positron Emission Tomography Based on Inverse Electron Demand Diels-Alder Click Chemistry, Brian M. Zeglis, Priya Mohindra, Gabriel I. Weissmann, Vadim Divilov, Scott A. Hilderbrand, Ralph Weissleder, and Jason S. Lewis; dx.doi.org/10.1021/bc200288d|Bioconjugate Chem. 2011, 22, 2048-2059.

112. Synthesis and Evaluation of a Series of 1,2,4,5-Tetrazines for Bioorthogonal Conjugation, Mark R. Karver, Ralph Weissleder, and Scott A. Hilderbrand; dx.doi.org/10.1021/bc200295y|Bioconjugate Chem. 2011, 22, 2263-2270

113. Tetrazine-Based Cycloadditions: Application to Pretargeted Live Cell Imaging, Neal K. Devaraj, Ralph Weissleder, and Scott A. Hilderbrand, *Bioconjugate Chem.* 2008, 19, 2297-2299.

114. Dimensional Imaging of Living Cells, Jan Dommerholt, Samuel Schmidt, Rinske Temming, Linda J. A. Hendriks, Floris P. J. T. Rutjes, Jan C. M. van Hest, Dirk J. Lefeber, Peter Friedl, and Floris L. van Delft, Angew. Chem. Int. Ed. 2010, 49, 9422-9425.

115. Genetic Encoding of a Bicyclo[6.1.0]nonyne-Charged Amino Acid Enables Fast Cellular Protein Imaging by Metal-Free Ligation, Annika Borrmann, Sigrid Milles, Tilman Plass, Jan Dommerholt, Jorge M. M. Verkade, Manfred Wießler, Carsten Schultz, Jan C. M. van Hest, Floris L. van Delft, and Edward A. Lemke; DOI: 10.1002/cbic.201200407.

116. Recent applications of thiol-ene coupling as a click process for glycoconjugation, Dondoni, A.; Marra, A. *Chem. Soc. Rev.* 2012, 41, 573-586

117. Thiol-Ene Click Chemistry, Charles E. Hoyle[†] and Christopher N. Bowman Angew. Chem. Int. Ed. 2010, 49, 1540-1573, Cu-free click cycloaddition reactions in chemical biology, John C. Jewetta and Carolyn R. Bertozzi, Chem. Soc. Rev., 2010, 39, 1272-1279.

In all of the preferred embodiments disclosed herein, the option for having the wavy line, ∼∼∼∼, incorporate a cleavable option, especially when the application with "A" and "G" being for is a therapeutic and where "G" is a therapeutic agent, preferably a drug, that when released within the cell would be a more effect therapeutic agent. Listed below are some references, but not limited to the options of the type of cleavable options that can be part of the wavy line, ∼∼∼∼, in the preferred embodiments of the dPEG constructs disclosed herein.

118. Lysosomal Enzyme-cleavable Anti-tumor Drug Conjugates, Firestone, U.S. Pat. No. 6,214,345.

119. Heterocyclic Self-immolative Linkers and Conjugates, Feng, U.S. Pat. No. 7,989,434.

120. Hydrazone, Amide, Carbamate, Macromolecular and Other Prodrugs of Doxorubicin, Sevim Rollas and Güniz, *The Open Drug Delivery Journal*, 2008, 2, 77-85.

121. Function and Stability of Abscisic Acid Acyl Hydrazone Conjugates by LC-MS2 of ex Vivo Samples, Timothy R. Smith, Andrew J. Clark, Richard Napier, Paul C. Taylor, Andrew J. Thompson, and Andrew Marsh, Bioconjugate Chem. 2007, 18, 13551359.

122. Hydrolytic Stability of Hydrazones and Oximes, Jeet Kalia and Ronald T. Raines, Angew. Chem. Int. Ed. 2008, 47, 7523-7526.

Listed below are representative references for where "A" is a nanoparticle.

123. APPLICATIONS OF LIPOSOMES IN MEDICINE—A REVIEW, Deepak. G. Umalkar, Dr. K S. Rajesh, Ganesh S. Bangale, B. Stephen Rathinaraj, Gajanan. V. Shinde, Preetha S. Panicker PHARMA SCIENCE MONITOR Vol-2, Issue-2, 2011 ISSN: 0976 pp. 24-39.

124. (example where discrete PEG would give much better control) Dual-ligand modification of PEGylated liposomes shows better cell selectivity and efficient gene delivery, Kibria, Golam; Hatakeyama, Hiroto; Ohga, Noritaka; Hida, Kyoko; Harashima, Hideyoshi, Journal of Controlled Release, 153(2): 141-148, Issue Date 2011-07-30.

125. Enhanced solubility and stability of PEGylated liposomal paclitaxel: In vitro and in vivo evaluation, Tao Yang, Fu-De Cui, Min-Koo Choi, Jei-Won Choc, Suk-Jae Chung, Chang-Koo Shim, Dae-Duk Kim, International Journal of Pharmaceutics, 338 (2007) 317-326.
126. Peptide-modified liposomes for selective targeting of bombesin receptors overexpressed by cancer cells: a potential theranostic agent, Antonella Accardo, Giuseppina Salsano, Anna Morisco, Michela Aurilio, Antonio Parisi, Francesco Maione, Carla Cicala, Diego Tesauro, Luigi Aloj, Giuseppe De Rosa, Giancarlo Morelli, International Journal of Nanomedicine 2012:7 2007-2017.
127. Optimizing Druggability through Liposomal Formulations: New Approaches to an Old Concept, Dimitrios Bitounis, Raphaelle Fanciullino, Athanassios Iliadis, and Joseph Ciccolini ISRN Pharmaceutics, Volume 2012, Article ID 738432, 11 pages; doi:10.5402/2012/738432.
128. Preparation of RGD-modified Long Circulating Liposome Loading Matrine and its in vitro Anti-cancer Effects, Xiao-yan Liu, Li-ming Ruan, Wei-wei Mao, Jin-Qiang Wang, You-qing Shen, Mei-hua Sui *International Journal of Medical Sciences,* 2010; 7(4):197-208.
129. Solid-Phase Synthesis of PEGylated Lipopeptides Using Click Chemistry Rasmus I. Jølck, Rolf H. Berg, and Thomas L. Andresen, *Bioconjugate Chem.* 2010, 21, 807-810.
130. Stealth liposomes and long circulating nanoparticles: critical issues in pharmacokinetics, opsonization and protein-binding properties, S. M. Moghimia, J. Szebenib, Progress in Lipid Research 42 (2003) 463-478.
131. Stealth liposomes: review of the basic science, rationale, and clinical applications, existing and Potential Maria Laura Immordino, Franco Dosio, Luigi Cattel, International Journal of Nanomedicine 2006:1(3) 297-315.
132. A Systematic Analysis of Peptide Linker Length and Liposomal Polyethylene Glycol Coating on Cellular Uptake of Peptide-Targeted Liposomes, Jared F Stefanick, Jonathan D Ashley, Tanyel Kiziltepe, and Basar Bilgicer, *ACS Nano,* DOI: 10.1021/nn305663e•Publication Date (Web): 19 Feb. 2013, VOL. 7, NO. 4, 2935-2947, 2013.
133. Multimodal silica nanoparticles are effective cancer-targeted probes in a model of human melanoma, Benezra, et al., J. Clin. Invest., doi:10.1172/JCI45600
134. Miriam Benezra, Oula Penate-Medina, Pat B. Zanzonico, David Schaer, Hooisweng Ow, Andrew Burns, Elisa DeStanchina, Valerie Longo, Erik Herz, Srikant Iyer, Jedd Wolchok, Steven M. Larson, Ulrich Wiesner, and Michelle S. Bradbury, *J Clin Invest* doi:10.1172/JCI45600. Pp. 1-13.
135. Antibody-Maytansinoid Conjugates Designed to Bypass Multidrug Resistance Yelena V. Kovtun, Charlene A. Audette, Michele F. Mayo, Gregory E. Jones, Heather Doherty, Erin K. Maloney, Hans K. Erickson, Xiuxia Sun, Sharon Wilhelm, Olga Ab, Katharine C. Lai, Wayne C. Widdison, Brenda Kellogg, Holly Johnson, Jan Pinkas, Robert J. Lutz, Rajeeva Singh, Victor S. Goldmacher, and Ravi V. J. Chari Cancer Res; 70(6); 2528-37.
136. Cyclic RGD Functionalized Gold Nanoparticles for Tumor Targeting, Daniela Arosio, Leonardo Manzoni, Elena M. V. Araldi, and Carlo Scolastico; dx.doi.org/10.1021/bc100448r|Bioconjugate Chem. 2011, 22, 664-672
137. Design and Synthesis of Multifunctional Gold Nanoparticles Bearing Tumor-Associated Glycopeptide Antigens as Potential Cancer Vaccines, Raymond P. Brinãs, Andreas Sundgren, Padmini Sahoo, Susan Morey, Kate Rittenhouse-Olson, Greg E. Wilding, Wei Deng, and Joseph J. Barchi, Jr.; dx.doi.org/10.1021/bc200606s|Bioconjugate Chem.
138. Short-Chain PEG Mixed Monolayer Protected Gold Clusters Increase Clearance and Red Blood Cell Counts, Carrie A. Simpson, Amanda C. Agrawal, Andrzej Balinski, Kellen M. Harkness, and David E. Cliffel ACSNano, VOL. 5, NO. 5, 3577-3584, 2011.
139. Bombesin functionalized gold nanoparticles show in vitro and in vivo cancer receptor specificity, Nripen Chanda, Vijaya Kattumuri, Ravi Shukla, Ajit Zambre, Kavita Kattia, Anandhi Upendran, Rajesh R. Kulkarnia, Para Kane, Genevieve M. Fent, Stan W. Casteel, C. Jeffrey Smith, Evan Boote, J. David Robertson, Cathy Cutlerd, John R. Levera, Kattesh V. Katti, and Raghuraman Kannan 8760-8765|PNAS|May 11, 2010|vol. 107|no. 19.
140. Multiple thiol-anchor capped DNA-gold nanoparticle conjugates, Nucleir Addicts Research, 2002, 30(7), 1558-1562 Zhi Li, Rongchao Jin, Chad A. Mirkin and Robert L. Letsinger.
141. Synthesis, Stability, and Cellular Internalization of Gold Nanoparticles Containing Mixed Peptide-Poly(ethylene glycol) Monolayers, Yanli Liu, Mathew K. Shipton, Joseph Ryan, Eric D. Kaufman, Stefan Franzen, and Daniel L. Feldheim Anal. Chem. 2007, 79, 2221-2229.
142. Transferrin-Mediated Gold Nanoparticle Cellular Uptake, Pei-Hui Yang, Xuesong Sun, Jen-Fu Chiu, Hongzhe Sun, and Qing-Yu He, Bioconjugate Chem. 2005, 16, 494-496.
143. Conjugation of Peptides to the Passivation Shell of Gold Nanoparticles for Targeting of Cell-Surface Receptors, Lisa Maus, Oliver Dick, Hilmar Bading, Joachim P. Spatz, and Roberto Fiammengo, ACSNano, VOL. 4■NO. 11■6617-6628■2010.

Nomenclature of disclosed dPEG constructs herein is the same as that defined in Davis, U.S. Pub. No. 20130052130, paragraphs (0096)-(0102).

The schemes shown in equations below are general or representative methods for and specific examples of building the preferred embodiments of the disclosed dPEG constructs like,

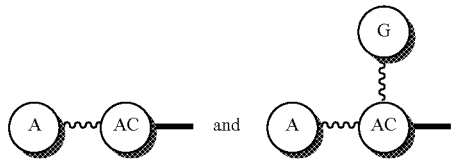

and, various specific embodiments of

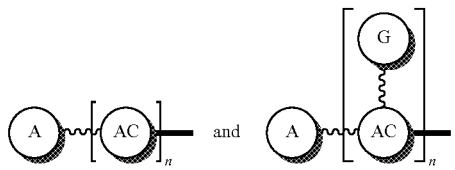

including

-continued

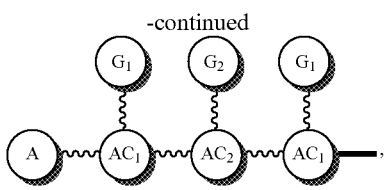

A key to enabling making substantial pure compounds of these embodiments is the ability to make the individual solid, ——, and wavy line, ∼∼∼, components of each embodiment (Davis, U.S. Pat. Nos. 7,888,536 and 8,637,711). The specific options for optimal design of method can be drawn from the extensive art for building peptides and related art.

In the first case of

shown are two different approaches. These could be used if optimizing for either the solid line, ——, from

or the wavy line, ∼∼∼, from

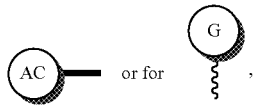

when it is a diagnostic or therapeutic. (Note: Technically in the examples, we are modifying AC.)

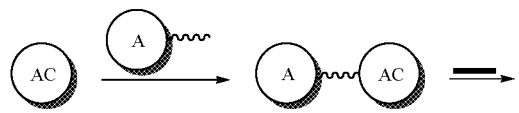

-continued

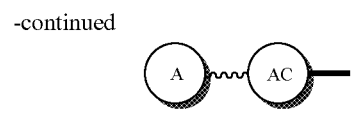

and

Alternatively,

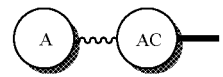

Optionally, AC can be changed in order to accommodate various

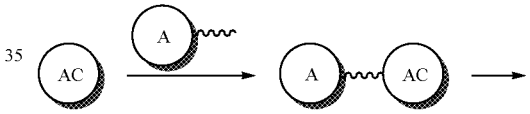's.

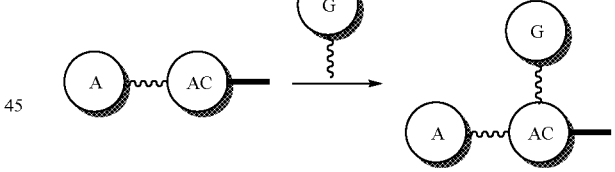

Shown below is a case where the solid line, is varied with for two dPEG lengths of 12 and 24 ethylene oxide units, and to the final AC, which is an active TFP ester, now can be added a diagnostic or a therapeutic that is an amine.

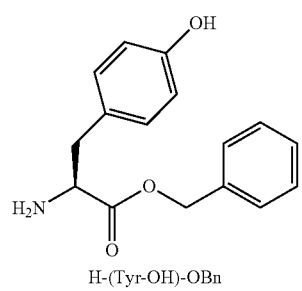 + 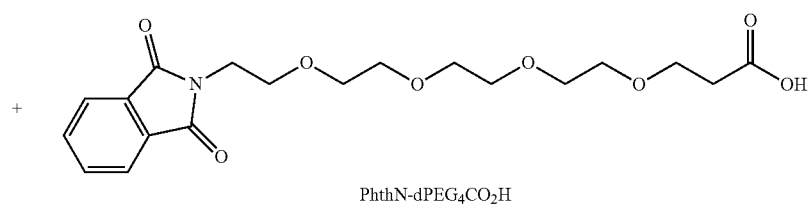

H-(Tyr-OH)-OBn     PhthN-dPEG4CO2H

-continued
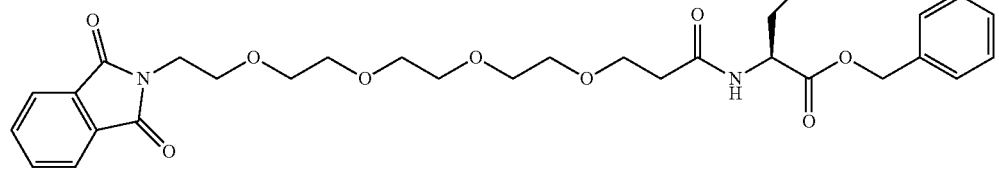
PhthN-dPEG₄(Tyr-OH)-OBn
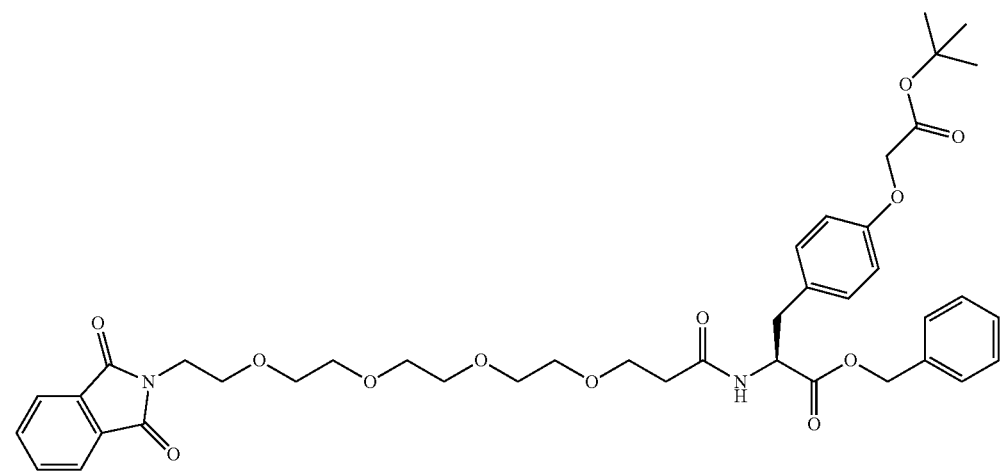
PhthN-dPEG₄(Tyr-OTBA)-OBn
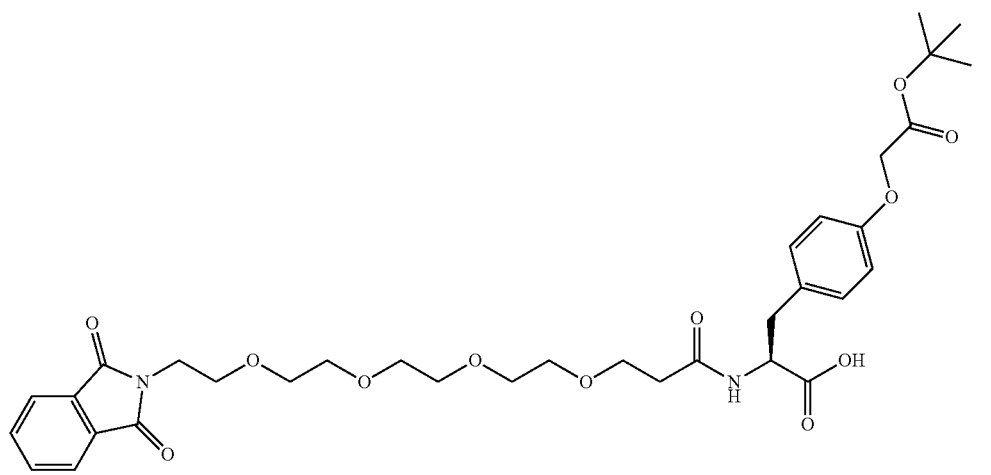
PhthN-dPEG₄(Tyr-OTBA)-OH
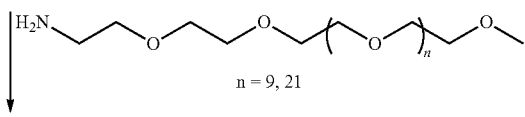
n = 9, 21

-continued
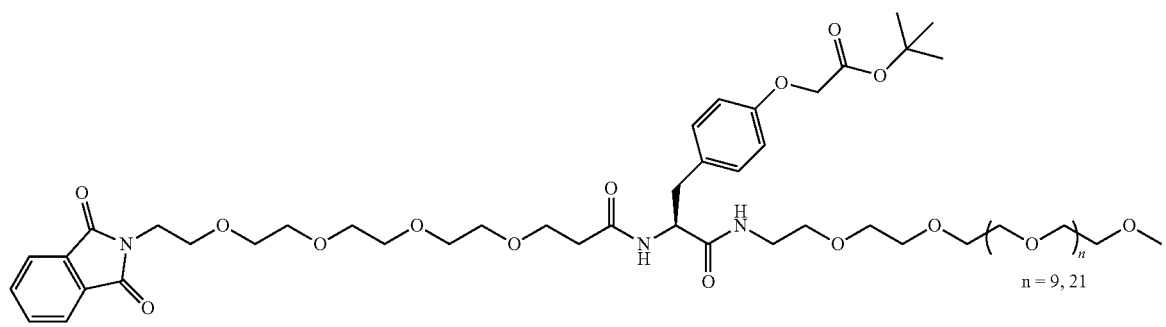
PhthN-dPEG₄(Tyr-OTBA)-NH-m-dPEG₁₂/₂₄
PhthN-dPEG₄(Tyr-OTBA)-NH-m-dPEG₁₂/₂₄
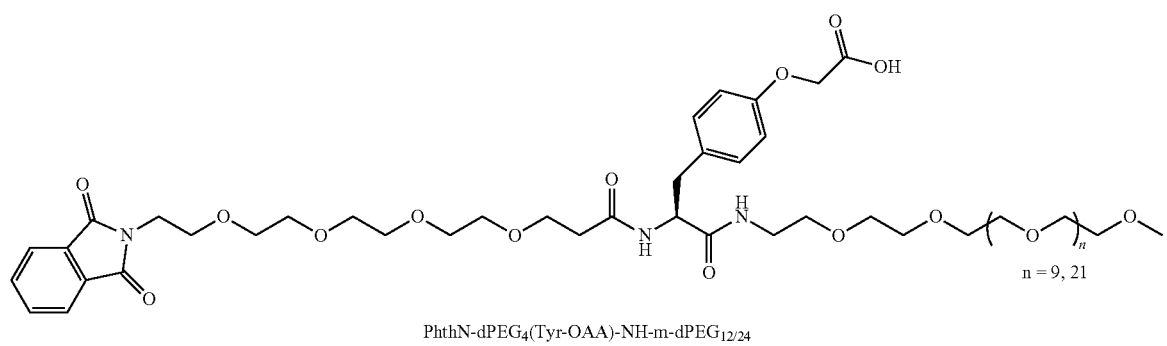
PhthN-dPEG₄(Tyr-OAA)-NH-m-dPEG₁₂/₂₄
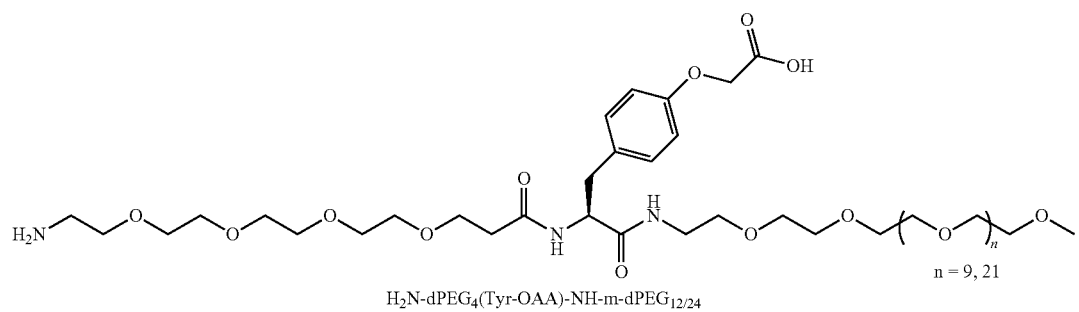
H₂N-dPEG₄(Tyr-OAA)-NH-m-dPEG₁₂/₂₄
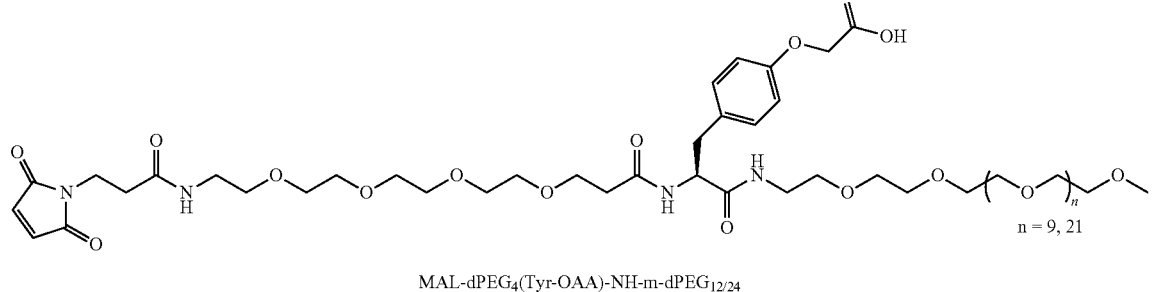
MAL-dPEG₄(Tyr-OAA)-NH-m-dPEG₁₂/₂₄

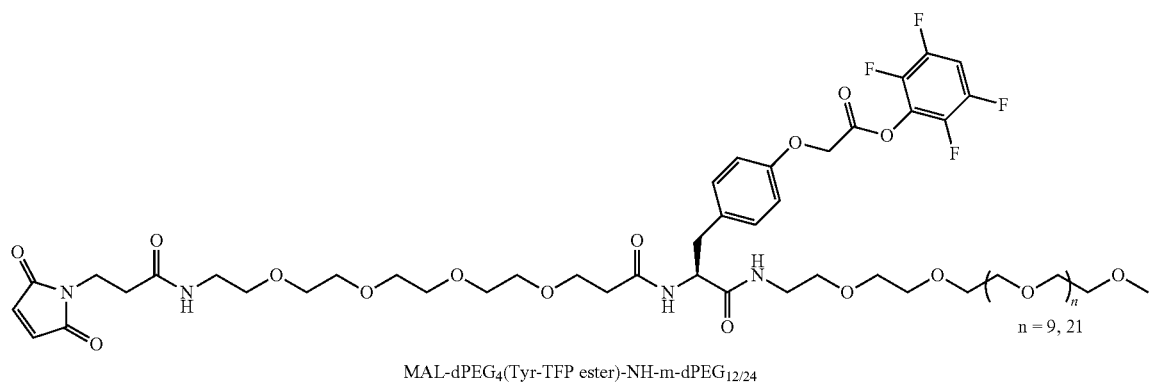

MAL-dPEG₄(Tyr-TFP ester)-NH-m-dPEG₁₂/₂₄

As the free acid, these could either be directly coupled to the amide or to an ester. The phenol of the tyrosine is a preferred AC in many cases as the functionality of the AC can be modified simply to a range of the same, as shown for

Above, the A is an amine protected as the phthalimide, while presently the A is protected as the t-boc. The protecting group as part of A can vary as the compatible chemistry demands or provides a range of options.

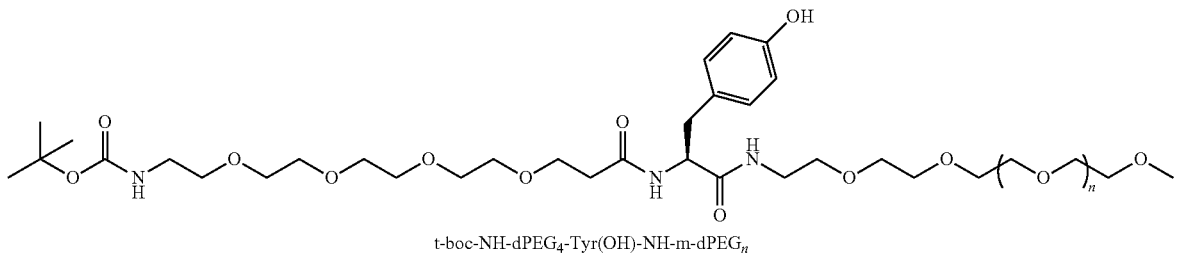

t-boc-NH-dPEG₄-Tyr(OH)-NH-m-dPEGₙ

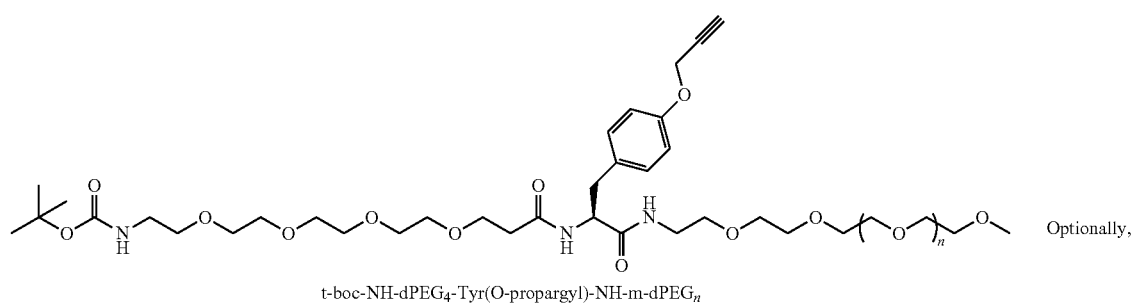

t-boc-NH-dPEG₄-Tyr(O-propargyl)-NH-m-dPEGₙ

Optionally,

-continued
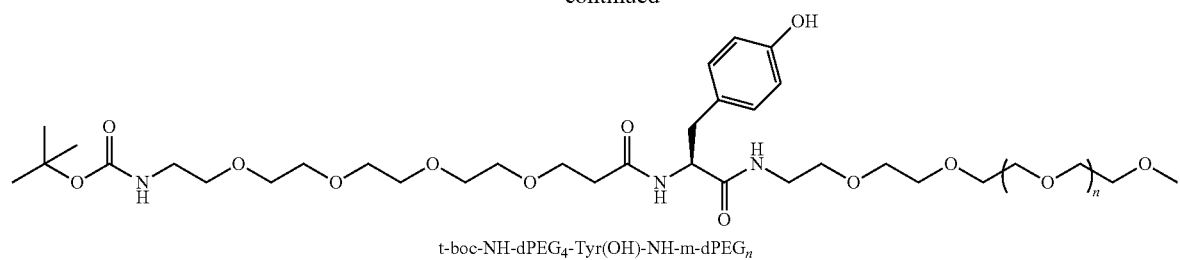
t-boc-NH-dPEG₄-Tyr(OH)-NH-m-dPEGₙ
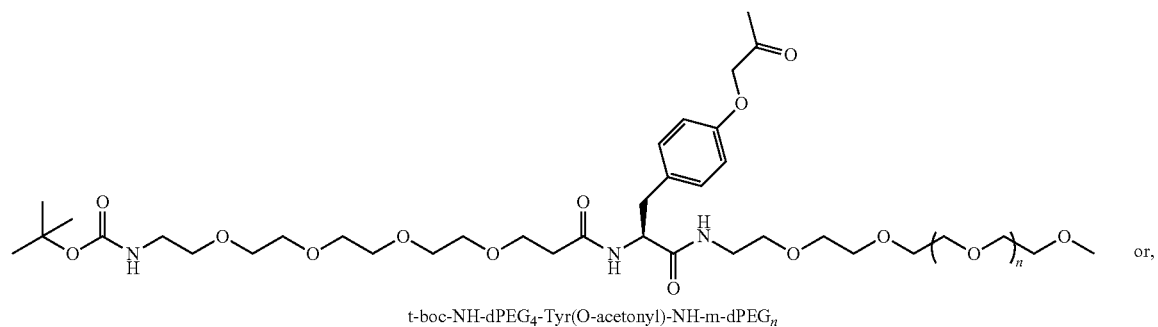
t-boc-NH-dPEG₄-Tyr(O-acetonyl)-NH-m-dPEGₙ    or,
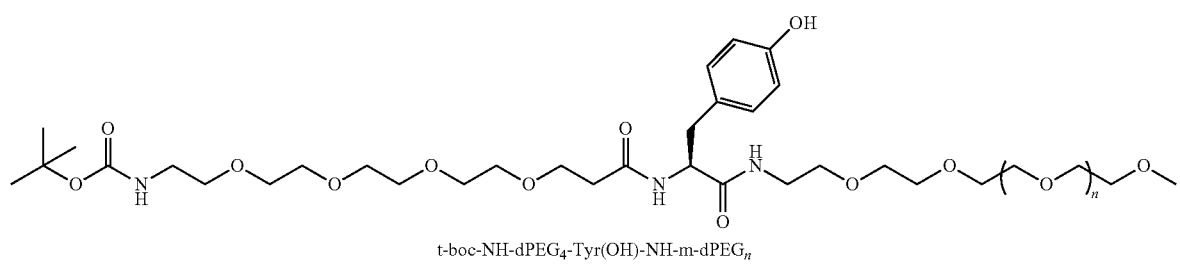
t-boc-NH-dPEG₄-Tyr(OH)-NH-m-dPEGₙ
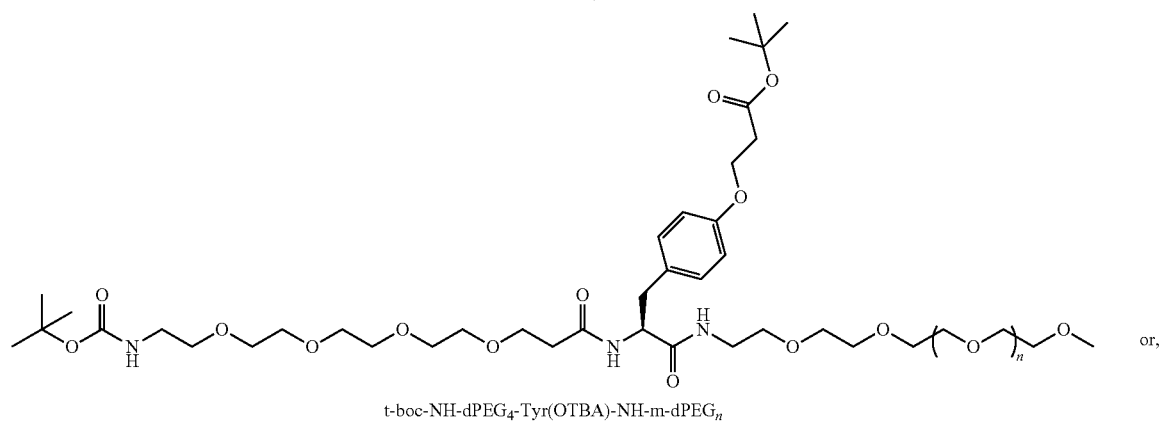
t-boc-NH-dPEG₄-Tyr(OTBA)-NH-m-dPEGₙ    or,
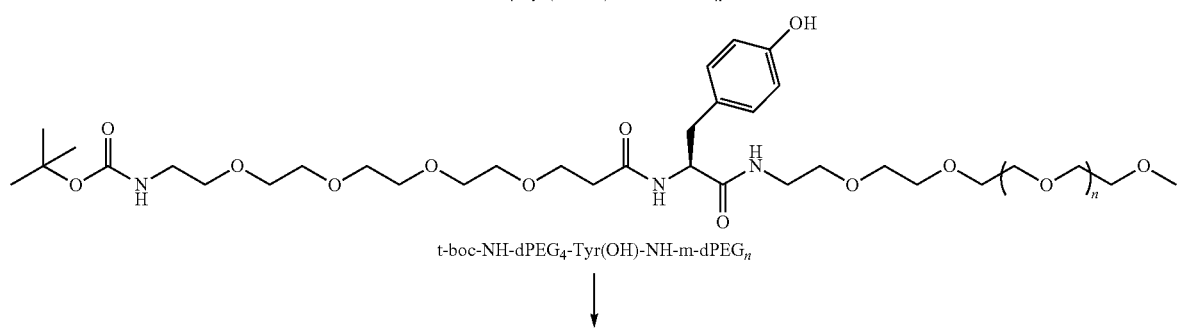
t-boc-NH-dPEG₄-Tyr(OH)-NH-m-dPEGₙ

-continued
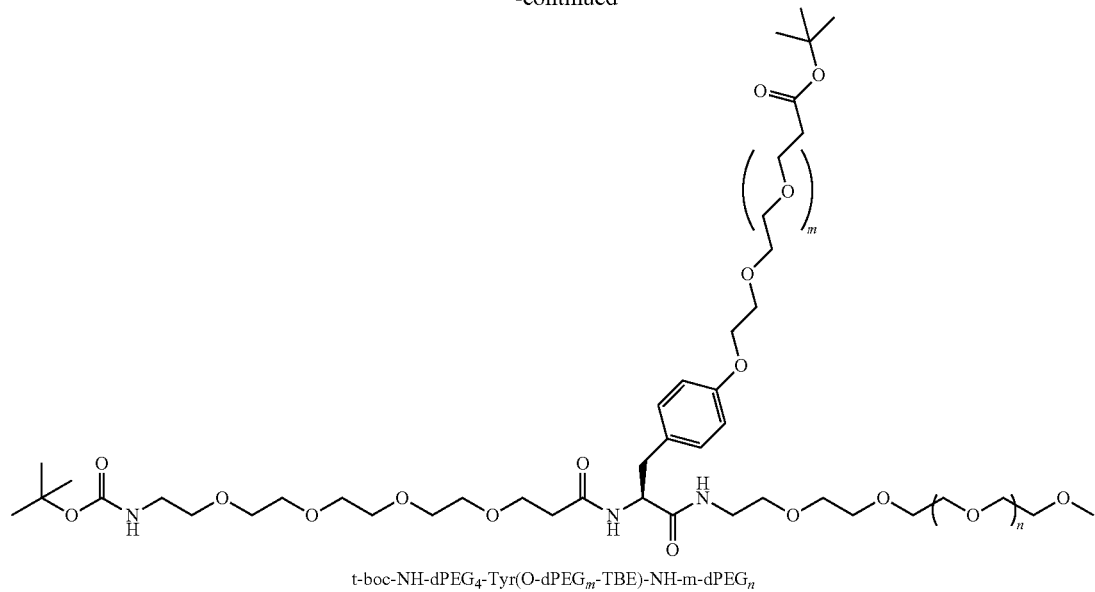
t-boc-NH-dPEG$_4$-Tyr(O-dPEG$_m$-TBE)-NH-m-dPEG$_n$
25
Also, shown below are constructs that show the solid line as with an amide linkage in the dPEG chain, as well as a solid line with a negatively charged terminal group.
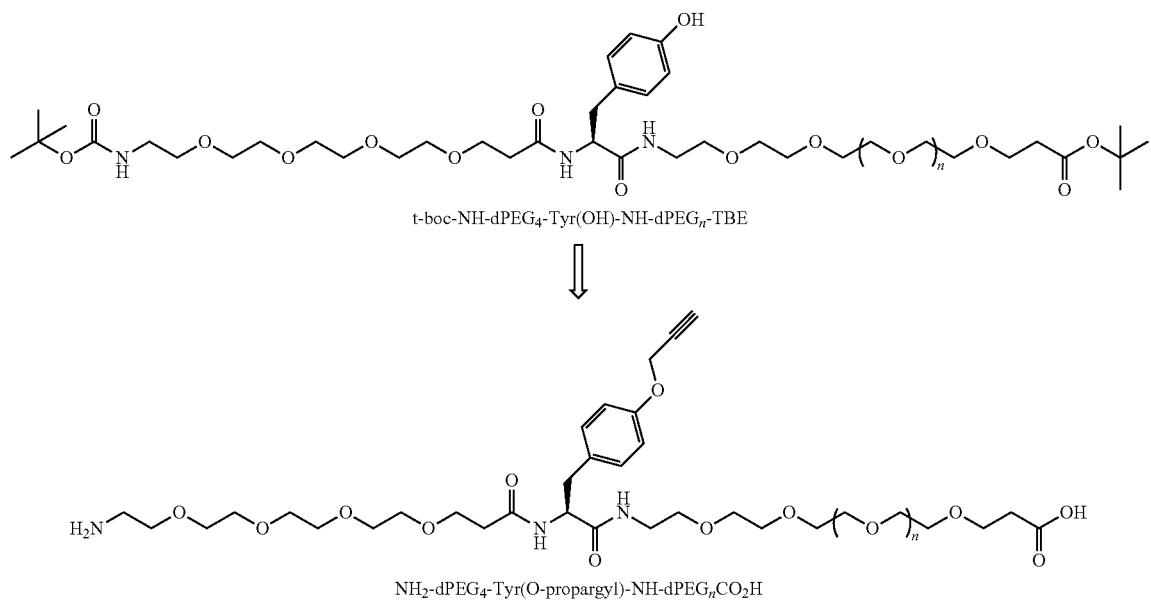
t-boc-NH-dPEG$_4$-Tyr(OH)-NH-dPEG$_n$-TBE
⇓
NH$_2$-dPEG$_4$-Tyr(O-propargyl)-NH-dPEG$_n$CO$_2$H
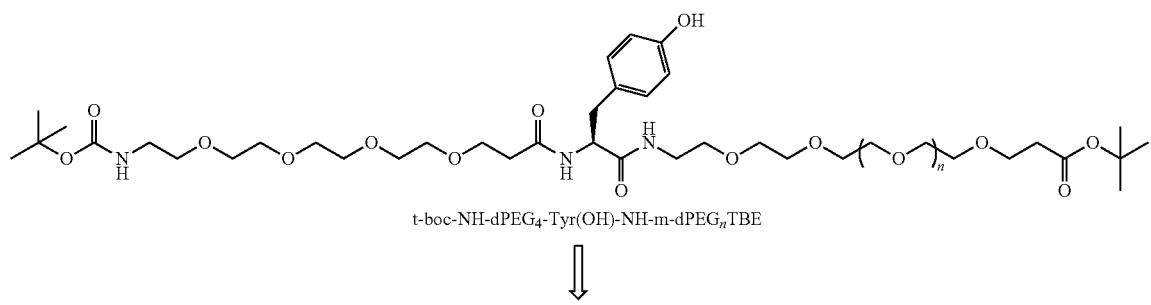
t-boc-NH-dPEG$_4$-Tyr(OH)-NH-m-dPEG$_n$TBE
⇓

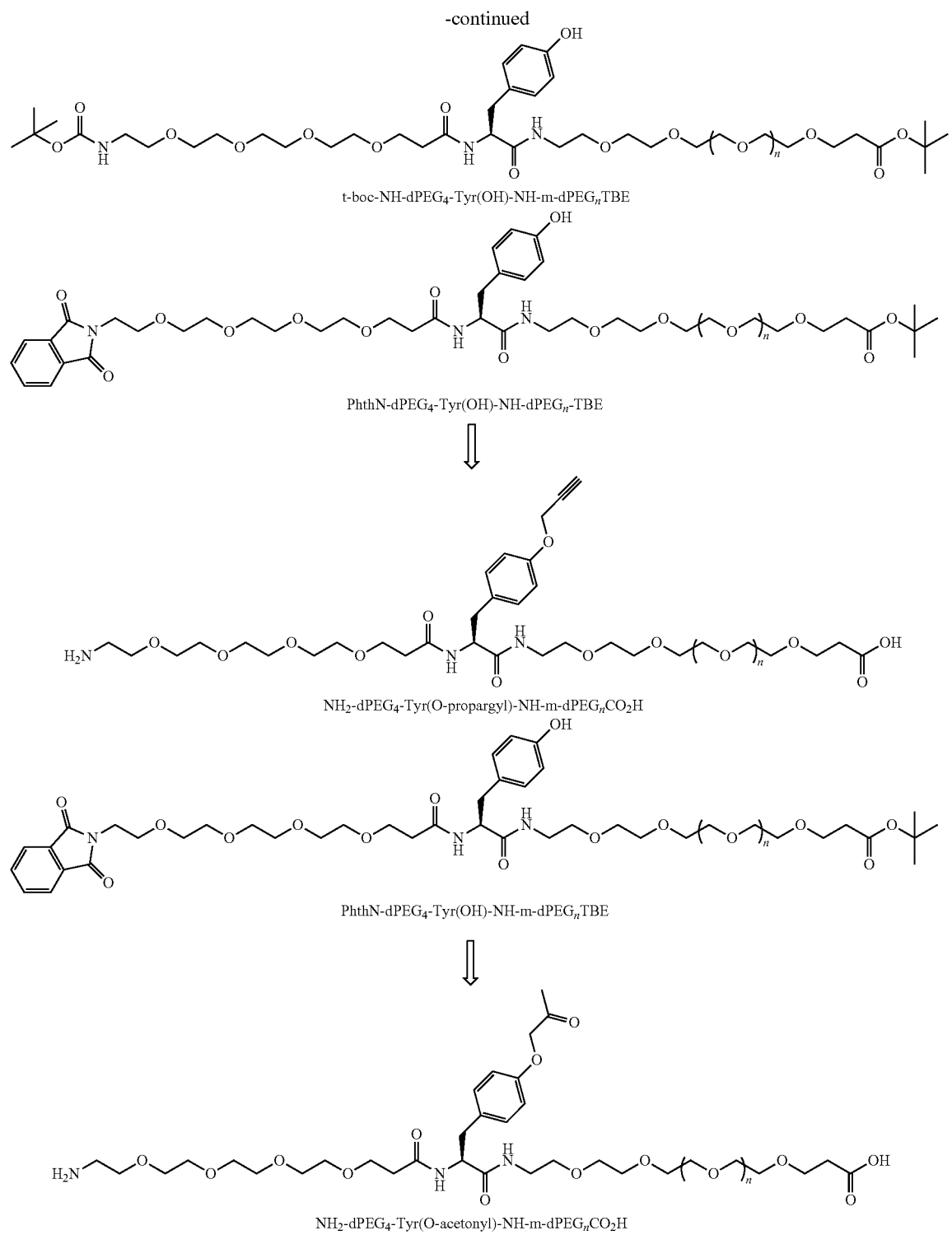

Currently in the art, the reactable A is a maleimide, and the reactable G is an amine reactable active ester, but the options for combinations in this simple preferred embodiment can be expanded into options like, but not limited to those disclosed in paragraphs (0102) and (0103) in Davis, U.S. Pub. No. 2013/0052130, Tables 1 and 2.

With this currently preferred combination in ADC (antibody-drug conjugate) design, below are some examples of where G is either a diagnostic or therapeutic. In the case of the DOTA, this can be chelated with a variety of radionuclides, other amine dyes than carboxyfluorescien are optional, like the various Alexa, Dylight and Cy dyes, visible and NIR, and other related dyes known in the art. The reaction with the doxorubicin is just an example of most of the drugs currently uses as toxic payloads in ADCs are presented to the chemical construct as an amine derivative.

51                                                                 52
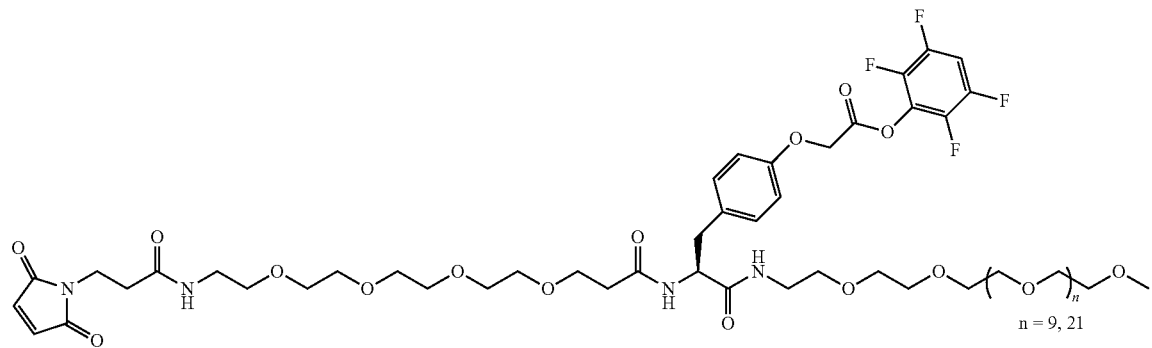
MAL-dPEG₄(Tyr-TFP ester)-NH-m-dPEG₁₂/₂₄
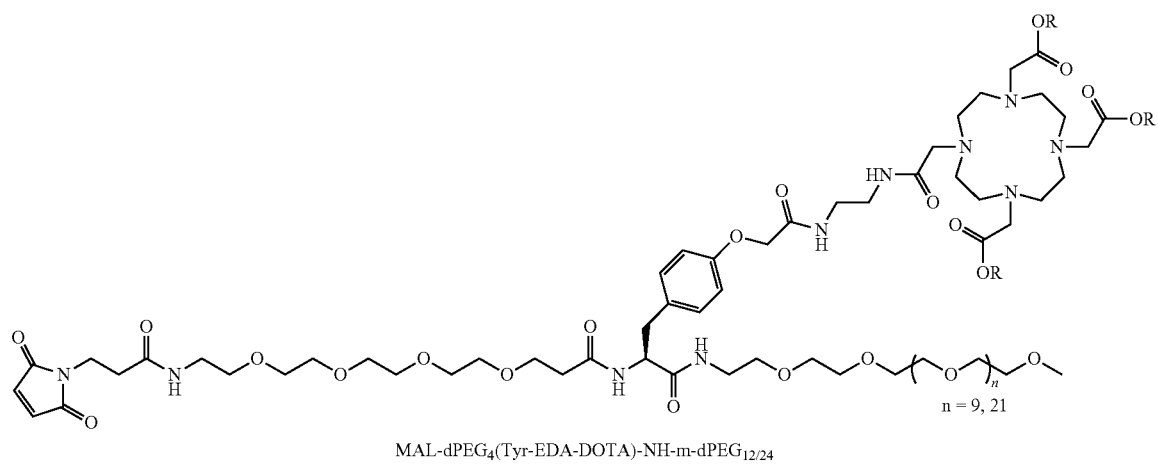
MAL-dPEG₄(Tyr-EDA-DOTA)-NH-m-dPEG₁₂/₂₄
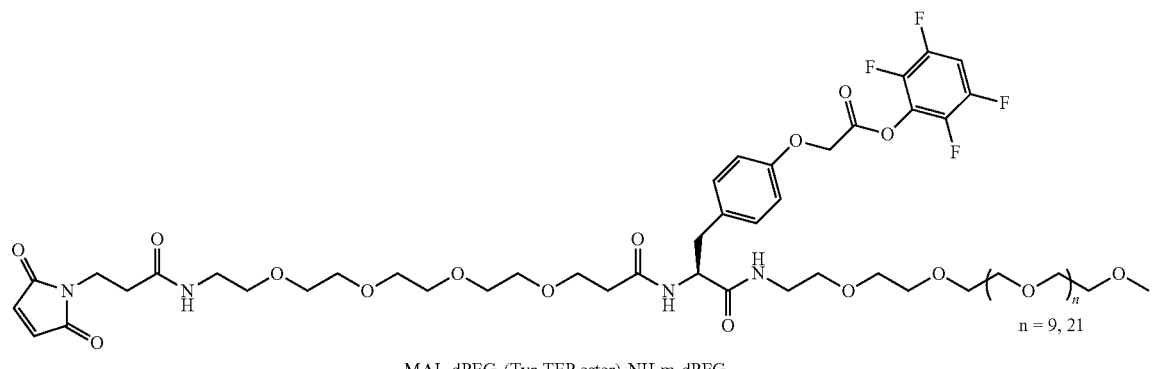
MAL-dPEG₄(Tyr-TFP ester)-NH-m-dPEG₁₂/₂₄

-continued
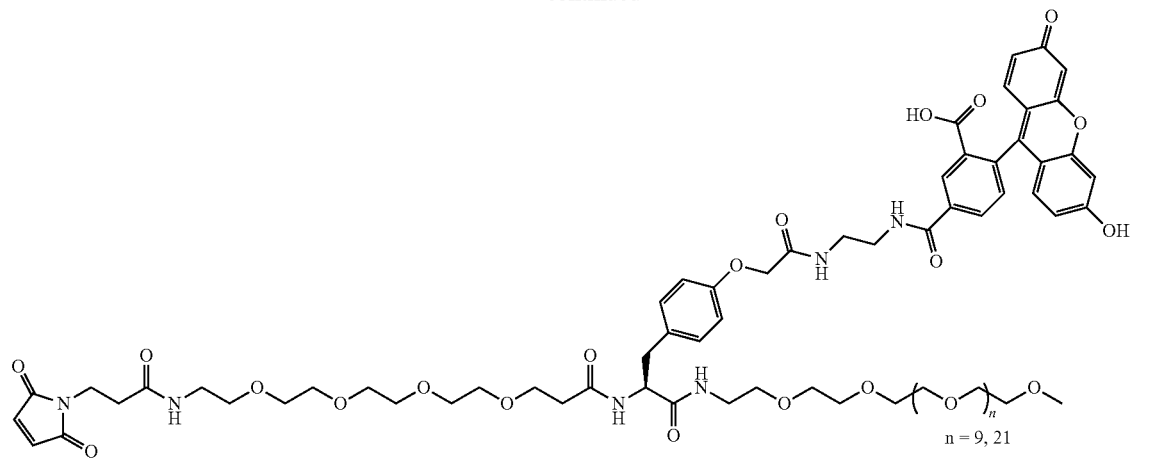
MAL-dPEG₄(Tyr-EDA-CF)-NH-m-dPEG₁₂/₂₄
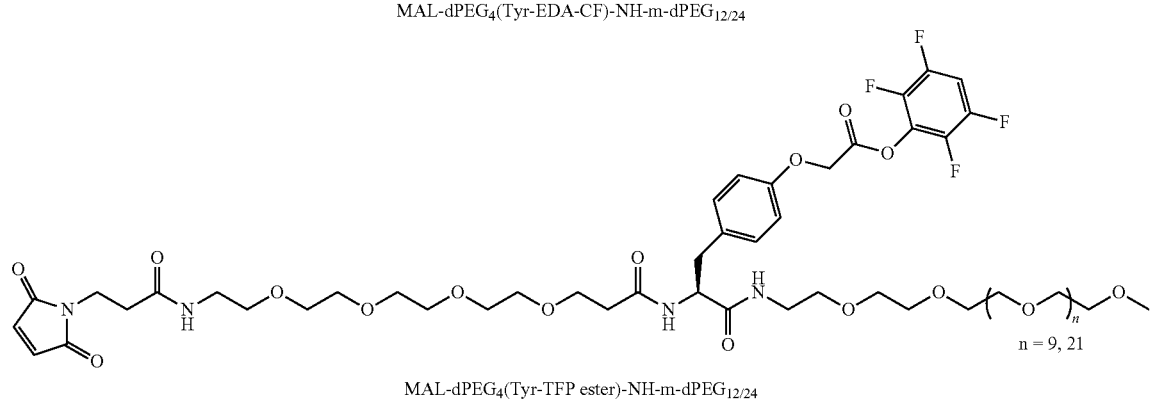
MAL-dPEG₄(Tyr-TFP ester)-NH-m-dPEG₁₂/₂₄
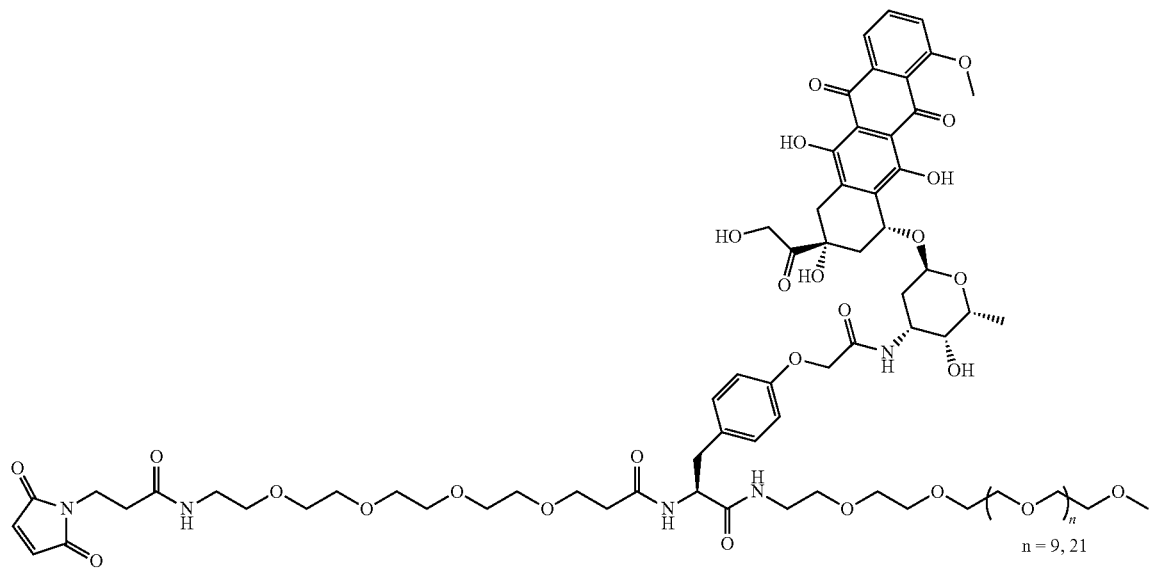
MAL-dPEG₄(Tyr-NH-Doxo)-NH-m-dPEG₁₂/₂₄

or for example where there are three AC's,
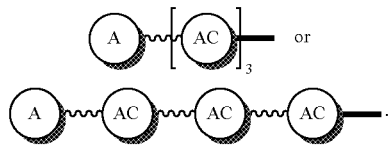

or

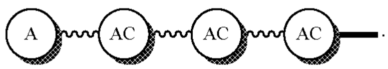

The AC's can be the same or different. In the case where the AC's are the same,
Having a construct such as this allows for the multiple attachment of a diagnostic or therapeutic agent and then to further attach the A to a biologic agent A.
can be made by at least two different routes. Shown below is an approach for putting on the solid line, —, in the final part of the method of preparation and the solid line can be optimized for a range of solid lines, —.

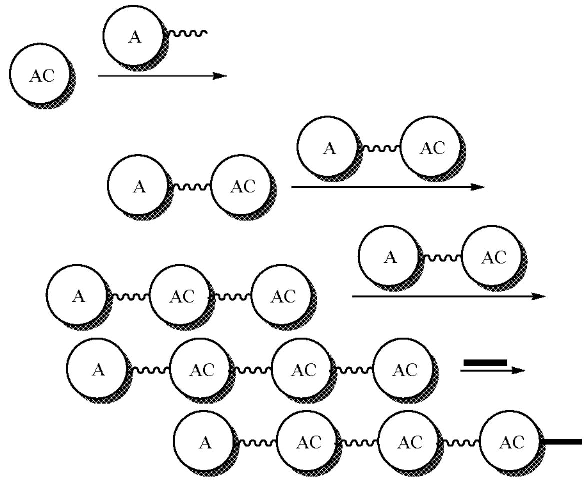

Shown below is a specific example of a method to make an example of this approach where each of the AC's are the same, and the final AC is converted to the active ester and the maleimide. In this case there is a critical common intermediate, 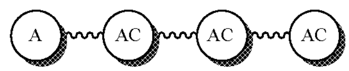 or from which a variety of other solid lines can be attached and the A converted to an optimal reactable A to be attached to the A used in a particular diagnostic or therapeutic application.

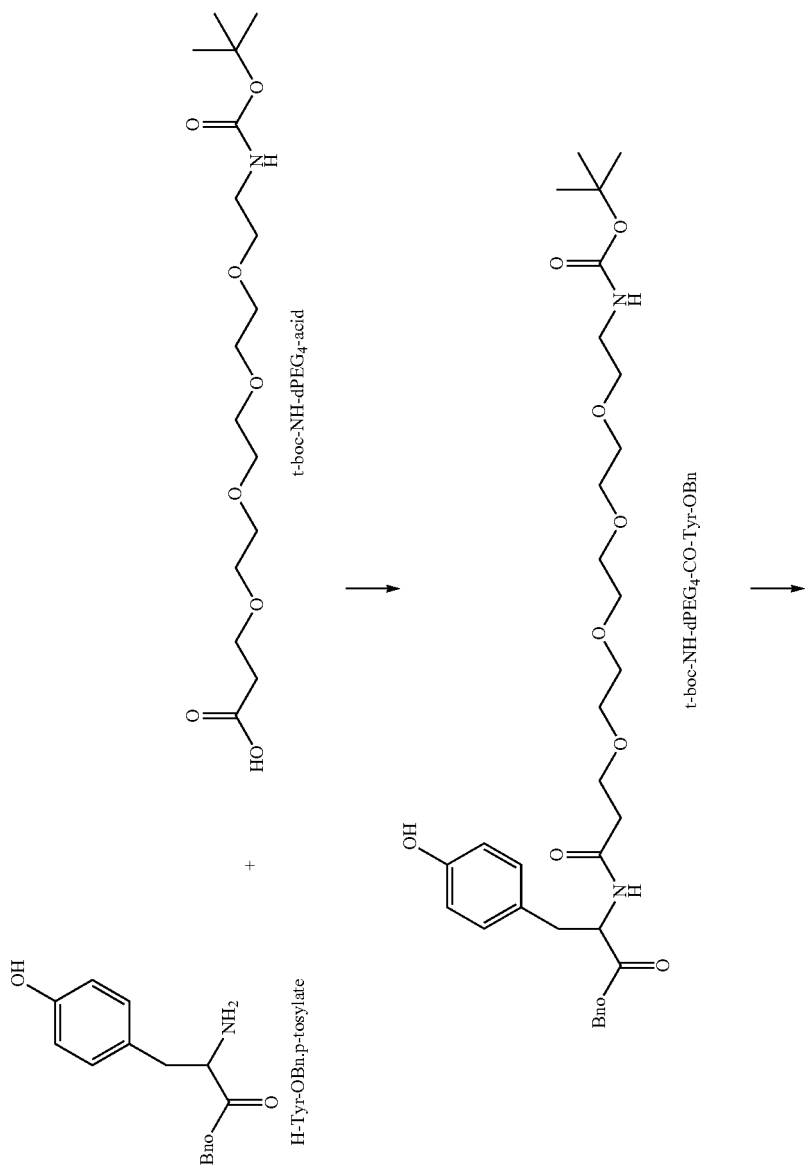

-continued
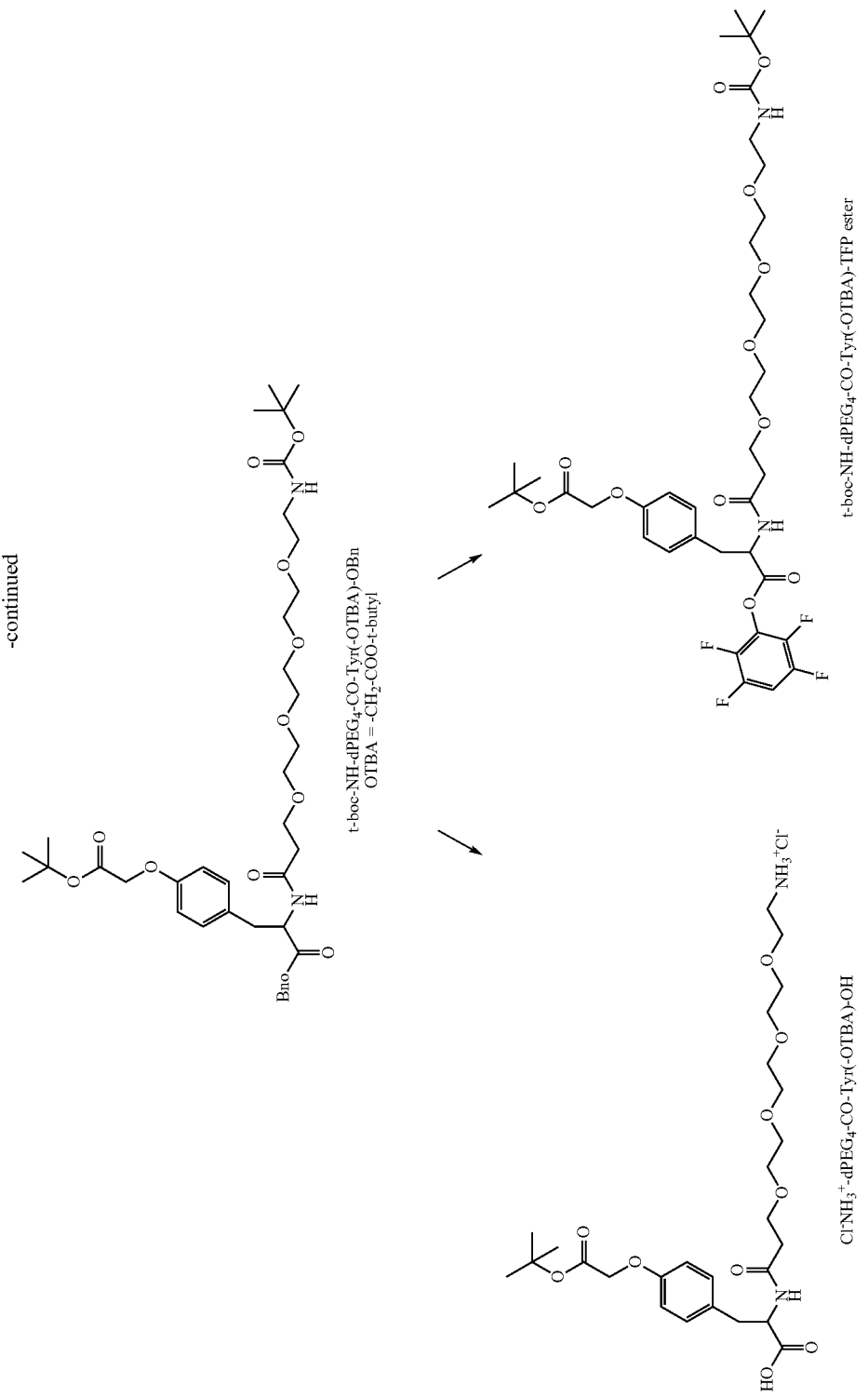

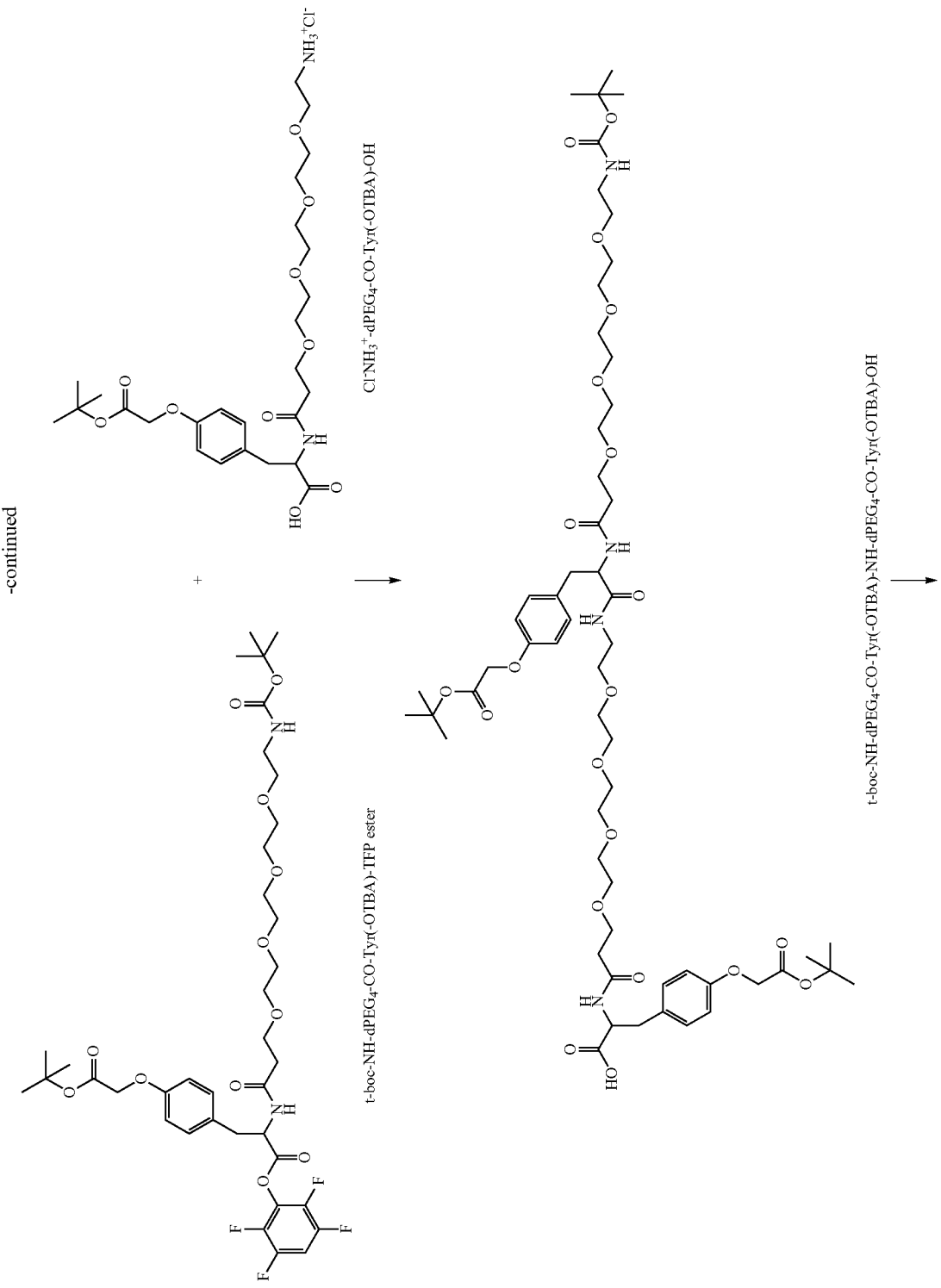

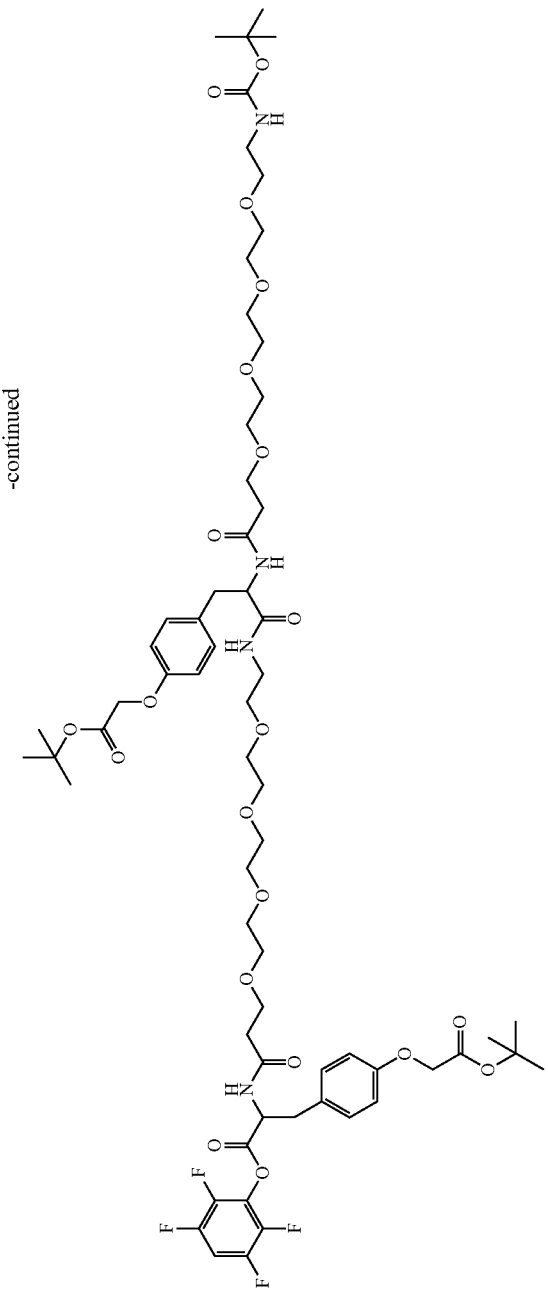

-continued
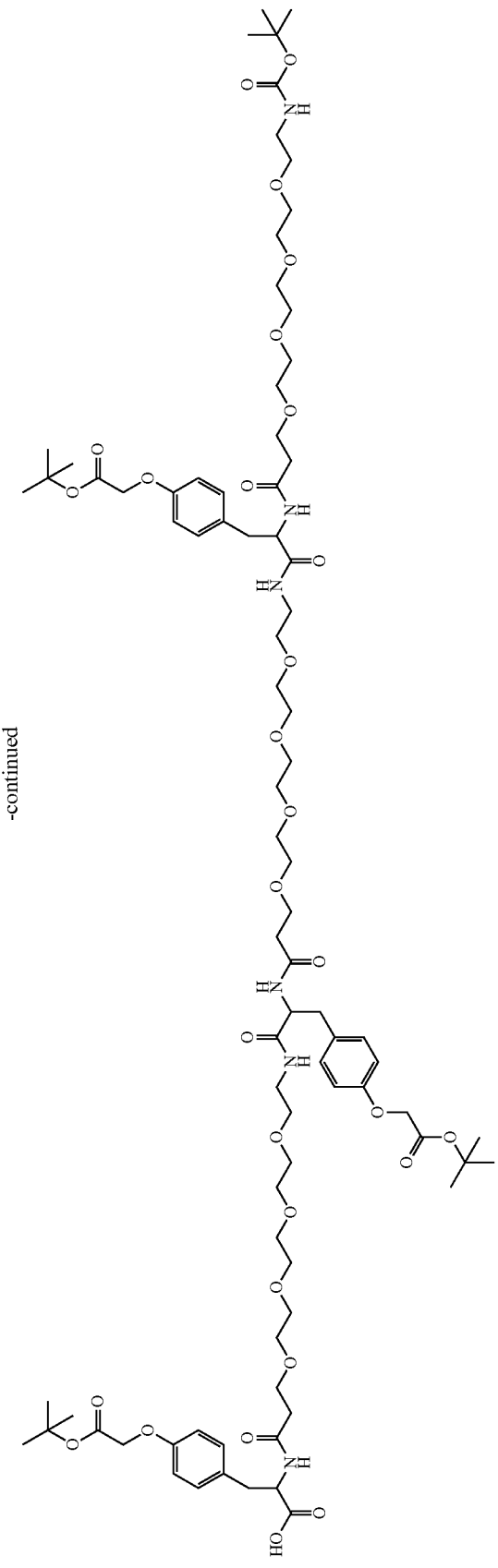
t-boc-NH-dPEG₄-CO-Tyr(-OTBA)-NH-dPEG₄-CO-Tyr(-OTBA)-NH-dPEG₄-CO-Tyr(-OTBA)-OH
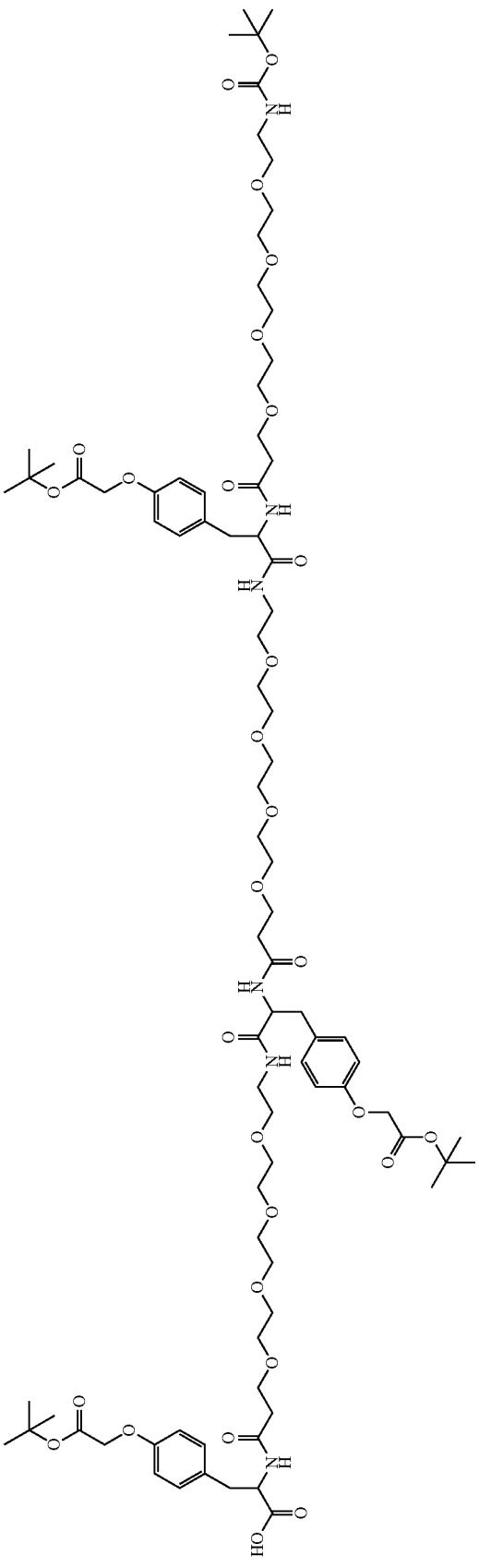
t-boc-NH-dPEG₄-CO-Tyr(-OTBA)-NH-dPEG₄-CO-Tyr(-OTBA)-NH-dPEG₄-CO-Tyr(-OTBA)-OH

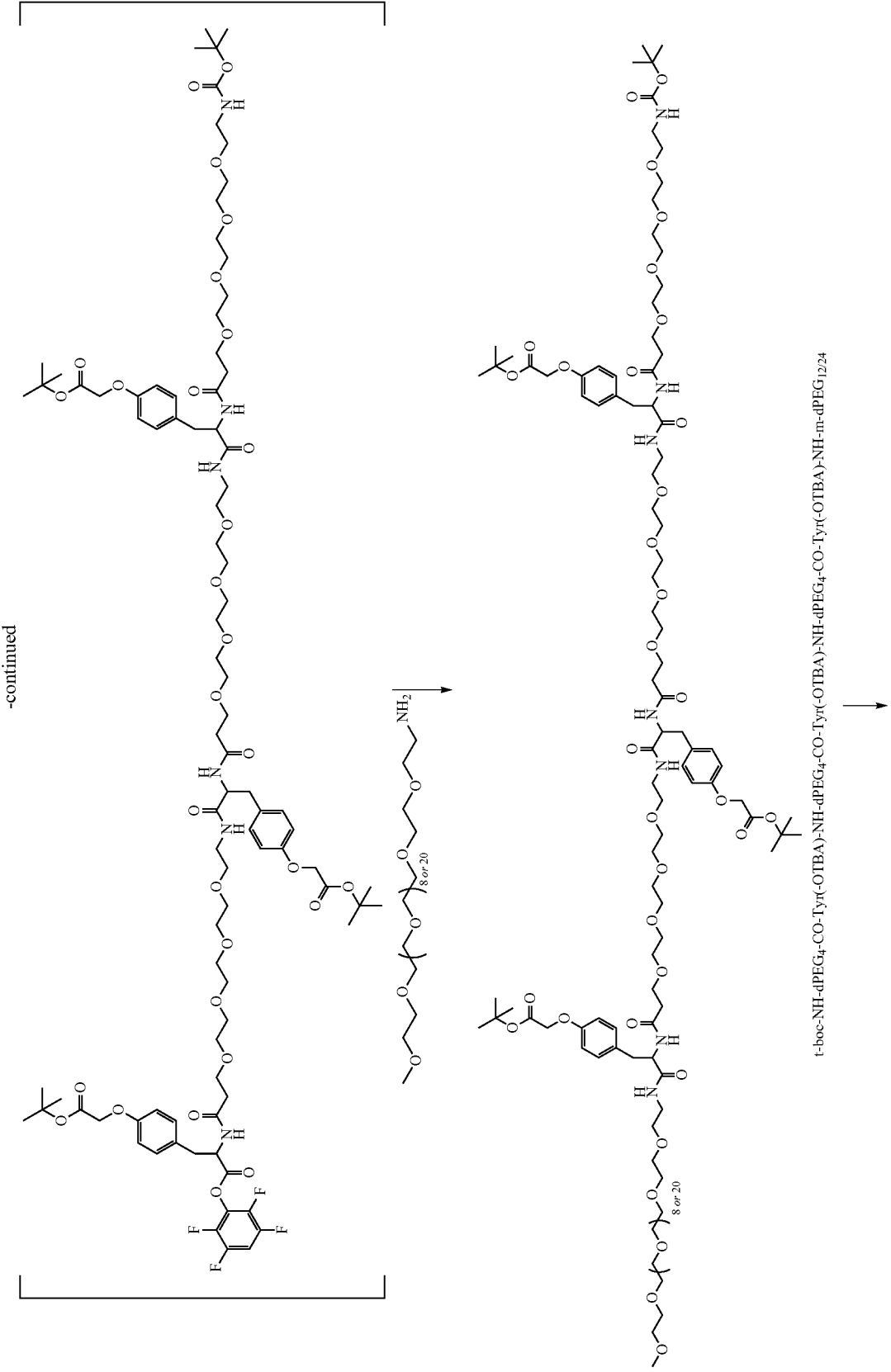

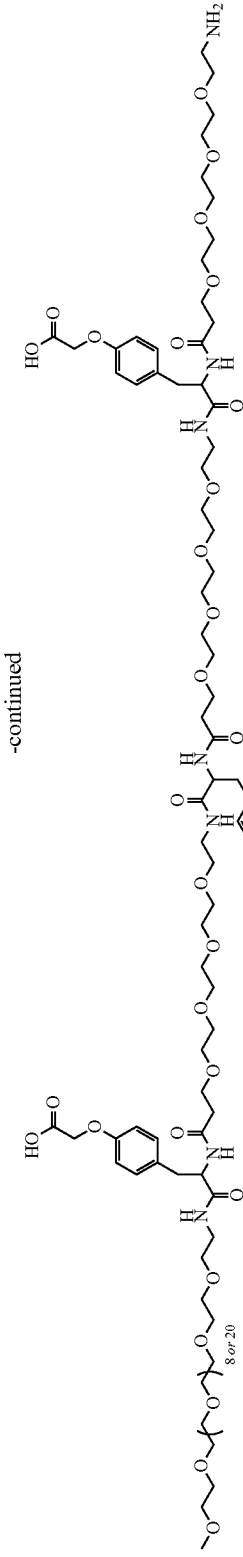

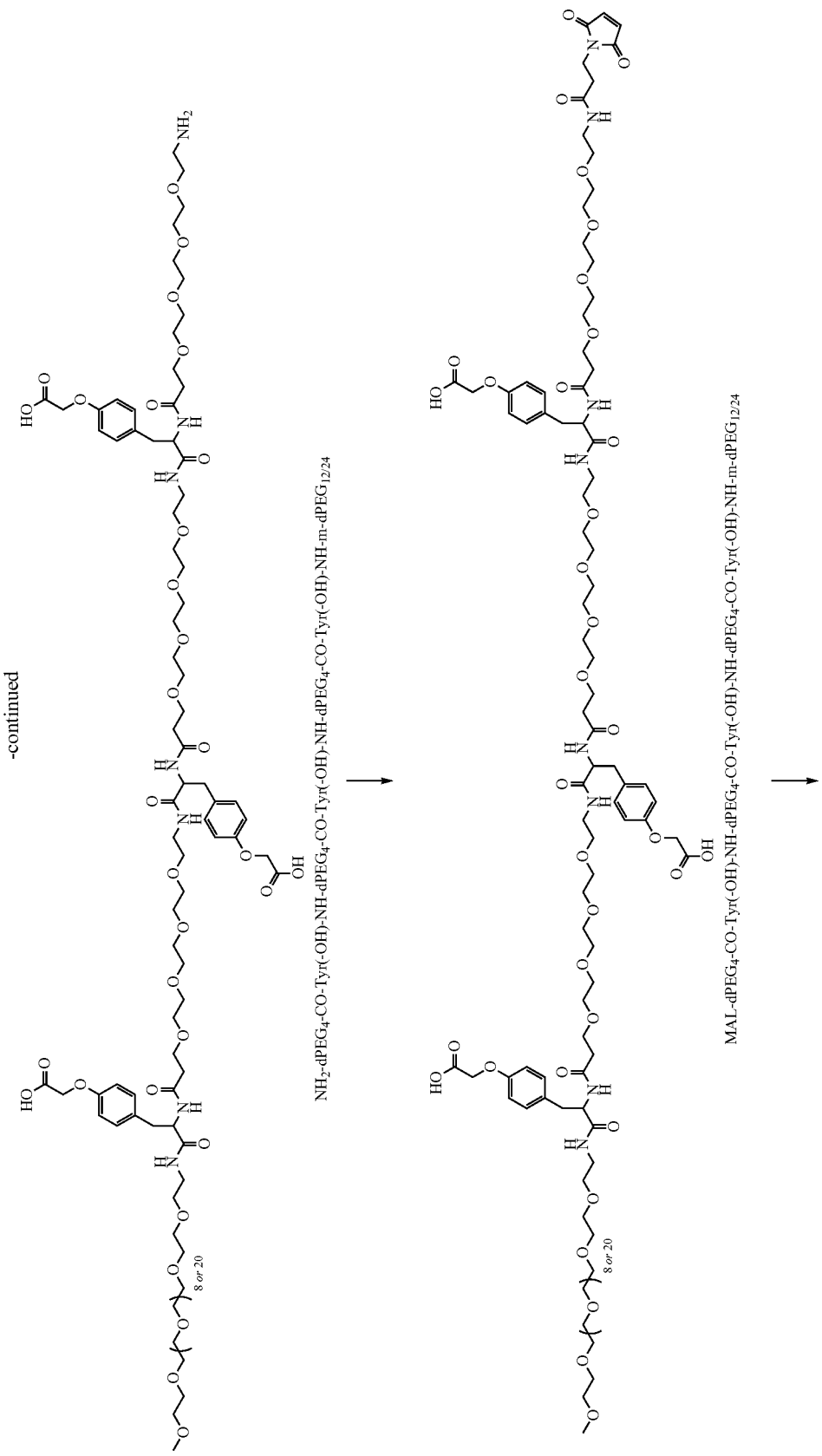

-continued
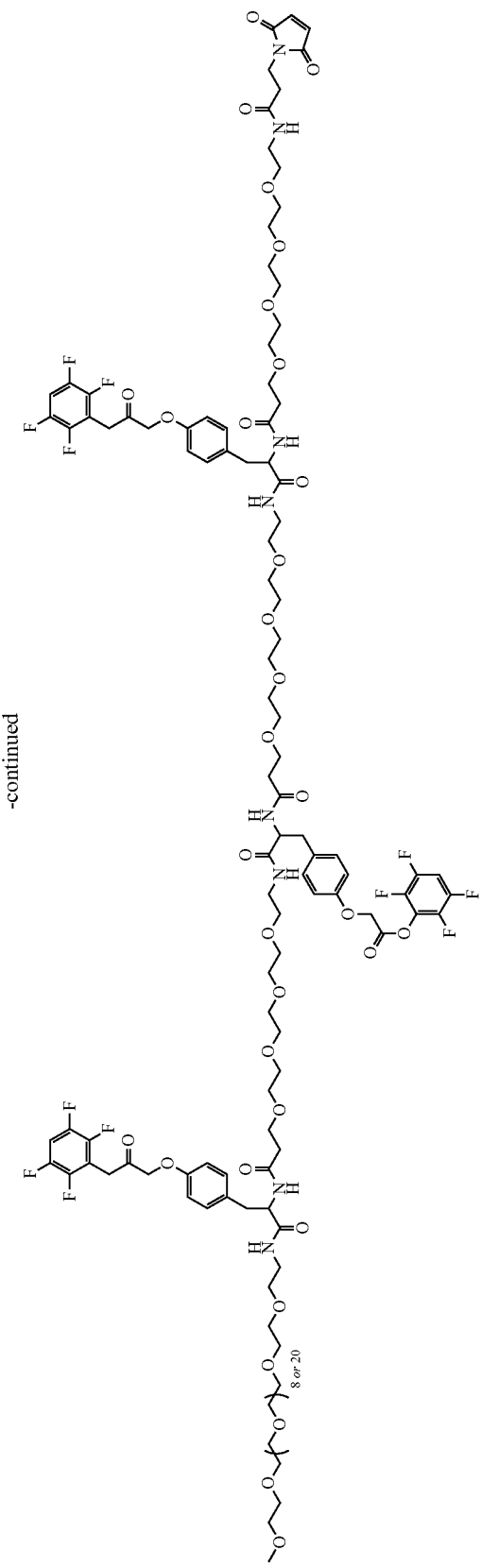
MAL-dPEG₄-CO-Tyr(-TFP ester)-NH-dPEG₄-CO-Tyr(-TFP ester)-NH-dPEG₄-CO-Tyr(-TFP ester)-NH-m-dPEG₁₂/₂₄

An alternative approach where the optimization could be in the AC or the wavy line, ——, or both, is to start with an optimal solid line and then add the appropriate and desired
The summary of this approach is shown presently.
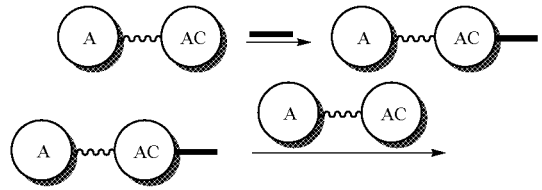
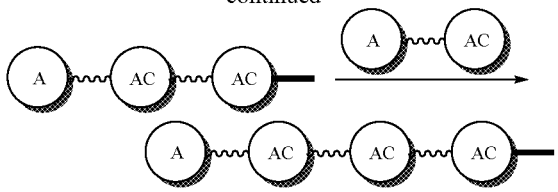
An example of a method using this approach, to make the same
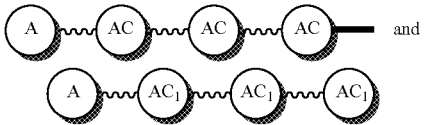 and
is shown below.

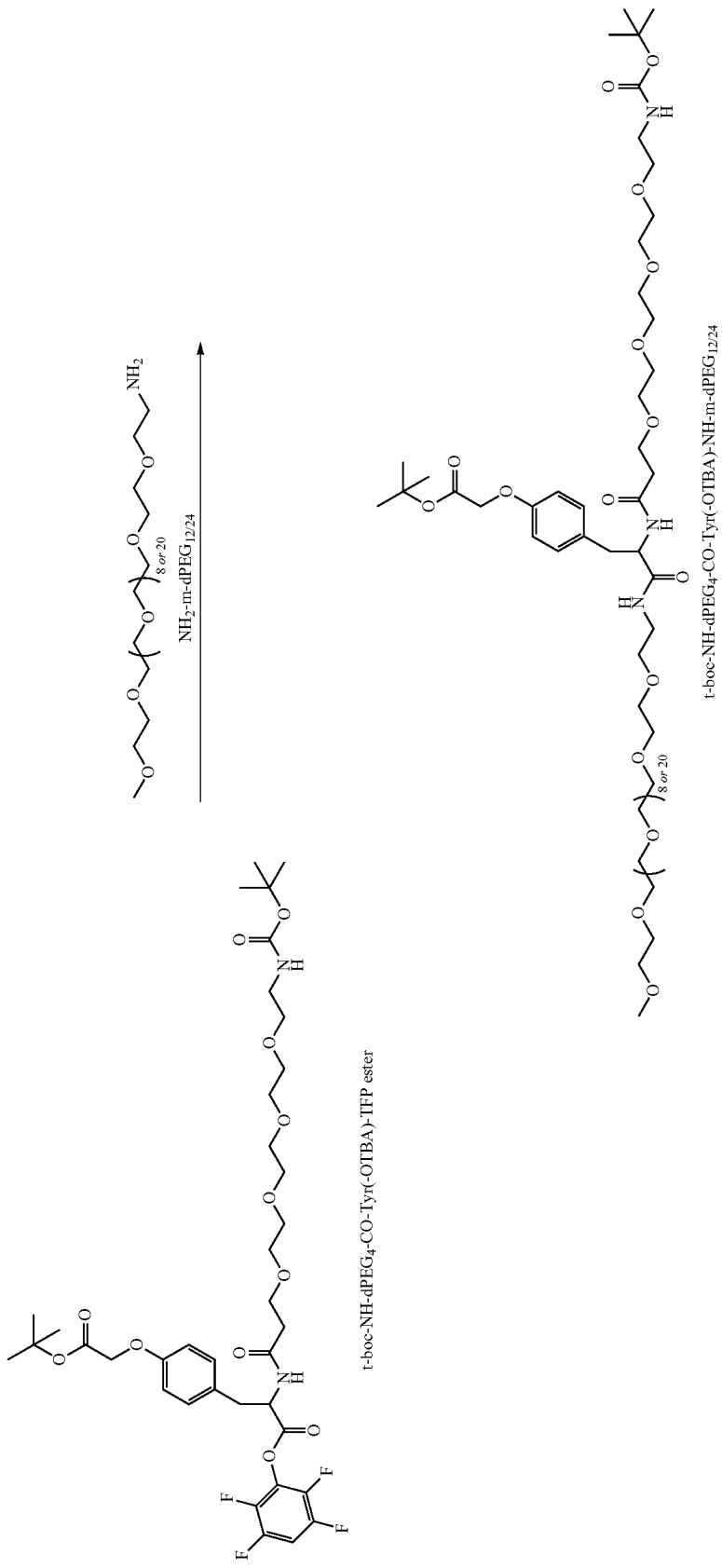

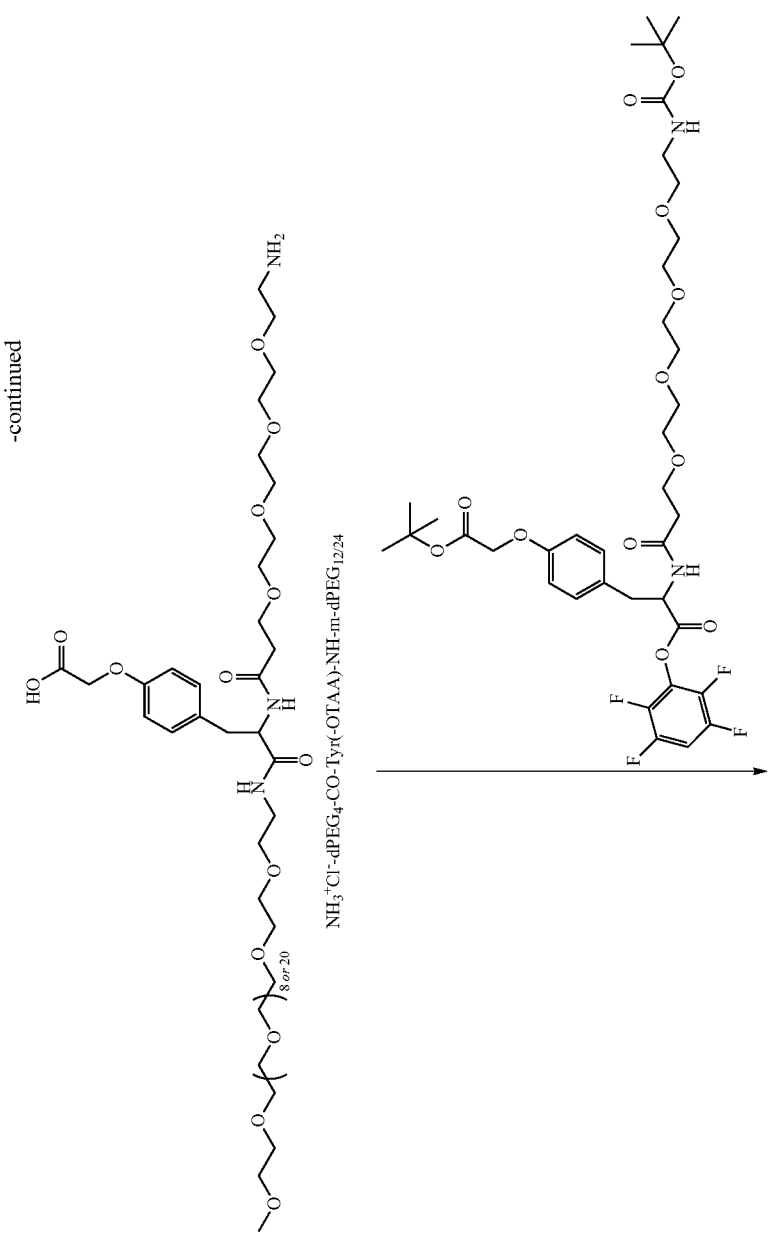

-continued
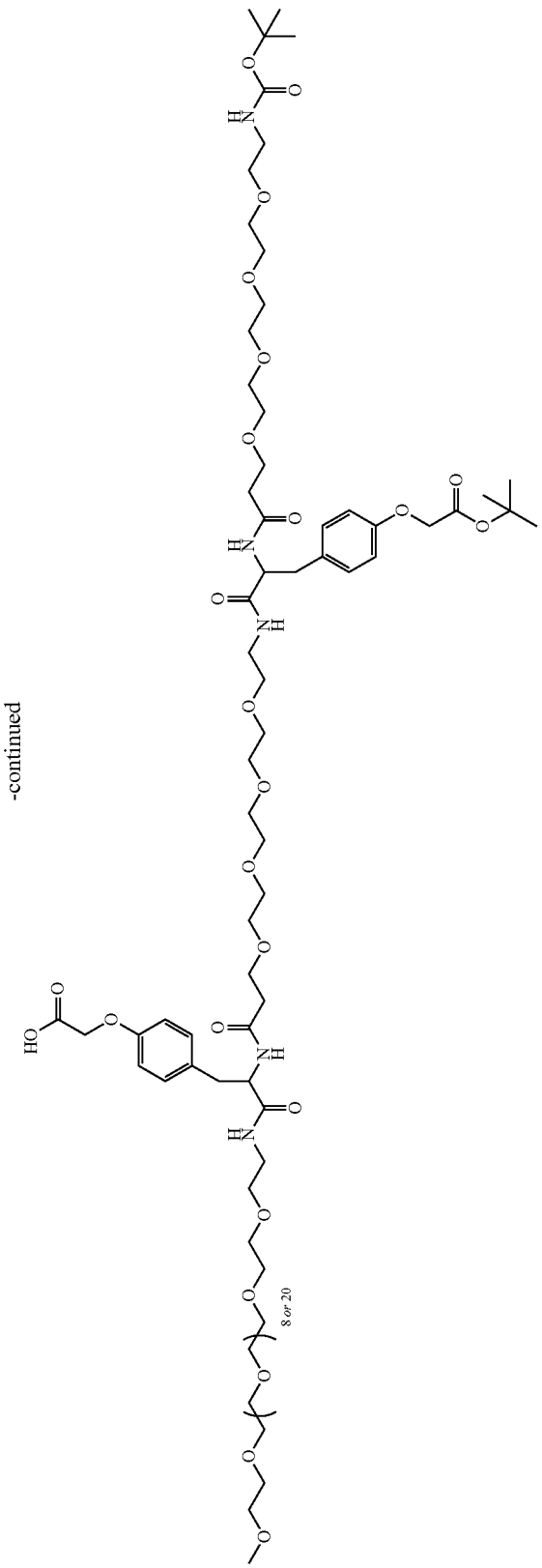

-continued
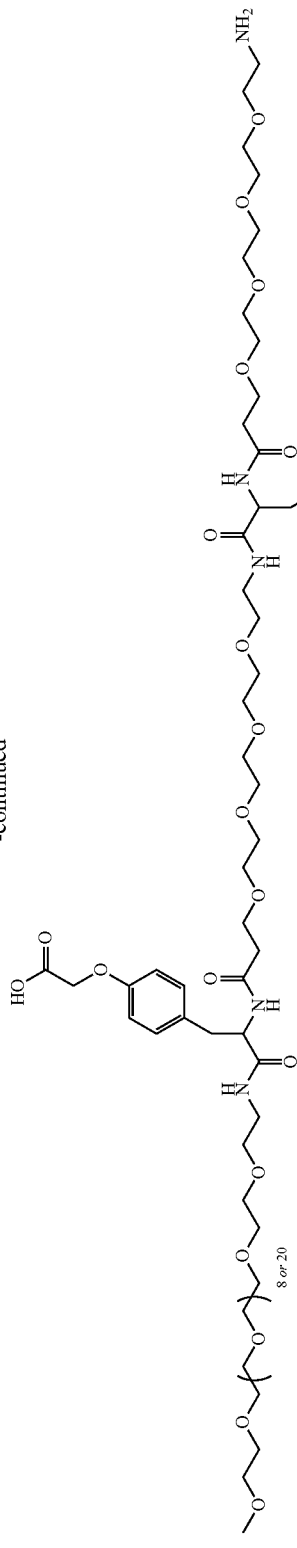
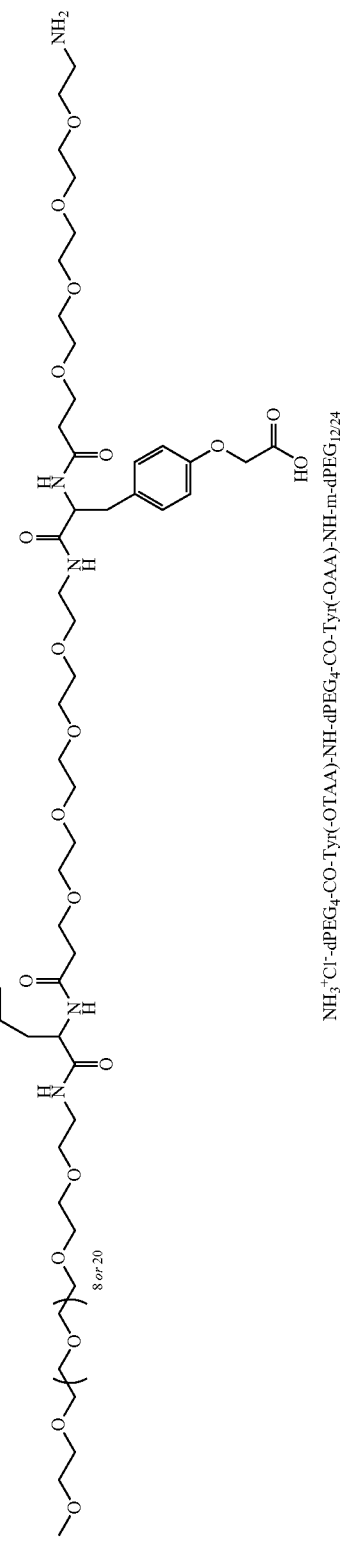

-continued
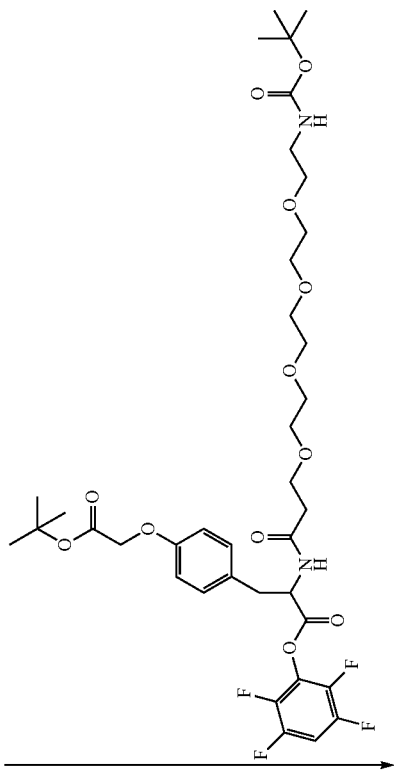
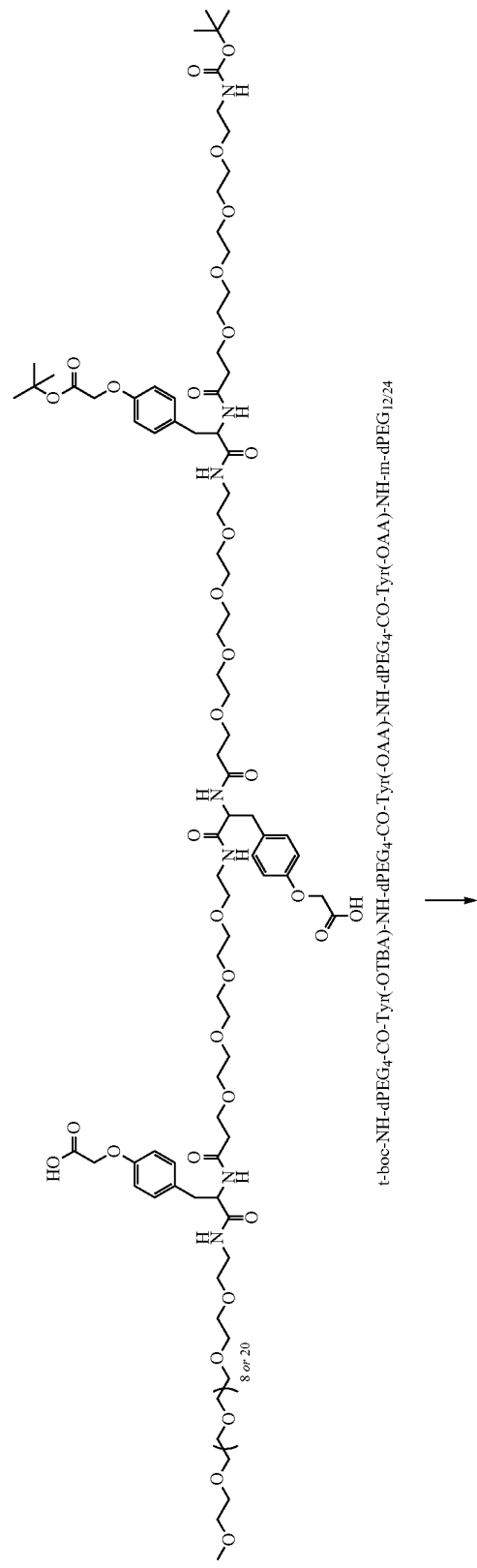

-continued
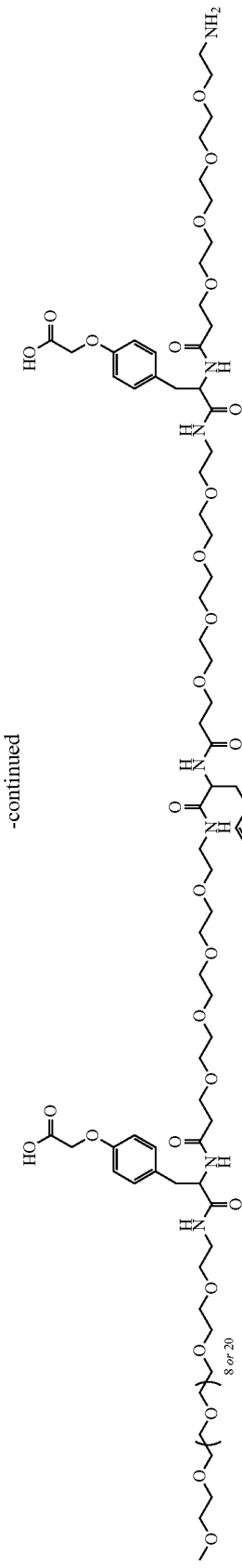
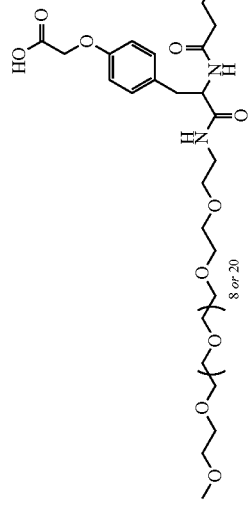
$NH_3^+Cl^-$-dPEG$_4$-CO-Tyr(-OAA)-NH-dPEG$_4$-CO-Tyr(-OAA)-NH-dPEG$_4$-CO-Tyr(-OAA)-NH-m-dPEG$_{12/24}$ And then from the same intermediate is converted to

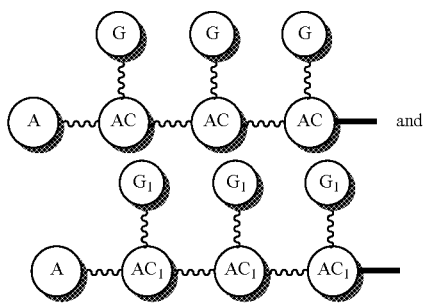
and as above.

Either of the above approaches can be used for making construct with greater than 3 AC's or

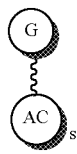

or to adjust the nature of the wavy line, but adding different lengths of dPEG or to incorporate a cleavable options as would be evident from the chemistry and constructs disclosed and including the conversion within the method to different final

in order to accommodate the optimal design for the desired diagnostic or therapeutic application.

The area of peptide synthesis is a very mature field and the options for having various combinations of AC for the potential incorporation of different final

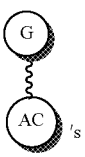

allows for a variety of methods drawn from the methods and constructs disclosed herein.

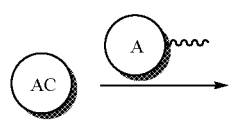

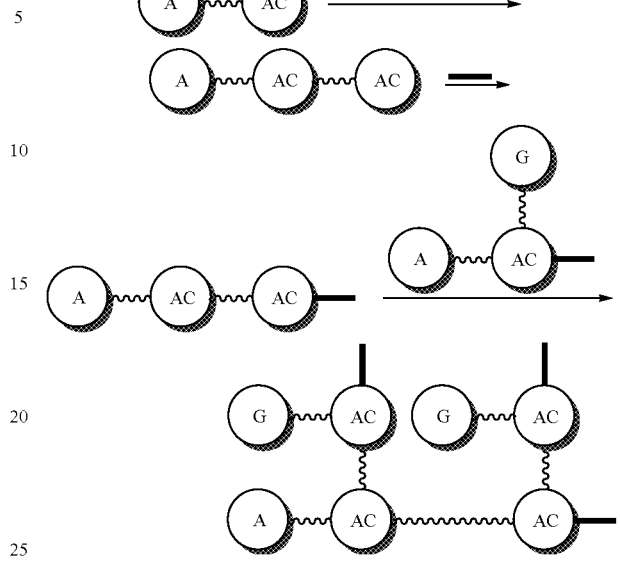

A preferred embodiment is for the random or site specific conjugation or labeling of a straight unmodified linear discrete PEG construct w/ and w/o terminal charge, wavy or solid line (for a diagnostic (in vitro)/imaging (in vivo) application on a non-engineered antibody fragment or engineered scaffold), $$\left[ \begin{array}{c} G \\ \text{\textasciitilde} \\ A \text{\textasciitilde} AC \end{array} \right]_n ,$$

where n=0. Optionally the random conjugation could be followed by a labeling and other conjugation procedure. On a whole antibody or an antibody fragment, like a diabody or a variety of Fab or Fab', this could lead to an enhancement of the BD and cell internalization properties verses the undPEGylated or randomly labeled or conjugated without the random unmodifiecd linear discrete PEG construct, with or without a terminal charge or as a wavy or solid line.

Another preferred embodiment is the random conjugation or labeling of each embodiment of the linear multifunctional dPEG constructs, e.g.,

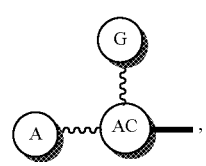

preferably, but not limited to an in vitro diagnostic onto an antibody or antibody fragment or on to an engineered protein scaffold to produce

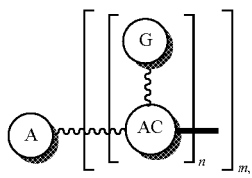

where m is going to be a distribution depending on the number of reactive moieties on the protein, and the normal variables of reactivity, stoichiometry, concentration, etc., of the reaction. This can be controlled precisely and optimally when the reaction is carried out in a microreactor.

Another preferred embodiment is a site specific attachment of a of reactable A of the various disclosed dPEG constructs with linear multifunctional discrete PEG construct, etc., either as one, or as multiples onto a the interchain disulfides of a whole antibody, Fab, Fab', or a protein with one or more engineered disulfides, ones engineered not to effect the specific binding efficacy of this type of preferential locator protein. Attached site specifically using one or more of the following: A is ETAC, as in US Publication No. 20130338231, a maleimide or vinylsulfone or derivatives, as in Godwin US Publication No. 20140081047, haloacetimdo, or maleimide derivatives disclosed in Jackson, U.S. Publication No. 20130224228 with and without terminal charge. The terminal charge can be positive or negative with the intent to control the kidney elimination or for cell surface control, to internalize or not to internalize the construct as desired in the application. Imaging application might utilize a surface binder, while a therapeutic could use either, depending on the mechanism of action. The site-specific attachment also can be into one or more disulfides that can commonly be introduced into engineered proteins as preferential locators, and engineered so as not to interfere with the binding or targeting action of the preferential locator, e.g., as disclosed in Hudson, U.S. Pub. No. 20120164068 and 20120171115 for an anti-TAG-72 diabody construct with two disulfides. Site-specific attachment is preferred where reactable A reacts selectively with preferential locator proteins that have non-natural amino acids engineered into them (Refs. Bioorthogonal Chemistry: Fishing for Selectivity in a Sea of Functionality, Ellen M. Sletten and Carolyn R. Bertozzi, Angew. Chem. Int. Ed., 2009, 48, 6974-6998; Nonnatural Amino Acids for Site-Specific Protein Conjugation, A. J. de Graaf, et al., Bioconjugate Chemistry, 2009, 20, 1281-1296. The resulting dPEG constructs will have the following general forms, where m will be controlled by the number of specific sites, and will optimally be an integral number.

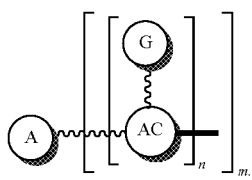

E.g., if the anti-TAG-72 diabodies are reduced and reactable A is a maleimide, m will be 4. If the reactable A is ETAC, then optimally m will be equal to 2.

A specific and preferred application of the disclosed constructs is in their application to drug conjugates with preferential locators. The dPEG constructs,

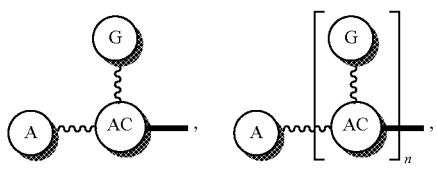

both resulting in conjugate stoichiometry determined by the chemistry positions for A as a reactable group to react, and the different variety of chemical reactivity on the preferential locator as the protein or peptide engineering options determine this, such that the resulting conjugates may have optimal biodistribution and stability, both chemically and immunologically, as well as enhancing the cell internalization properties due to the novel properties the linear solid line dPEG gives to the drug conjugate. In addition the typical problems of aggregation and solubility of these compounds made by traditional chemistries will be eliminated.

Another preferred embodiment is where "A" is a single peptide, e.g., somatistatin-14 or an octreotide variant, or other highly specific binding peptides (see references in definitions of A). In this case the peptide "A" can carry on of the disclosed dPEG constructs, but the peptide itself can be configured as A as disclosed in Davis, U.S. Pub. No. 20130052130 paragraphs (0209) to (0230), and such that the binding is optimized and novel design of the currently disclosed dPEG constructs can optimally carry the diagnostic or therapeutic or both agents to its target.

Another preferred embodiment for "A" as a preferential locator construct to be reacted with the currently disclosed dPEG constructs, is made up of putting together a series of at least two cyclic or peptide loops, ones that are mimics for the binding site of the antibody (CDR peptide mimetics) or an engineered scaffold or other preferential locator. Again being accomplish by an "A" construct from those disclosed in Davis, U.S. Pub. No. 20130052130 paragraphs (0209) to (0230), and using  to further control the utility of this discrete PEG based construct. A further novel option is to use these peptides with a dPEG , to be reacted with or

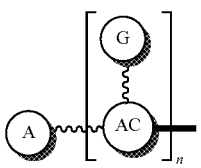

where n is 2 or more and the AC's can be the same or different depending on the design requirements of the preferential locator. This can then be reacted with a

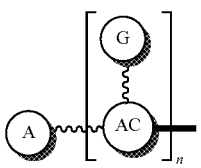

or where G is the diagnostic or therapeutic agent or both.

Optionally, rather than looping the cyclic peptides with the disulfide and then build the discrete PEG based construct from each cysteine in the looped or cyclic peptides, a preferred embodiment is to use a bisMAL, ETAC or other bisthiol reactive AC/A to bridge the disulfide and then build the desired discrete PEG construct this way, with various and optimal options of the linear discrete PEG construct options disclosed herein. "A" configurations as disclosed in Davis, U.S. Pub. No. 20130052130 paragraphs [0209] to [0230] can also be used in a like method.

Another preferred embodiment is the specific case for using the full complement of chelators for the corresponding radionuclide(s) that can specifically and site-specifically labeled rather than done so randomly like is typical for the iodine radioisotopes, an exception would be iodine isotopes on boron cages. Preferred embodiments are for the use of multiple chelators that are the same, or optionally using different chelators specific for different radionuclides, with various configurations of reactable AC in the dPEG constructs disclosed herein.

Another particularly preferred useful embodiment is for G in the various disclosed dPEG constructs to be a drug or prodrug, i.e., releasability is built into the wavy line, ~~~~, where the drug is one or more from the cytotoxins, including common ones like doxorubicin, or more recently approved cytotoxins as part of an ADC, like the auristatins or maytansinoids, or others that have been known to be very potent, like the PBD's, pyrrolebenzodiazepines.

Another preferred embodiment is a method to make theranostic with the novel properties of the disclosed dPEG constructs, where at least 2 differently reactable AC's are incorporated and then separately reacted to ~~~~ G, where, e.g., G is an imaging agent like a radionuclide or optical agent and the other ~~~~ where G is a cytotoxic agent. Preferably, the AC is a tyrosine or tyrosine derivative, which are bi or triorthogonal in their chemistry selectivity at the phenolic position. Other reactable multifunctional amino acids are preferred in many cases, including lysine, aspartic and glutaric acids. In addition there are a range of non-natural amino acids, many of which are used to incorporate biorthogonal functionality to a peptide or protein, but could be applied in the methods disclosed herein for making novel linear dPEG constructs. (Ref.: (a) Liu and Schultz, Annual Rev. Biochem., 79 (2010) 413-444; and (b) A. J. de Graaf, et al., Bioconjugate Chem., 20 (2009) 1281-1295.

Another useful embodiment for a ~~~~ G can be constructed where G is a cyclic peptide, looped as a disulfide where the original reactable AC is a bisMAL or ETAC or other disulfide bridging chemistry, e.g., Jackson, U.S. Pub. No. 20130224228. This bridging disulfide chemistry is a preferred option for reactable A to another preferential locator in or Another preferred embodiment for A (or AC) is to use the standard copper catalyzed Click chemistry, preferred for peptides or small protein or aptamers, additionally using the copper free click chemistry like the BCN/azide (Ref. DOI: 10.1002/cbic.201100206 in *Chem Bio Chem*), DBCO, tetrazine and others currently in the art, but give novel constructs when combined with the linear and related dPEG constructs disclosed herein.

Another preferred embodiment is the series of discrete PEG constructs with the disclosed terminal solid line, ——, that is optimized in their length, with a dPEGn, where n=8-36 units, or n=8-72 units where there are amide spacers in the solid line, as well as the terminal charge in order for the construct to facilitate or to prevent the cell internalization of the diagnostic or therapeutic construct and non-penetration of the BBB (Ref. Bulaj, et al., Molecular Pharmaceutics, 10 (2013) 574-585).

Another useful embodiment is the multifunctional construct of PhthN-dPEGx-Tyr(FG)-dPEGy-FG', where x is 2-24 and y is 4 to 48. More generally the PhthN can be made compatible with the FG and FG', or reactable in a sequence to make this an efficient core construct for the linear discrete PEG constructs disclose herein. Optionally the tyrosine can be replaced with another amino acid, but the tyrosine is preferred since the phenol can be converted easily to all other useful biorthogonal functional groups and optionally to have a discrete $PEG_z$, spacer/linker as part of a ~~~~.

The following examples demonstrate how the disclosure may be practiced, but they should not be construed as limiting. All references herein are incorporated herein by reference.

EXAMPLES

Data comparing the delivery efficiency of a targeting peptide, a 13mer, with a fluorescein fluorophore attached to the N-terminus, with no spacer (FITC) or no dPEG® and with a dPEG®$_{12}$ spacer (5(6)-carboxyfluorescein-dPEG$_{12}$) between the dye and the peptide. And the data shows that the nature of the linear discrete PEG linker and length of the spacer shows that this variable has great potential to control the transport of the preferential locator into a specific cell, but increasing the internalization over 30 minutes by a factor of 10. It is already well known that the discrete PEG construct cause the constructs to be soluble in water.

Experimental

1. PhthN-dPEG$_4$-Tyr-OBn ester (PhthN-dPEG$_4$(Tyr-OH)-OBn)

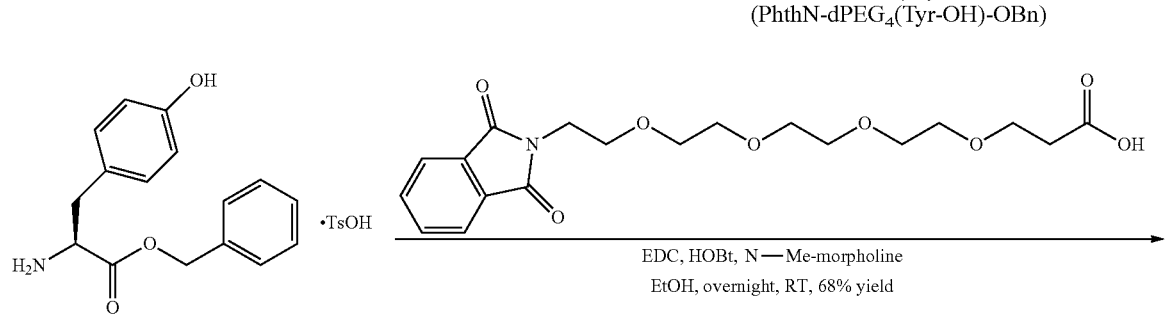

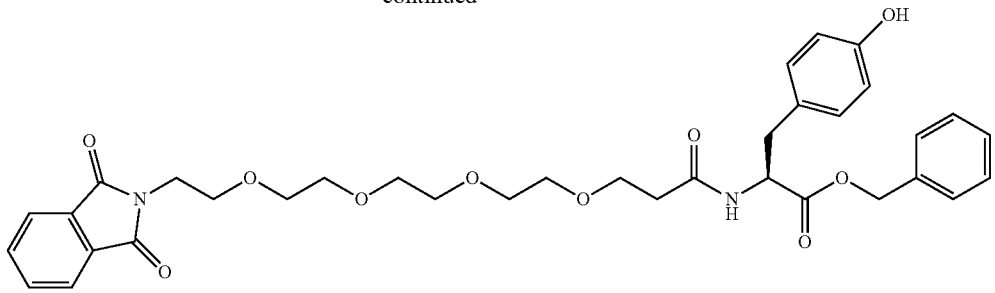

A total of 100 g (253 mmol) of PhthN-dPEG4-CO2H was charged in a 2 L 3-neck round bottom flask equipped with a thermocouple, N2 bleed, O/H stirrer and cooling ice bath. Ethanol (1.5 L, 200 proof) was added following by addition of N-methyl morpholine (82 mL, 809 mmol), tyrosine benzyl ester tosylate (123 g, 278 mmol) and HOBt (6.41 g, 37.9 mmol). The mixture stirred for 10 min, and then cooled in an ice bath. The coupling reagent EDC hydrochloride (72.7 g, 379 mmol) was added in a single and the reaction was slowly allowed to warp to room temperature overnight. After completion of the reaction, the solvent was removed under reduced pressure, the residue was taken in 1 L of water and extracted with ethyl acetate (3×100 mL). The extract was washed with 10% HCl (200 mL), saturated sodium bicarbonate 9200 mL), brine (200 mL) and dried over anhydrous sodium sulfate. Drying reagent was filtered off, and clear filtrated was concentrated under reduced pressure to give 142.5 g of yellow viscous oil. The obtained crude was purified on silicagel plug (850 g of silica) using dichloromethane-ethanol as eluent with gradient from 0% to 8% ethanol to give 111.6 g (68% yield) of the product as clear viscous oil.

$^1$HNMR (400 MHz, CDCl$_3$, δ): 9.21 (s, 1H, OH), 8.28 (d, 1H, NH), 7.88 and 7.80 (m, 4H, phthalimido), 7.37-7.22 (m, 5H, phenyl), 6.97 and 6.65 (two d, CH, tyrosine), 5.06 (s, 2H, benzyl), 4.45 (m, 1H, N—CH—CO), 3.74 (t, 2H, CH2-N-phtalimido), 3.62 (t, 2H, CH2O), 3.55-3.33 (m, 14H, CH2O), 2.86 (dddd, 2H, CH2-C6H4-O), 2.33 (t, 2H, CH2CO).

2. PhthN-dPEG$_4$-Tyr(O-propargyl)OBn ester (Phth N-dPEG$_4$-Tyr(O-propargyl)OBn)

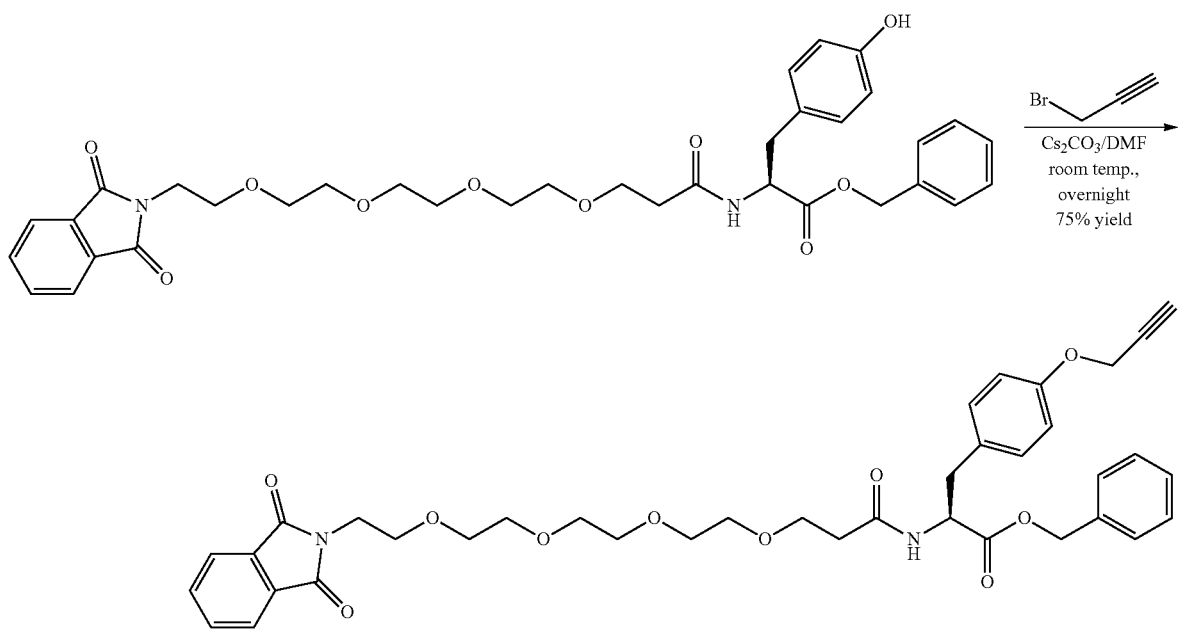

A total of 40.9 g (63 mmol) of Phth-dPEG4-Tyr-Bn ester was charged in a 0.5 L 4-neck round bottom flask equipped with a thermocouple, N2 filled balloon, magnetic stirrer and cooling ice-MeOH bath. Anhydrous DMF (dried over 4A molecular sieves) was added and the mixture stirred until clear yellow solution was obtained. The solution was cooled to −6° C., and 37.85 g (116 mmol) of cesium carbonate was added portion-wise resulting in formation of yellow cloudy mixture. The obtained mixture stirred at −8° C. for 10 min, and propargyl bromide (11.88 g of 80% solution in toluene, 80 mmol) was added drop wise via syringe with the rate to maintain temperature around 0° C. Cooling bath was removed and reaction was allowed to warm to room temperature and stirred overnight until all Phth-4-tyr-OBn was consumed by TLC and HPLC. The reaction mixture was diluted with 200 mL of dichloromethane, and resulting suspension was filtered over celite in order to remove an excess of cesium carbonate. The clear yellow filtrate was concentrated under reduced pressure at 35° C. in order to remove DMF. Obtained viscous yellow oil was diluted with dichloromethane (250 mL) and consequently washed with water (3×200 mL) and brine (1×200 mL). The organic bottom phase was separated, dried over anhydrous sodium sulfate for 1 hr under stirring and concentrated under reduced pressure to give 46 g of crude material as viscous yellow oil. This crude was purified on a silica gel plug (597 g of silica). Sample was loaded as a solution in 70 mL of dichloromethane, and eluted with $CH_2Cl_2$/EtOAc=1:1. Pure fractions were collected and concentrated on rotavap to give 32.3 g (75% yield) of viscous oil ($R_f$=0.18 in $CH_2Cl_2$-EtOAc=1:1).

$^1$HNMR (400 MHz, $CDCl_3$, δ): 7.75 and 7.62 (2m, 4H, phthalimido), 7.29-7.20 (m, 5H, phenyl), 6.88 and 6.73 (two d, CH, tyrosine), 6.78 (d, 1H, NH), 5.05 (q, 2H, benzyl), 4.80 (q, 1H, N—CH—CO), 4.56 (d, 2H, O—CH2-acetylene), 3.81 (t, 2H, CH2-N-phtalimido), 3.67-3.42 (m, 16H, CH2O), 2.98 (m, 2H, CH2-C6H4-O), 2.47 (t, 1H, acetylene), 2.40 (m, 2H, CH2CO).

3. PhthN-dPEG$_4$-Tyr(O-methylene-triazole-coumarin)OBn ester (PhthN-dPEG$_4$-(Tyr-OCH$_2$-triazole-7-hydroxycoumarin)-OBn)

A total of 0.731 g (1.064 mmol) of Phth-dPEG4-Tyr(O-propargyl)OBn ester and 0.223 g (1.098 mmol) of 3-azido-7-hydroxycoumarine were charged in a 50 mL one-neck RBF equipped with a magnetic stirrer, thermocouple and N2-filled balloon. Ethanol (15 mL, ultra-pure, 200 proof) was added via syringe and resulting mixture stirred in dark for ~10 min resulting in formation of cloudy brown solution. Water (5 mL, HPLC grade) was added drop-wise via syringe at 15° C. resulting in formation of clear "tea" colored solution. Solid sodium ascorbate (55 mg, 0.278 mmol) was added to the reaction following by addition of solid CuSO4.5H2O (24 mg, 0.096 mmol). The obtained mixture stirred at ambient temperature overnight in dark (flask was covered with foil for protection from light). The reaction mixture (yellow liquid phase and dark heavy bottom oil) was concentrated under reduced pressure, and obtained residue was dissolved in 100 mL of dichloromethane. This solution was washed with water (1×30 mL) and brine 10 mL). Bottom layer was separated, dried over anhydrous sodium sulfate and concentrated under reduced pressure to give 1.2 g of brown oil. Crude material was purified by column chromatography using dichloromethane-methanol as eluent with gradient from 100% to 85% dichloromethane. Collected fractions were concentrated and dried on high vacuum pump to give 0.823 g (87% yield) of product as clear glassy material.

$^1$HNMR (400 MHz, $CDCl_3$, δ): 8.55 (s, 1H, H—C4 in coumarin), 8.38 (s, 1H, triazole) 7.73 and 7.60 (2m, 4H, phthalimido), 7.41 and 7.05 (2d, 2H, coumarin ring), 7.30-7.20 (m, 5H, phenyl), 6.92 and 6.78 (2d, CH, tyrosine), 6.77-6.75 (s, 1H, HC8 in coumarin), 6.74 (m, 1H, NH), 5.12-5.011 (m, 4H, benzyl, O—CH2-triazole), 4.82 (m, 1H, N—CH—CO), 3.79 (t, 2H, CH2-N-phtalimido), 3.67-3.44 (m, 17H, CH2O, and OH), 2.98 (dddd, 2H, CH2-C6H4-O), 2.46-2.40 (m, 2H, CH2CO).

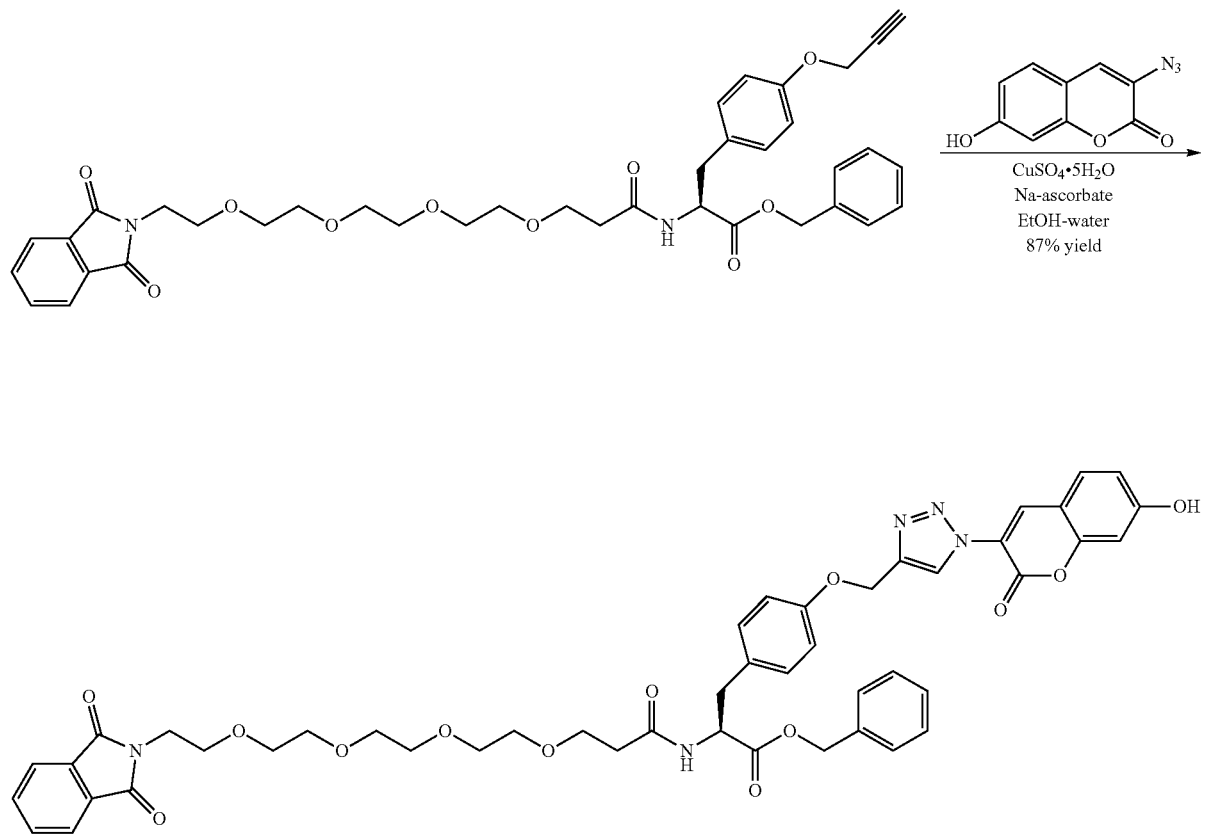

4. PhthN-dPEG₄-Tyr(O-methylene-triazole-ethane-amidoyl-BOC)OBn ester (PhthN-dPEG₄-(Tyr-OCH₂-triazole-CH₂CH₂NH-t-boc)-OBn)

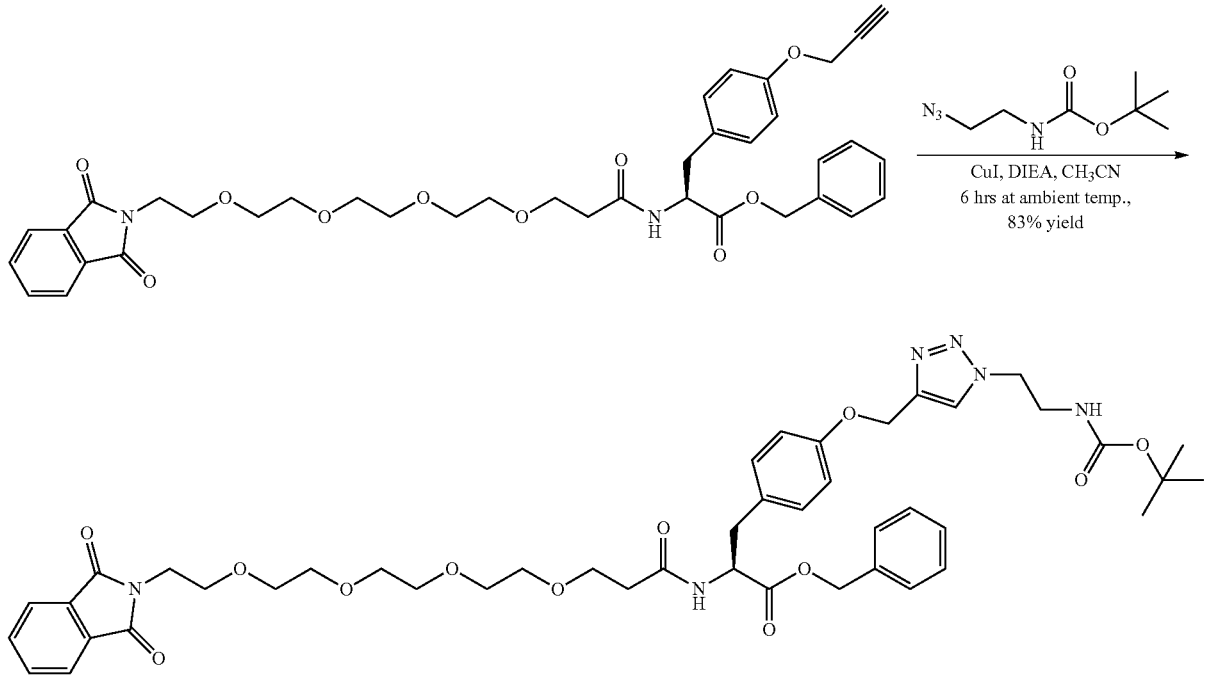 [SMILES: C#CCOc1ccc(C[C@H](NC(=O)CCOCCOCCOCCOCCN2C(=O)c3ccccc3C2=O)C(=O)OCc2ccccc2)cc1 ; CC(C)(C)OC(=O)NCCN=[N+]=[N-] ; CC(C)(C)OC(=O)NCCn1cc(COc2ccc(C[C@H](NC(=O)CCOCCOCCOCCOCCN3C(=O)c4ccccc4C3=O)C(=O)OCc3ccccc3)cc2)nn1]

A solution of 12.21 g (17.78 mmol) of Phth-dPEG4-Tyr (O-propargyl)OBn ester in 100 mL of anhydrous acetonitrile and 4.31 g (33.3 mmol) of diisopropylethyl amine were charged in a 4-neck 200 mL round bottom flask equipped with a thermocouple, balloon filled with nitrogen, and cooling ice-MeOH bath. The mixture was cooled to 12° C., and CuI (3.53 g, 18.54 mmol) was added in one portion resulting in formation of thick greenish-yellow suspension. A solution of 3.65 g (19.60 mmol) of N—BOC-ethyl amine in 15 mL of acetonitrile was added dropwise to the reaction at 0° C. with the rate to maintain the temperature around 0-5° C. After completion of the addition, the mixture stirred for 5 min, cooling bath was removed and the reaction stirred at ambient temperature for an additional 3 hrs. Solvent was removed under reduced pressure at ambient temperature. Obtained viscous oil was dissolved in 120 mL of dichloromethane, and consequently washed with water (100 mL), 1:1 diluted sodium bicarbonate solution (80 mL) and diluted ammonia (2×100 mL, NH₄OH:H₂O=3/7). The organic phase was separated from the top blue aqueous layer, washed with water (2×80 mL), brine (50 mL) and dried over anhydrous sodium sulfate. Drying agent was removed by filtration over celite, and colorless filtrate was concentrated on rotavap to give 1.5 g of clear viscous oil. This crude was purified by chromatography on silica gel using dichloromethane/methanol as eluent with gradient from 0% to 10% methanol. Pure fractions were collected and concentrated under reduced pressure to give 14.53 g (94% yield) of product as clear colorless glassy material.

¹HNMR (400 MHz, CDCl₃, δ): 7.56 (s, 1H, triazole) 7.75 and 7.62 (2m, 4H, phthalimido), 7.31-7.19 (m, 5H, phenyl), 6.88 and 6.75 (2d, CH, tyrosine), 6.78 (m, 1H, NH), 5.12-5.011 (m, 4H, benzyl, O—CH2-triazole), 4.95 (m, 1H, NH), 4.79 (dd, 1H, N—CH—CO), 4.41 (t, 2H, CH2-triazole), 3.79 (t, 2H CH2), 3.64 (t, 2H, N-phtalimido), 3.61-3.41 (m, 16H, CH2O), 2.96 (dddd, 2H, CH2-C6H4-O), 2.39 (t, 2H, CH2CO), 1.35 (s. 9H, t-Bu).

5. PhthN-dPEG4-Tyr(O-methylene-triazole-ethane-amidoyl-BOC) (Phth N-dPEG₄-(Tyr-OCH₂-triazole-CH₂CH₂—NH-t-boc)-OH)

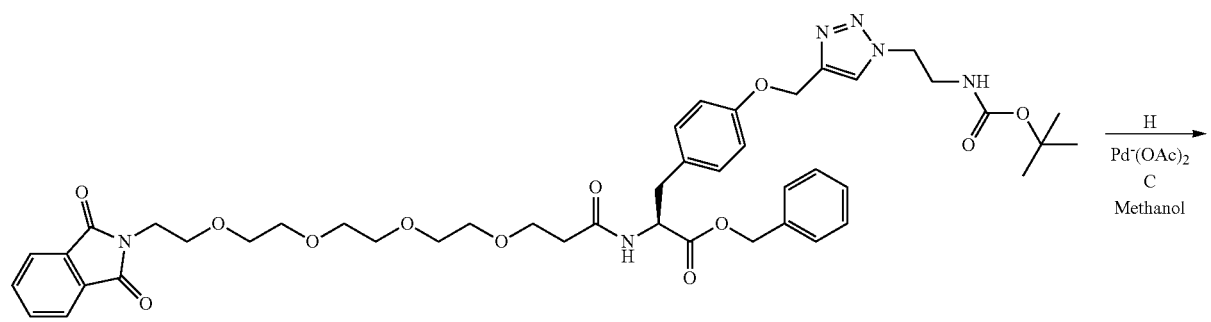

-continued

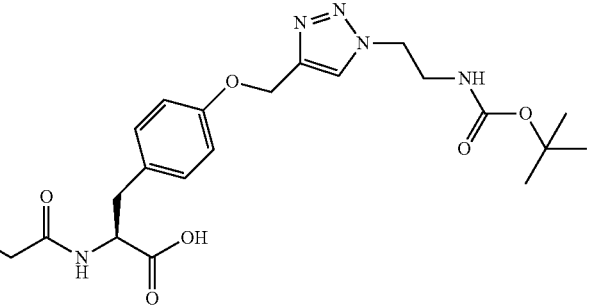
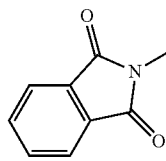

A solution of 3.03 g (3.47 mmol) of phth-dPEG4-Tyr(O-methylene-triazole-ethane-N—BOC)OBn ester in 25 mL of methanol was placed into a 50 mL one-neck round bottom flask. Charcoal (1.45 g, 121 mmol, DARCO) and palladium acetate (0.29 g, 1.29) were added to this solution and obtained mixture was purged with nitrogen following purging with hydrogen (H2 filled balloon was used). The reaction stirred vigorously under hydrogen filled balloon pressure at ambient temperature overnight. After completion of the reaction, charcoal was removed by filtration over celite, cake washed with dichloromethane (3×30 mL) and combined clear filtrate was concentrated under reduced pressure to give 2.8 g of white foam. This crude was purified by chromatography on silica gel using dichloromethane/methanol as eluent with gradient from 0% to 10% methanol. Pure fractions were collected and concentrated under reduced pressure to give 1.68 g (62% yield) of product as white foam.

$^1$HNMR (400 MHz, CDCl$_3$, δ): 7.75 and 7.63 (2m, 4H, phthalimido), 7.56 (s, 1H, triazole), 7.03 and 6.78 (2d, CH, tyrosine), 6.93 (m, 1H, NH), 5.20-5.011 (m, 3H, benzyl, O—CH2-triazole), 4.69 (m, 1H, N—CH—CO), 4.40 (t, 2H, CH2-triazole), 3.80 (t, 2H, CH2), 3.64 (t, 2H, CH2-N-phthalimido), 3.62-3.40 (m, 16H, CH2O), 3.00 (dddd, 2H, CH2-C6H4-O), 2.40 (m, 2H, CH2CO).

6. PhthN-dPEG$_4$-Tyr(O-methylene-triazole-ethane-amidoyl-BOC)-m-dPEG$_{11}$ (PhthN-dPEG$_4$-(Tyr-OCH$_2$CH$_2$-triazole-CH$_2$CH$_2$—NH-t-boc)-NH-m-dPEG$_{11}$)

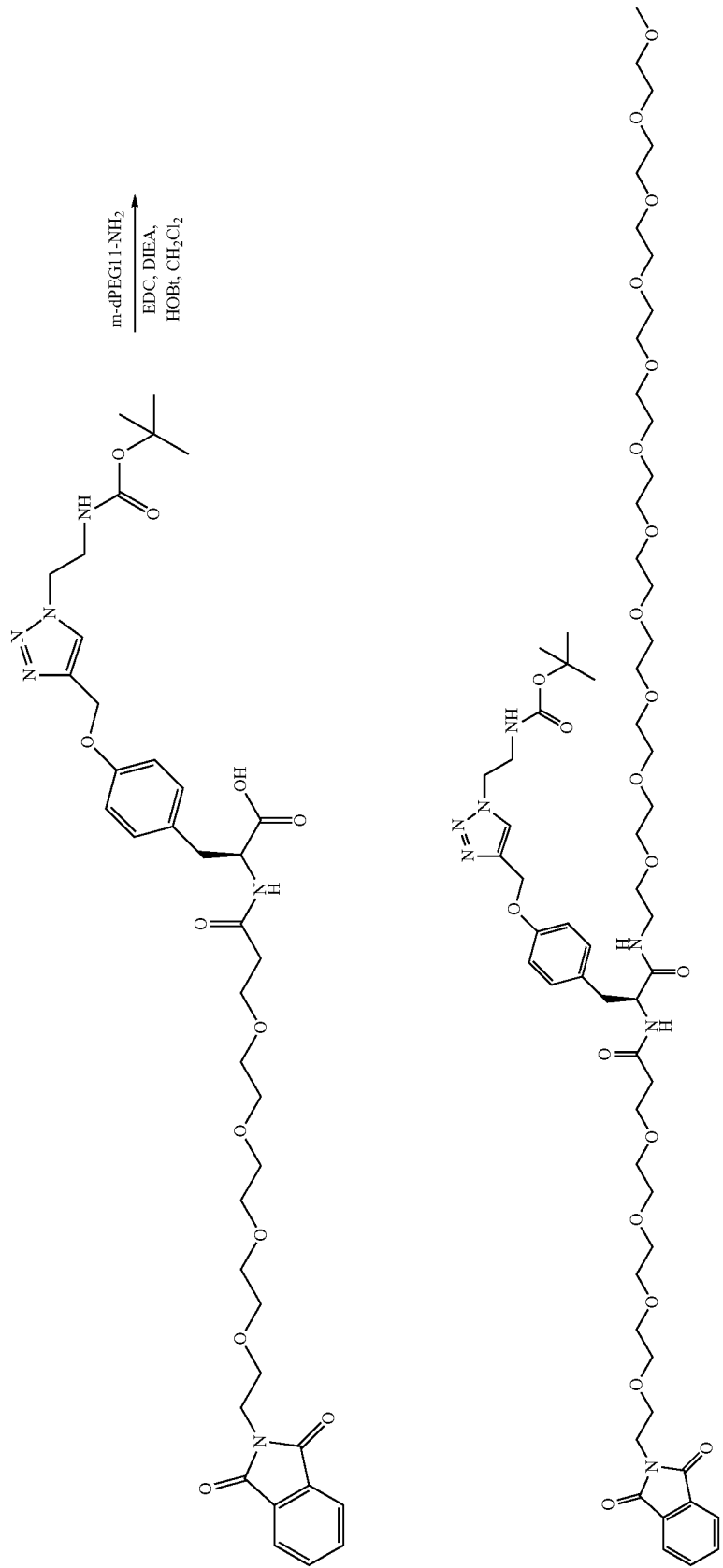

A mixture of m-dPEG11-NH₂ (1.105 g, 2.143 mmol), diisopropylethyl amine (0.72 g, 5.57 mmol) and HOBt (0.092 g, 0.681 mmol) in 25 mL of anhydrous dichloromethane was placed in a 100 mL one-neck round bottom flask equipped with a magnetic stirrer, thermocouple, N2-filled balloon, and cooling ice-MeOH bath. Obtained solution was cooled to 0° C., and a solution of phth-dPEG4-Tyr(O-methylene-triazole-ethane-N—BOC)acid (1.62 g, 2.069 mmol) in 10 mL of anhydrous dichloromethane was added via syringe. The reaction stirred for 10 min, and allowed to warm up to ambient temperature and stirred for 6 hrs. Obtained mixture was quenched with cold saturated NH4Cl (3×30 mL), organic bottom phase was separated and top aqueous layer was extracted with dichloromethane (2×30 ml). Combined organic extracts were dried over anhydrous sodium sulfate and concentrated under reduced pressure to give 4.34 g of clear viscous oil. This crude was purified by chromatography on silica gel using dichloromethane/methanol as eluent with gradient from 0% to 15% methanol. Pure fractions were collected and concentrated under reduced pressure to give 2.63 g (99% yield) of product as clear oil.

¹HNMR (400 MHz, CDCl₃, δ): 7.81 and 7.69 (2m, 4H, phthalimido), 7.63 (s, 1H, triazole), 7.11 and 6.87 (2d, 4H, tyrosine), 6.92 (d, 1H, NH), 6.60 (s, 1H, NH), 6.74 (m, 1H, NH), 5.15 (s, 2H, O—CH2-triazole), 5.04 (broad s, 1H, NH—BOC), 4.57 (q, 1H, N—CH—CO), 4.47 (t, 2H, CH2-triazole), 3.86 (t, 2H, CH2-N-phtalimido), 3.70 (t, 2H, CH2N), 3.68-3.42 (m, 60H, CH2O, and CH2N), 2.98 (dddd, 2H, CH2-C6H4-O), 2.42 (t, 2H, CH2CO), 1.41 (s, 9H, t-Bu).

t-boc-NH-dPEG₄-CO-Tyr-OBn

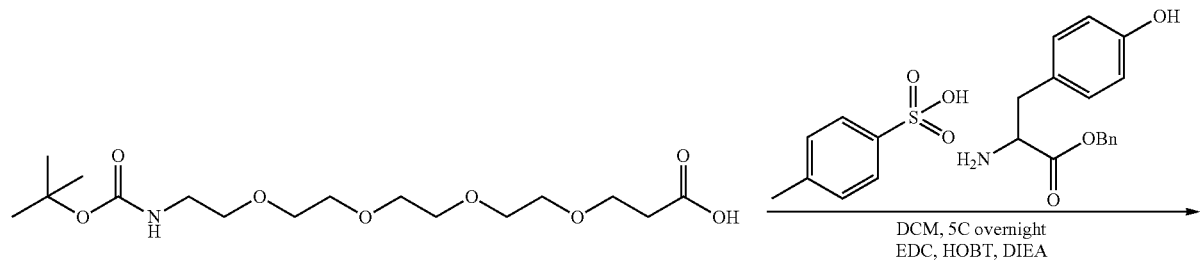

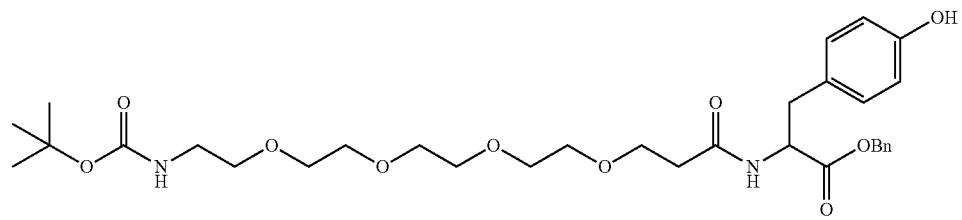

A 250 mL 4-neck round bottom flask was charged with magnetic stir bar, thermo probe, boc-dPEG₄-acid (34.3 g, 94 mmol) dissolved in anhydrous CH₂Cl₂ (250 mL), HOBT (2.61 g, 17.1 mmol), diisopropyethyl amine (DIEA, 13.23 g, 102 mmol), and benzyl ester of tyrosine tosylate salt (37.8 g, 85.0 mmol). The suspension was cooled to 5° C. in an ice/water bath. Solid coupling reagent (EDC, 24.54 g, 128 mmol) was added to this suspension portion wise. The ice/water bath was removed and the reaction was allowed to warm to room temperature overnight. The reaction was monitored by TLC (in CH₂Cl₂/MeOH=9/1) and after it was complete it was washed with water (4×30 mL). The organic layer was dried over magnesium sulfate and filtered over a bed of celite (10 g). The CH₂Cl₂ was removed under reduced pressure to give 52 g (98%) of product as viscous oil.

¹H NMR (400 MHz, CDCl₃, δ): 7.29 (m, 5H, benzyl), 6.94 (s, 1H, NH), 6.78 (d, 2H, tyrosine), 6.68 (d, 2H, tyrosine), 5.23 (s, 1H, CH₂OCO), 5.20 (s, 1H, NH), 5.07 (m, 2H, OCH₂CO), 4.85 (m, 1H, CHN), 3.58 (m, 16H, CH₂O), 2.98 (d, 2H, CH₂N), 2.42 (m, 2H, CH₂), 2.48 (m, 2H, CH₂CO), 1.36 (s, 9H, CH₃)

t-boc-NH-dPEG$_4$-CO-Tyr(-OTBA)-OBn (OTBA=—CH$_2$—COO-t-butyl)

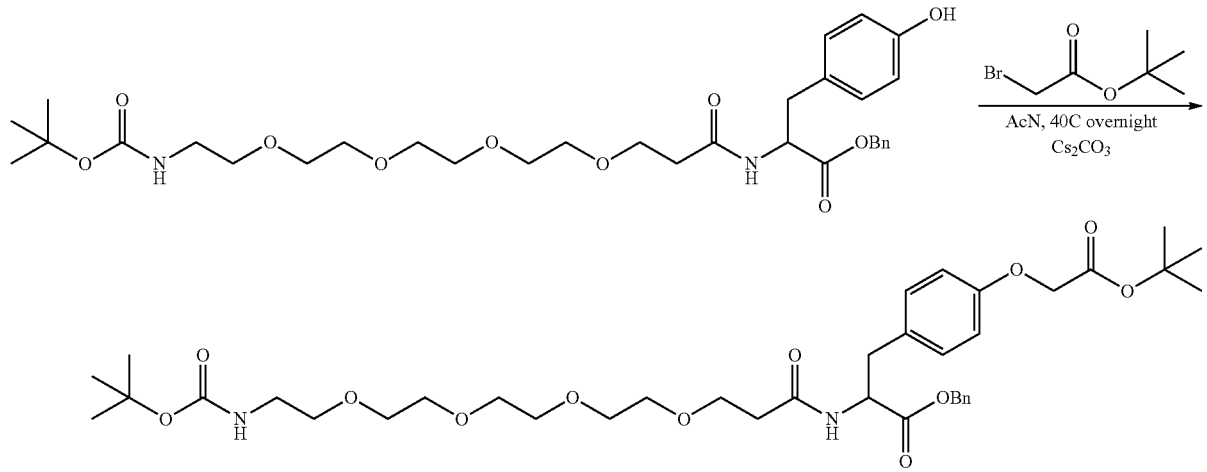

A 500 mL 4-neck round bottom flask was charged with boc-dPEG$_4$-tyr(OH)-OBn (53 g, 86 mmol) dissolved in acetonitrile (300 mL). To the flask, solid Cs$_2$CO$_3$ (56 g, 172 mmol) was added in one portion followed by t-butyl bromoacetate addition (25 g, 128 mmol) via syringe. The reaction was heated to 40° C. and held for 15 hours. The reaction was monitored by TLC (CH$_2$Cl$_2$/MeOH=9.5/0.5). After the reaction was complete, acetonitrile was removed under reduced pressure. The crude material was dissolved in CH$_2$Cl$_2$ (300 mL) and washed with 10% brine solution (2×100 mL). The organic layer was separated, dried over magnesium sulfate and concentrated under reduced pressure to give 57 g (91% yield) of product as viscous amber oil.

$^1$H NMR (400 MHz, CDCl$_3$, δ): 7.30 (m, 5H, benzyl), 7.11 (d, 2H, tyrosine), 7.07 (s, 1H, NH) 6.80 (d, 2H, tyrosine), 5.23 (s, 1H, CH$_2$OCO), 5.20 (s, 1H, NH), 4.80 (m, 1H, CHN), 4.47 (s, 2H, OCH$_2$CO), 3.58 (m, 16H, CH$_2$O), 3.29 (m, 2H, CH$_2$N), 3.18 and 3.05 (m, 2H, CH$_2$), 2.48 (m, 2H, CH$_2$CO), 1.48 (s, 9H, CH$_3$), 1.44 (s, 9H, CH$_3$)

t-boc-NH-dPEG$_4$-CO-Tyr(-OTBA)-OH

A 500 mL 4-neck round bottom flask was charged with Boc-dPEG$_4$-tyr(OTBA)-OBn (54 g, 73.7 mmol) dissolved in degassed MeOH (300 mL) and purged with nitrogen. Palladium acetate (0.9 g, 4.0 mmol) and charcoal (11 g, 916 mmol) were weighed in the dry box and added to the flask. Hydrogen gas was bubbled into the reaction via syringe. After 3 hours, TLC (CH$_2$Cl$_2$/MeOH=9/1) indicated the completion of the reaction. The mixture was filtered over a celite bed (20 g) in a fritted glass funnel and the cake washed with MeOH (3×50 mL). The MeOH was removed under reduced pressure at 30° C. The crude was purified on silica gel (750 g column) using gradient elution with CH$_2$Cl$_2$/MeOH. Pure fractions were combined and concentrated under reduced pressure. Yield: 33 g (69%) viscous yellow oil.

$^1$H NMR (400 MHz, CDCl$_3$, δ): 7.11 (d, 2H, tyrosine), 7.07 (s, 1H, NH) 6.80 (d, 2H, tyrosine), 5.20 (s, 1H, NH), 4.80 (m, 1H, CHN), 4.47 (s, 2H, OCH$_2$CO), 3.58 (m, 16H, CH$_2$O), 3.29 (m, 2H, CH$_2$N), 3.18 and 3.05 (m, 2H, CH$_2$), 2.48 (m, 2H, CH$_2$CO), 1.48 (s, 9H, CH$_3$), 1.44 (s, 9H, CH$_3$)

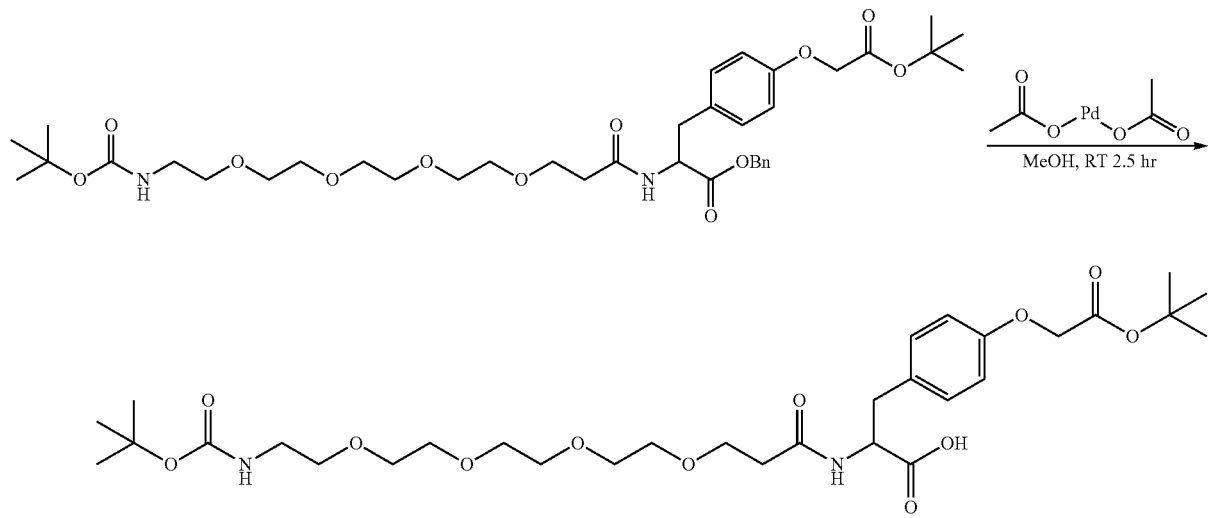

t-boc-NH-dPEG$_4$-CO-Tyr(-OTBA)-TFP ester

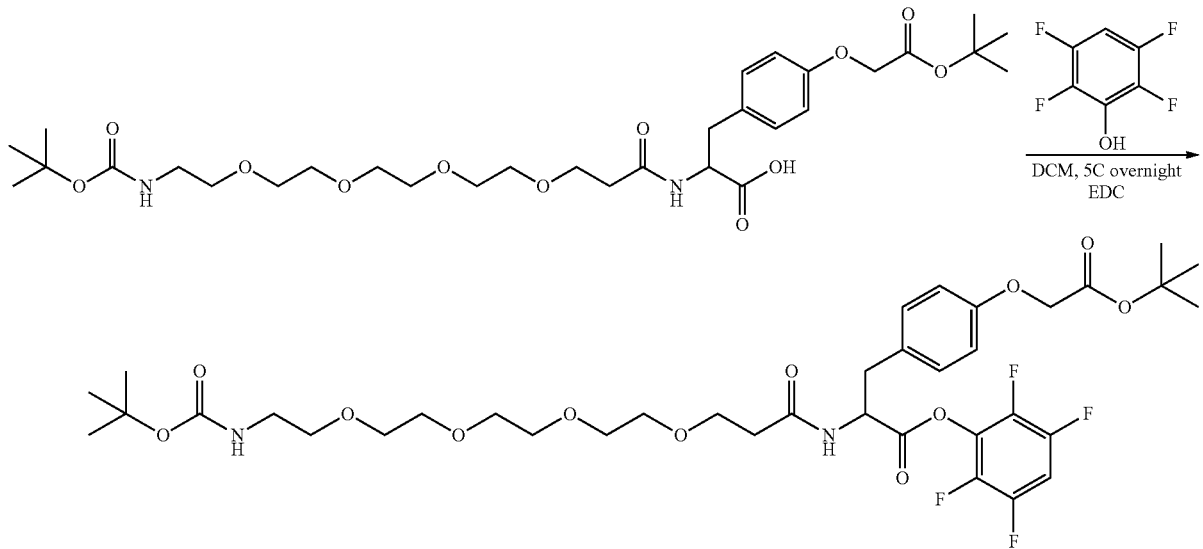

A 250 mL 4-neck round bottom flask was charged with magnetic stir bar, thermo probe, t-boc-NH-dPEG$_4$-CO-Tyr(-OTBA)-OH (10 g, 15.56 mmol) dissolved in CH$_2$Cl$_2$ (40 mL) and cooled to 5° C. in an ice/water bath. The tetrafluorophenol (TFP, 3.36 g, 20.23 mmol) and EDC (4.47 g, 23.34 mmol) were weighed in the dry box and the TFP was added to the flask followed by EDC in one portion as a solid. The ice bath was removed and the reaction warmed to room temperature and stirred for 15 hours. By TLC (CH$_2$Cl$_2$/MeOH=9/1) the starting material was completely consumed and the reaction was washed with cold water (2×10 mL) and saturated brine (10 mL). After drying over magnesium sulfate for one hour, the solution was filtered and concentration under reduced pressure the product (11.5 g, 89.5% yield) was obtained as yellow, viscous oil.

$^1$H NMR (400 MHz, CDCl$_3$, δ): 7.11 (d, 2H, tyrosine), 7.11 (s, 1H, NH) 7.03 (m, 1H, TFP) 6.86 (d, 2H, tyrosine), 5.20 (s, 1H, NH), 4.80 (m, 1H, CHN), 4.47 (s, 2H, OCH$_2$CO), 3.58 (m, 16H, CH$_2$O), 3.29 (m, 2H, CH$_2$N), 3.18 and 3.05 (m, 2H, CH$_2$), 2.48 (m, 2H, CH$_2$CO), 1.48 (s, 9H, CH$_3$), 1.44 (s, 9H, CH$_3$)

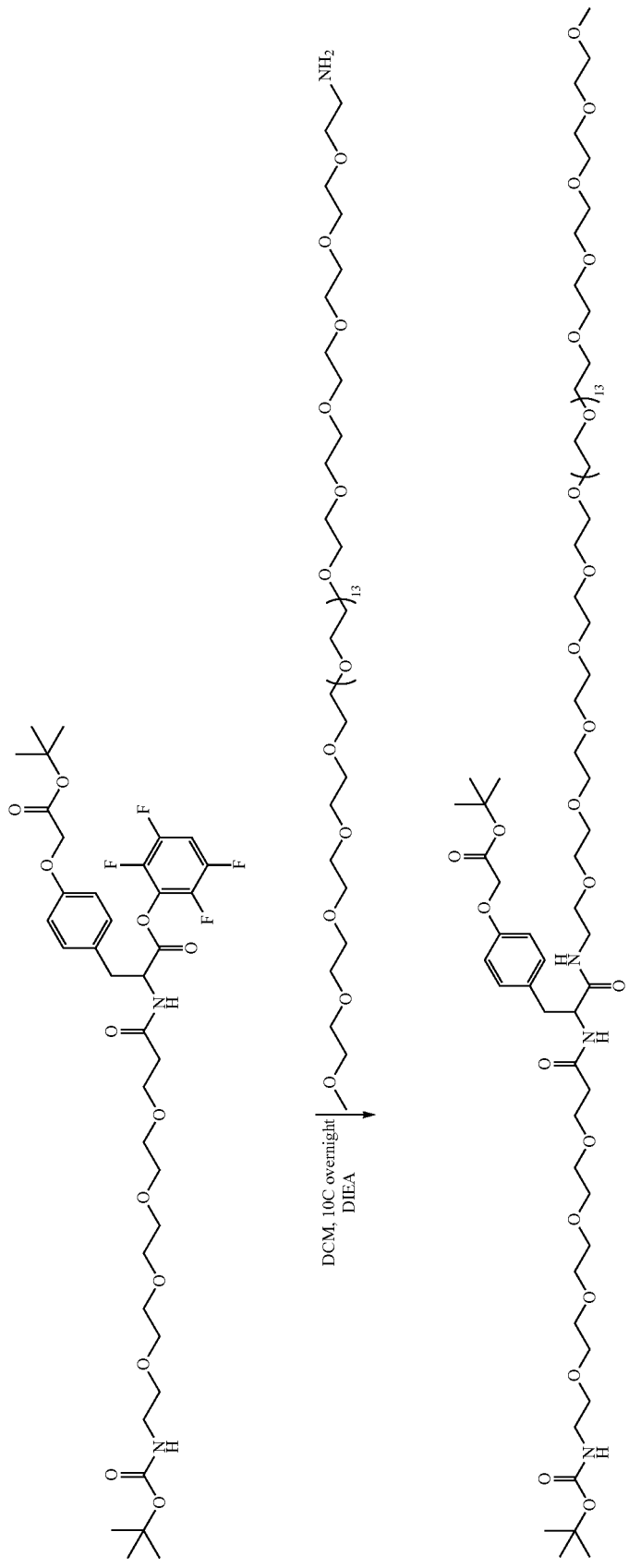

A 100 mL 4-neck round bottom flask was charged with t-boc-NH-dPEG$_4$-CO-Tyr(-OTBA)-TFP ester (5.05 g, 6.39 mmol) and m-dPEG$_{24}$-amine (7.64 g, 7.02 mmol) dissolved in CH$_2$Cl$_2$ (30 mL). The flask was cooled to 10° C. using an ice/water bath. The DIEA (1.24 g, 9.58 mmol) was added drop wise via syringe. Once all DIEA was added the ice/water bath was removed and the reaction was allowed to warm to room temperature and stir for 15 hours. The reaction was complete by TLC (CH$_2$Cl$_2$/MeOH=9/1). The reaction was washed with water (3×10 mL), brine (10 mL) and dried over magnesium sulfate. The solution was filtered and was concentrated under reduced pressure. Yield: 8.4 g (77% yield) as light amber oil.

$^1$H NMR (400 MHz, CDCl$_3$, δ): 7.12 and 6.80 (2d, 4H, aromatic, tyrosine), 6.91 (d, 1H, HNCO), 6.42 (m, 1H, HNCO), 5.21 (m, 1H, HNCO), 4.58 (m, 1H, NCHCO), 4.47 (s, 2H, OCH$_2$CO), 3.90-3.50 (m, 112H, CH$_2$O, CH$_2$N), 3.38 (s, 3H, CH$_3$O), 3.00 (m, 2H, CH$_2$ in tyrosine), 2.43 (t, 2H, CH$_2$CO), 1.48 (s, 9H, t-Bu), 1.32 (s, 9H, t-Bu).

NH$_2$-dPEG$_4$-CO-Tyr(-OTAA)-NH-m-dPEG$_{24}$
(OTAA=—CH$_2$—COOH)

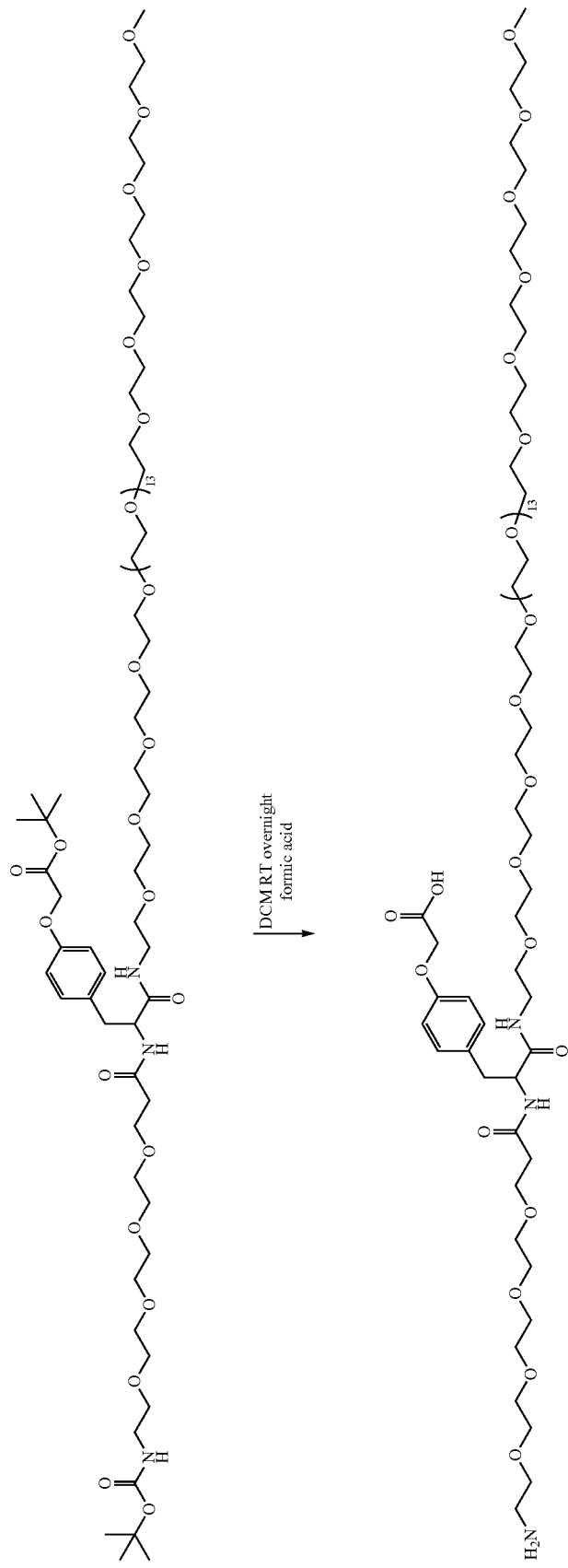

A 100 mL 4-neck round bottom flask was charged with magnetic stir bar, thermo probe, t-boc-NH-dPEG$_4$-CO-Tyr(-OTBA)-NH-m-dPEG$_{24}$ (8.4 g, 4.90 mmol) dissolved in CH$_2$Cl$_2$ (6 mL). Formic acid (12.00 g, 261 mmol) was added via syringe drop wise. The reaction was heated to 30° C. for 15 hours and was monitored by TLC (CH$_2$Cl$_2$/MeOH=9/1). After the reaction was complete, it was concentrated and triturated with CH$_3$OBu-t (MTBE, 150 mL). The obtained semisolid was dissolved in CH$_2$Cl$_2$ (25 mL) and concentrated under reduced pressure. Yield: 6.5 g (83%) as light amber waxy solid.

$^1$H NMR (400 MHz, CDCl$_3$, δ): 7.12 and 6.80 (2d, 4H, aromatic, tyrosine), 6.91 (d, 1H, HNCO), 6.45 (m, 1H, HNCO), 4.60 (m, 1H, NCHCO), 4.47 (s, 2H, OCH$_2$CO), 3.90-3.50 (m, 112H, CH$_2$O, CH$_2$N), 3.38 (s, 3H, CH$_3$O), 3.00 (m, 2H, CH$_2$ in tyrosine), 2.43 (t, 2H, CH$_2$CO), 2.24 (broad m, 2H, NH$_2$).

t-boc-NH-dPEG$_4$-CO-Tyr(-OTBA)-NH-dPEG$_4$-CO-Tyr(-OAA)-NH-m-dPEG$_{12}$

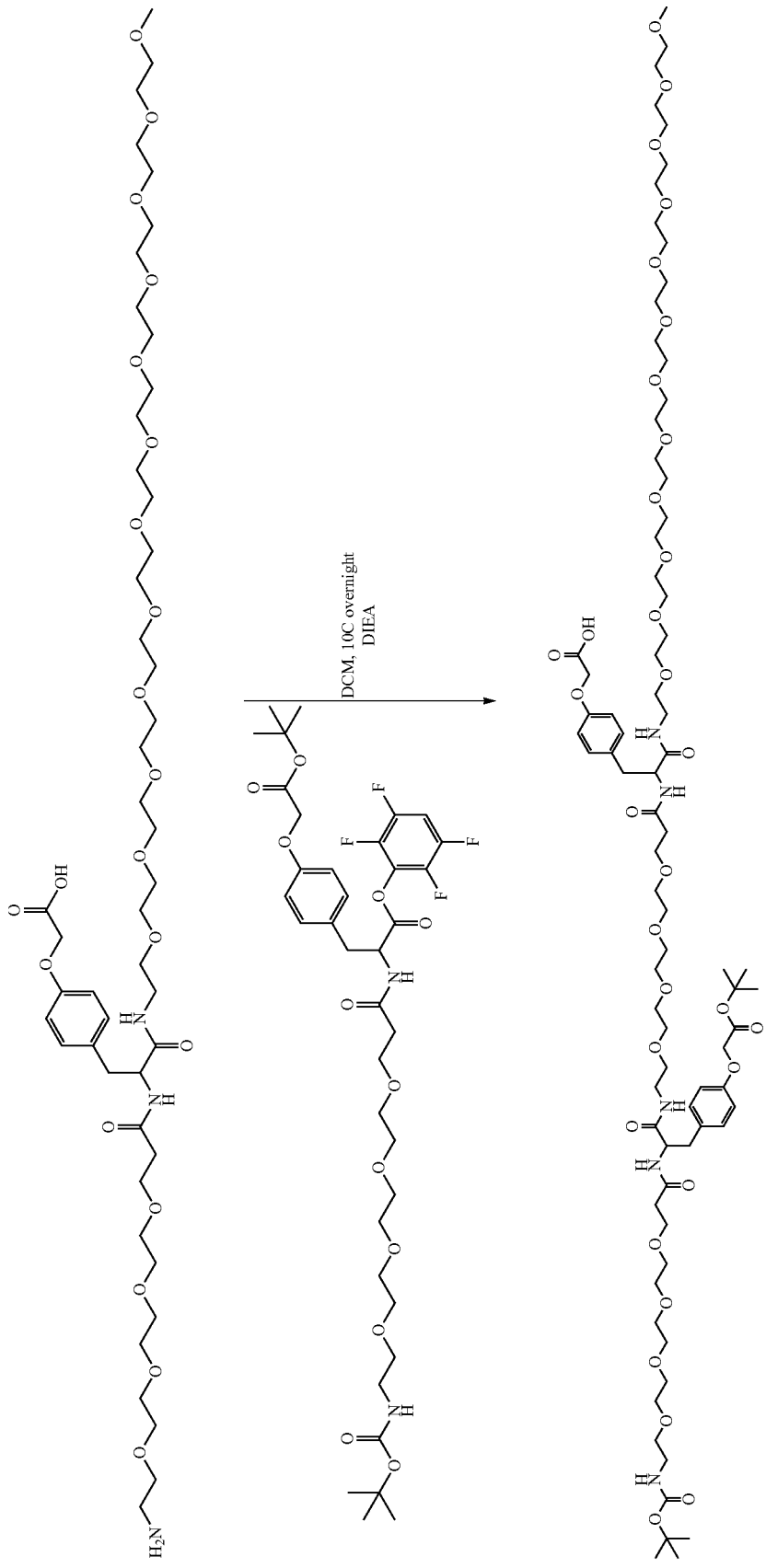

To a 50 mL 3-neck round bottom flask charged with a magnetic stir bar, thermo probe, $NH_3^+Cl^-$-dPEG$_4$-CO-Tyr(-OAA)-NH-m-dPEG$_{12}$ (3.8 g, 3.57 mmol) and t-boc-NH-dPEG$_4$-CO-Tyr(-OTBA)-TFP ester (2.82 g, 3.57 mmol) dissolved in $CH_2Cl_2$ (10 mL) were added. The flask was cooled using an ice/water bath to 5° C. The DIEA (1.25 g, 9.71 mmol) was added via syringe drop wise. The reaction required 44 hours for completion by TLC ($CH_2Cl_2$/MeOH=9/1). The reaction was washed with water (5 mL) and with brine (5 mL), and concentrated. The product was triturated in MTBE (75 mL) and obtained oil was dissolved in DCM (15 mL) and concentrated under reduced pressure to give 3 g (51% yield) of product as yellow oil.

$^1$H NMR (400 MHz, CDCl$_3$, δ): 7.03 and 6.83 (2d, 8H, aromatic, tyrosine), 6.94 (broad m, 2H, HNCO), 6.63 (m, 2H, HNCO), 4.52 (m, 2H, NCHCO), 4.52 (s, 4H, OCH$_2$CO), 3.94-3.45 (m, 82H, CH$_2$O, CH$_2$N), 3.41 (s, 3H, CH$_3$O), 3.12 (m, 4H, CH$_2$ in tyrosine), 2.38 (t, 4H, CH$_2$CO), 1.47 (s, 9H, t-Bu).

$NH_3^+Cl^-$-dPEG$^4$-CO-Tyr(-OTAA)-NH-dPEG$_4$-CO-Tyr(-OAA)-NH-m-dPEG$_{12}$

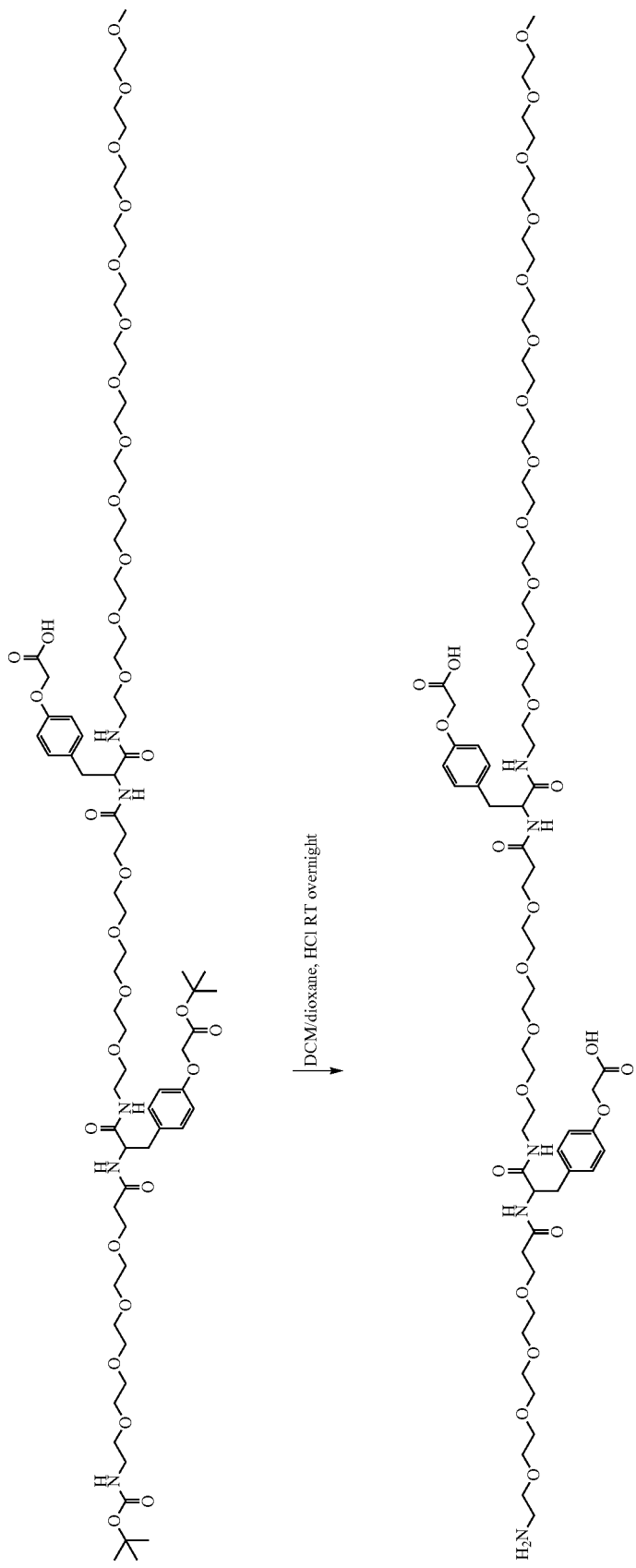

To a 50 mL 3-neck round bottom flask charged with a magnetic stir bar, thermo probe, HCl (4M in dioxane) (6 mL, 24 mmol) was cooled to 10° C. via ice/water bath. The t-boc-NH-dPEG$_4$-CO-Tyr(-OTBA)-dPEG$_4$-CO-Tyr(-OAA)-NH-m-dPEG$_{12}$ (3 g, 1.82 mmol) was added as a solution in CH$_2$Cl$_2$ (6 mL) via syringe drop wise. The ice/water bath was removed and allowed to warm to room temperature. The reaction stirred for 15 hours and monitored by TLC (CH$_2$Cl$_2$/MeOH=9/1). After completion of the reaction, the mixture was concentrated under reduced pressure and triturated in MTBE (30 mL) The oily residue was dissolved in CH$_2$Cl$_2$ (25 mL) and concentrated under reduced pressure to give 2.58 g (93% yield) of product as yellow oil.

$^1$H NMR (400 MHz, CDCl$_3$, δ): 7.05 and 6.81 (2d, 8H, aromatic, tyrosine), 6.82 (broad m, 2H, HNCO), 6.58 (m, 2H, HNCO), 4.46 (m, 2H, NCHCO), 4.42 (s, 4H, OCH$_2$CO), 3.91-3.35 (m, 82H, CH$_2$O, CH$_2$N), 3.41 (s, 3H, CH$_3$O), 3.12 (m, 4H, CH$_2$ in tyrosine), 2.42 (t, 4H, CH$_2$CO).

NH$_2$-dPEG$^4$-CO-Tyr(-OTAA)-NH-dPEG$_4$-CO-Tyr(-OAA)-NH-m-dPEG$_{24}$

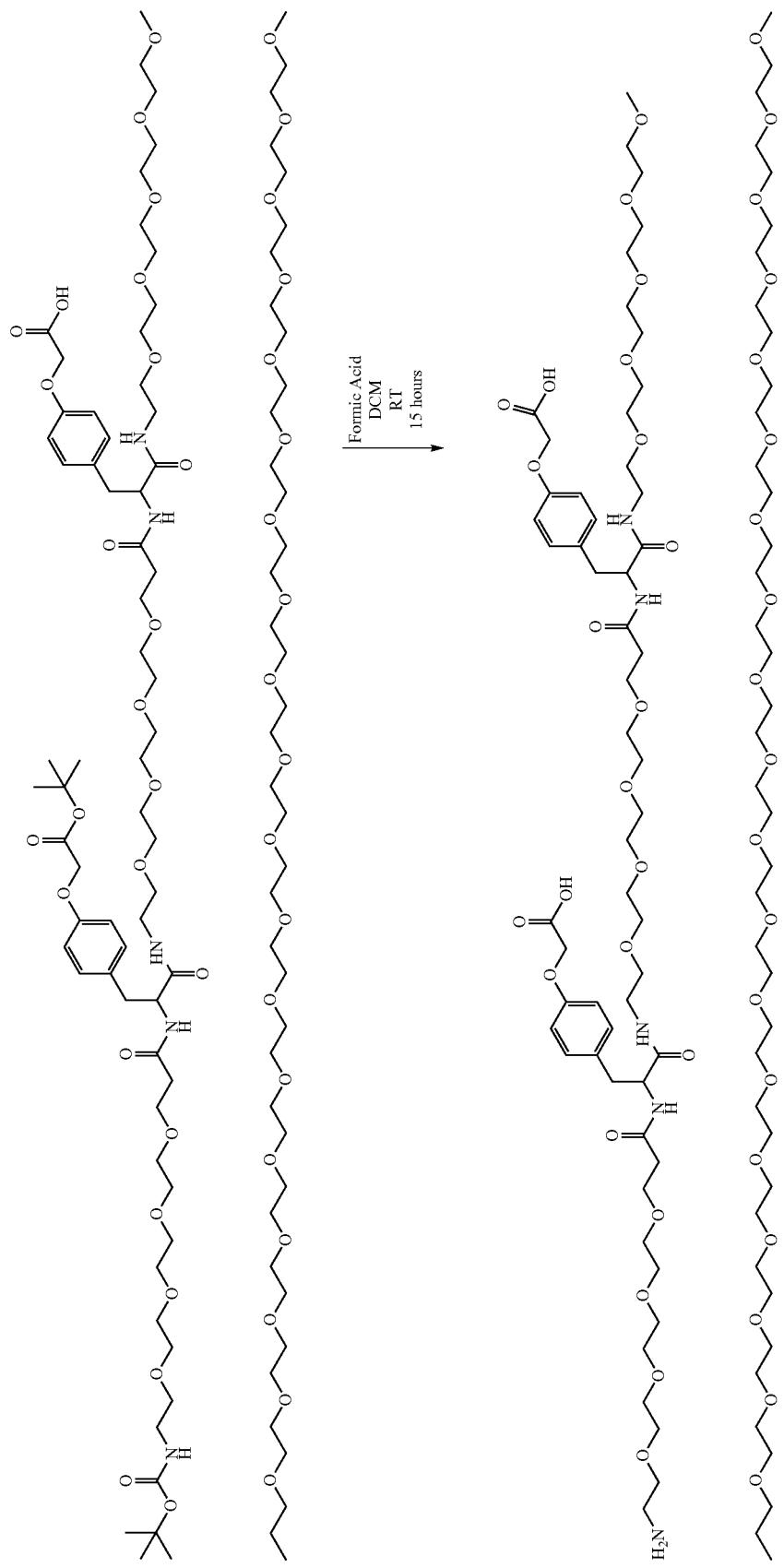

A 250 mL 4-neck round bottom flask was charged with a solution of t-boc-NH-dPEG$_4$-CO-Tyr(-OTBA)-dPEG$_4$-CO-Tyr(OAA)-NH-m-dPEG$_{24}$ (6.8 g, 3.12 mmol) in 7 mL of CH$_2$Cl$_2$. The flask was cooled to 5° C. using an ice/water bath. To the flask formic acid (11.96 mL, 312 mmol) was added drop wise via syringe. The reaction ran for 15 hours. The reaction was monitored via TLC (CH$_2$Cl$_2$/MeOH 9/1). After 15 hours TLC showed completion. The resultant material was concentrated under pressure. It was then taken up in 75 mL MTBE and stirred for 30 minutes twice. The product was then dissolved in 10 mL DCM and dried under reduced pressure. Yield: 4.99 g, 79% amber viscous oil.

$^1$H NMR (400 MHz, CDCl$_3$, δ): 7.64 (d, 2H, HNCO), 7.14 (m, 2H, HNCO), 7.11 and 6.85 (2d, 8H, aromatic, tyrosine), 4.66 (m, 2H, NCHCO), 4.51 (s, 4H, OCH$_2$CO), 3.90-3.40 (m, 135H, CH$_2$O), 3.47 (s, 3H, CH$_3$O), 3.02-2.80 (m, 6H, CH$_2$ in tyrosine, and CH$_2$NH$_2$), 2.42 (m, 4H, CH$_2$CO).

t-boc-NH-dPEG$_4$-CO-Tyr(-OTBA)-NH-dPEG$_4$-CO-Tyr(-OAA)-NH-dPEG$_4$-CO-T OAA)-NH-m-dPEG$_{12}$

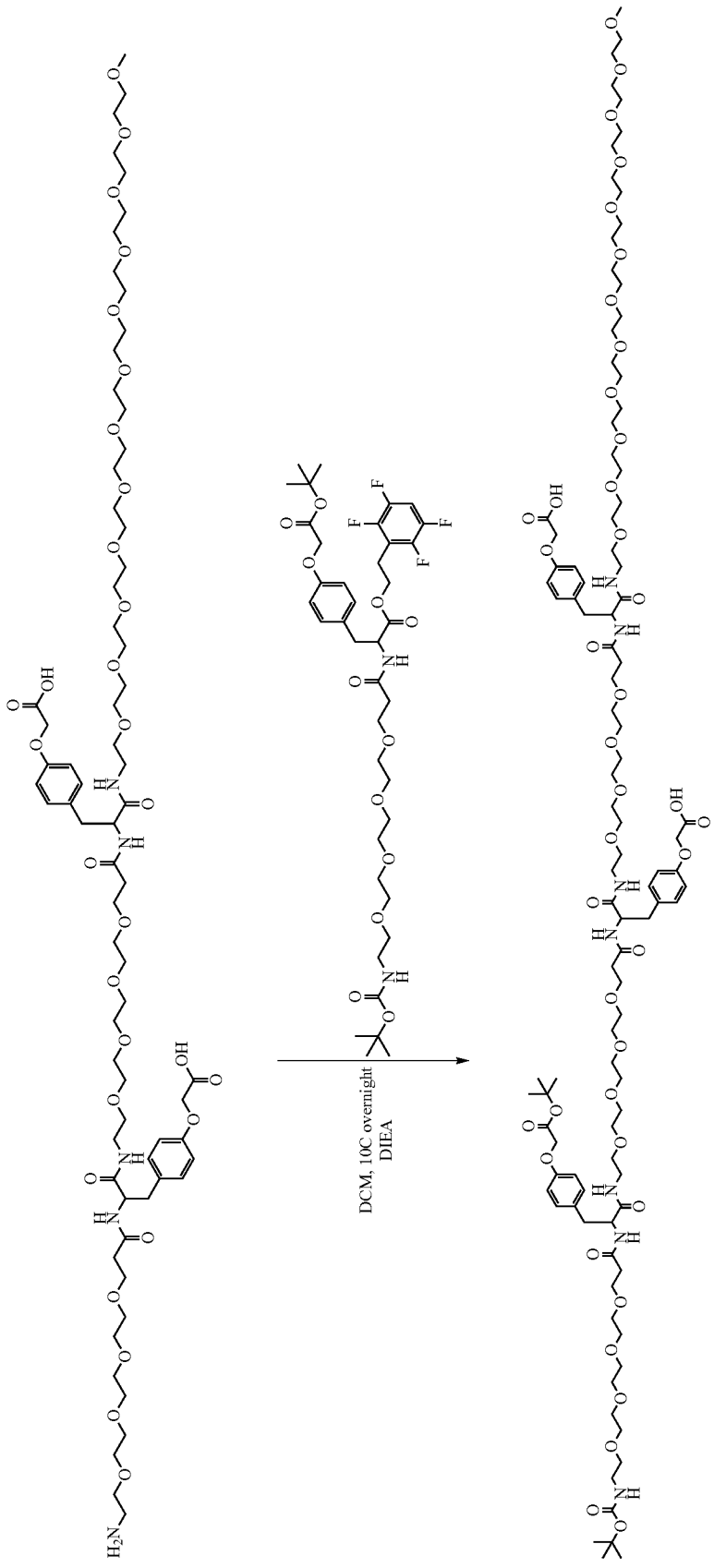

To a 50 mL 3-neck round bottom flask a mixture of $NH_3^+Cl^-$-dPEG$_4$-CO-Tyr(-OAA)-dPEG$_4$-CO-Tyr(-OAA)-NH-m-dPEG$_{12}$ (2.50 g, 1.63 mmol) and t-boc-NH-dPEG$_4$-CO-Tyr(-OTBA)-TFP ester (1.41 g, 1.78 mmol) as a solution in $CH_2Cl_2$ (10 mL) was added and cooled to 5° C. in an ice/water bath. The DIEA (0.89 g, 6.89 mmol) was added via syringe. The cooling bath was removed and the reaction was allowed to warm to room temperature and stir for 15 hours. The reaction was monitored by TLC ($CH_2Cl_2$/MeOH=9/1). The reaction was washed with water (5 mL) and with brine (5 mL), concentrated, and then triturated in MTBE (35 mL). The oily residue was re-dissolved in $CH_2Cl_2$ (15 mL) and concentrated under reduced pressure to give 2.7 g (78% yield) of product. $^1$H NMR (400 MHz, CDCl$_3$, δ): 7.13 and 6.92 (2m, 12H, aromatic, tyrosine), 6.94 (broad m, 3H, HNCO), 6.72 (m, 3H, HNCO), 5.12 (m, 1H, HNCO), 4.52 (m, 3H, NCHCO), 4.63 (s, 6H, OCH$_2$CO), 3.98-3.35 (m, 104H, CH$_2$O, CH$_2$N), 3.44 (s, 3H, CH$_3$O), 3.25-2.85 (m, 6H, CH$_2$ in tyrosine), 2.38 (t, 6H, CH$_2$CO), 1.48 (s, 9H, t-Bu).

t-boc-N H-d PEG$_4$-CO-Tyr(-OTBA)-NH-dPEG$_4$-CO-(Tyr-OAA)-NH-dPEG$_4$-CO-Tyr(-OAA)-NH-m-dPEG$_{24}$

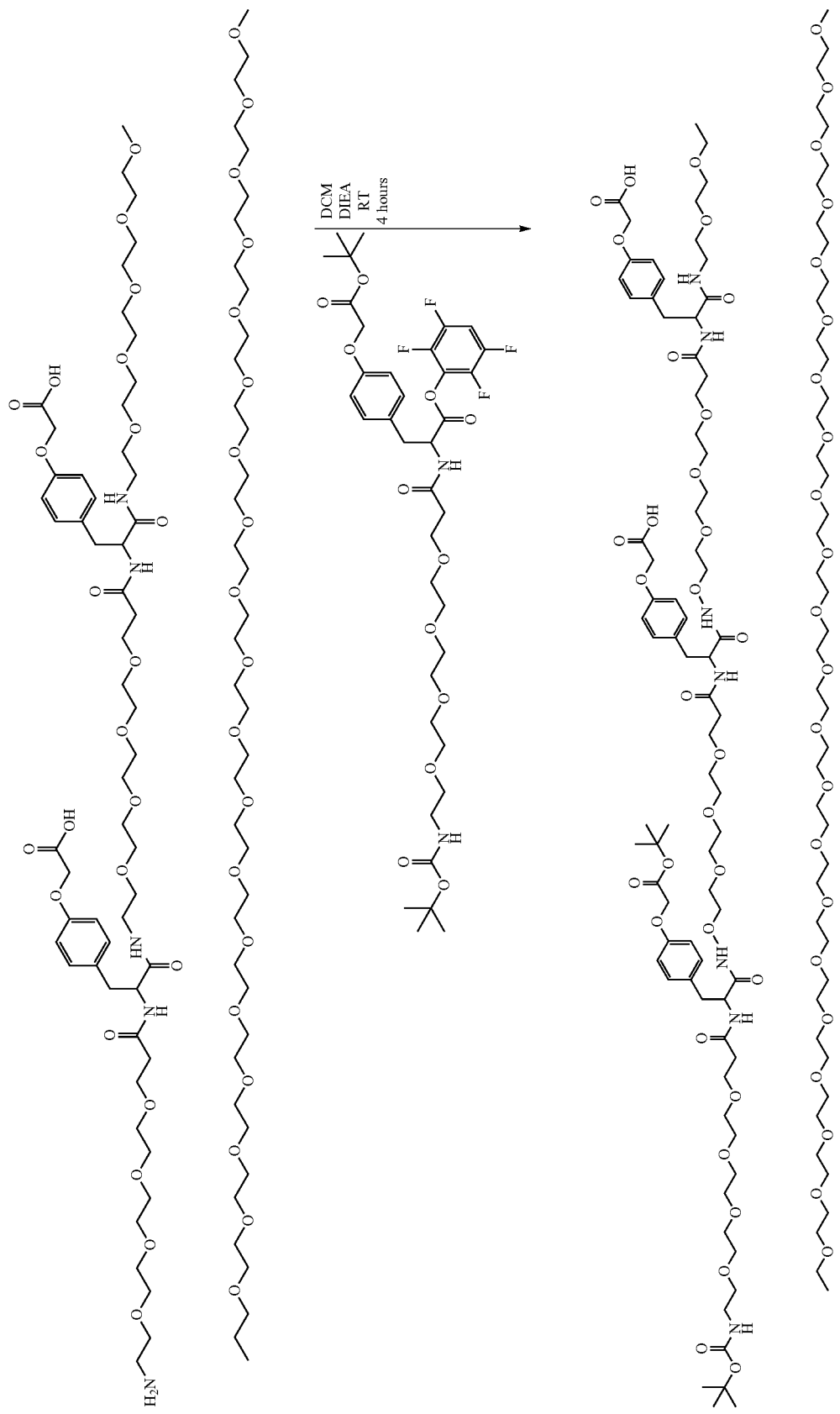

A 250 mL 1-neck round bottom flask is charged with $NH_3^+FA^--dPEG_4-CO-Tyr(-OAA)-dPEG_4-CO-Tyr(-OAA)-NH-m-dPEG_{24}$ (4.99 g, 2.46 mmol) in 10 mL $CH_2Cl_2$. To the flask DIEA (2.2 mL, 12.32 mmol) is added via syringe then t-boc-NH-dPEG$_4$-CO-Tyr(-OTBA)-TFP (2.05 g, 2.59 mmol) is dissolved in 5 mL $CH_2Cl_2$ and added drop wise via syringe. The reaction is let stir for 4 hours and checked via TLC ($CH_2Cl_2$/MeOH 9/1) which showed complete consumption of the starting material. The material was then washed with water (3×5 mL) and then dried over sodium sulphate and filtered. The resultant material is then concentrated under reduced pressure then 50 mL MTBE was added and stirred. The MTBE was then decanted and 15 mL $CH_2Cl_2$ was added and then concentrated under reduced pressure. Yield: 5 g, 77% amber viscous liquid.

$^1$H NMR (400 MHz, CDCl$_3$, δ): 7.22 (d, 1H, HNCO), 6.93 (m, 1H, HNCO), 7.11 and 6.80 (2d, 12H, aromatic, tyrosine, and 4H HNCO), 6.58 (m, 1H, HNCO), 4.60 (m, 3H, NCHCO), 4.47 (s, 6H, OCH$_2$CO), 3.90-3.40 (m, 142H, CH$_2$O), 3.39 (s, 3H, CH$_3$O), 3.02-2.80 (m, 6H, CH$_2$ in tyrosine), 2.42 (m, 6H, CH$_2$CO), 1.49 (s, 9H, t-Bu), 1.39 (s, 9H, t-Bu).

$NH_2-dPEG_4-CO-Tyr(-OAA)-NH-dPEG_4-CO-Tyr(-OAA)-NH-dPEG_4-CO-Tyr(-OAA)-NH-m-dPEG_{12}$

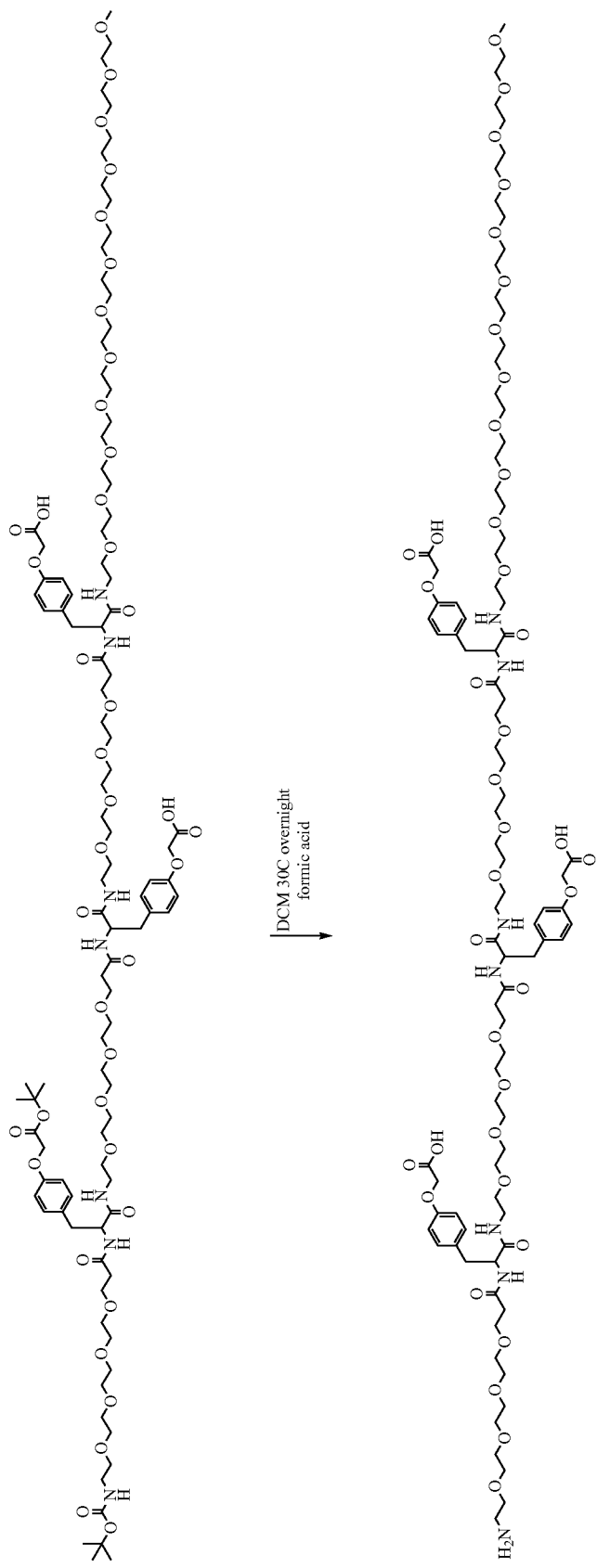

A solution of t-boc-NH-dPEG$_4$-CO-Tyr(-OTBA)-dPEG$_4$-CO-Tyr(-OAA)-dPEG$_4$-CO-Tyr(-OAA)-NH-m-dPEG$_{12}$ (2.7 g, 1.27 mmol) in CH$_2$Cl$_2$ (5 mL) was charged to a 50 mL 3-neck round bottom flask equipped with a thermocouple, magnetic stirrer, heating mantle and N$_2$-filled balloon. The formic acid (2.34 g, 50.9 mmol) was added via syringe drop-wise, and the reaction was heated at 30° C. for 30 hr. The reaction was complete according to TLC (CH$_2$Cl$_2$/MeOH=9/1), triturated with MTBE (2×30 mL), isolated oil was re-dissolved in CH$_2$Cl$_2$ and concentrated under reduced pressure to give 2.18 g (85% yield) of product as dark yellow oil.

$^1$H NMR (400 MHz, CDCl$_3$, δ): 7.25 and 6.83 (2m, 12H, aromatic, tyrosine), 6.87 (broad m, 3H, HNCO), 6.78 (m, 3H, HNCO), 4.52-4.46 (m, 9H, NCHCO, OCH$_2$CO), 3.86-3.46 (m, 104H, CH$_2$O, CH$_2$N), 3.52 (s, 3H, CH$_3$O), 3.36-2.92 (m, 6H, CH$_2$ in tyrosine), 2.41 (m, 6H, CH$_2$CO).

NH$_2$-dPEG$_4$-CO-Tyr(-OAA)-NH-dPEG$_4$-CO-Tyr(-OAA)-NH-dPEG$_4$-CO-Tyr(-OAA)-NH-m-dPEG$_{24}$:

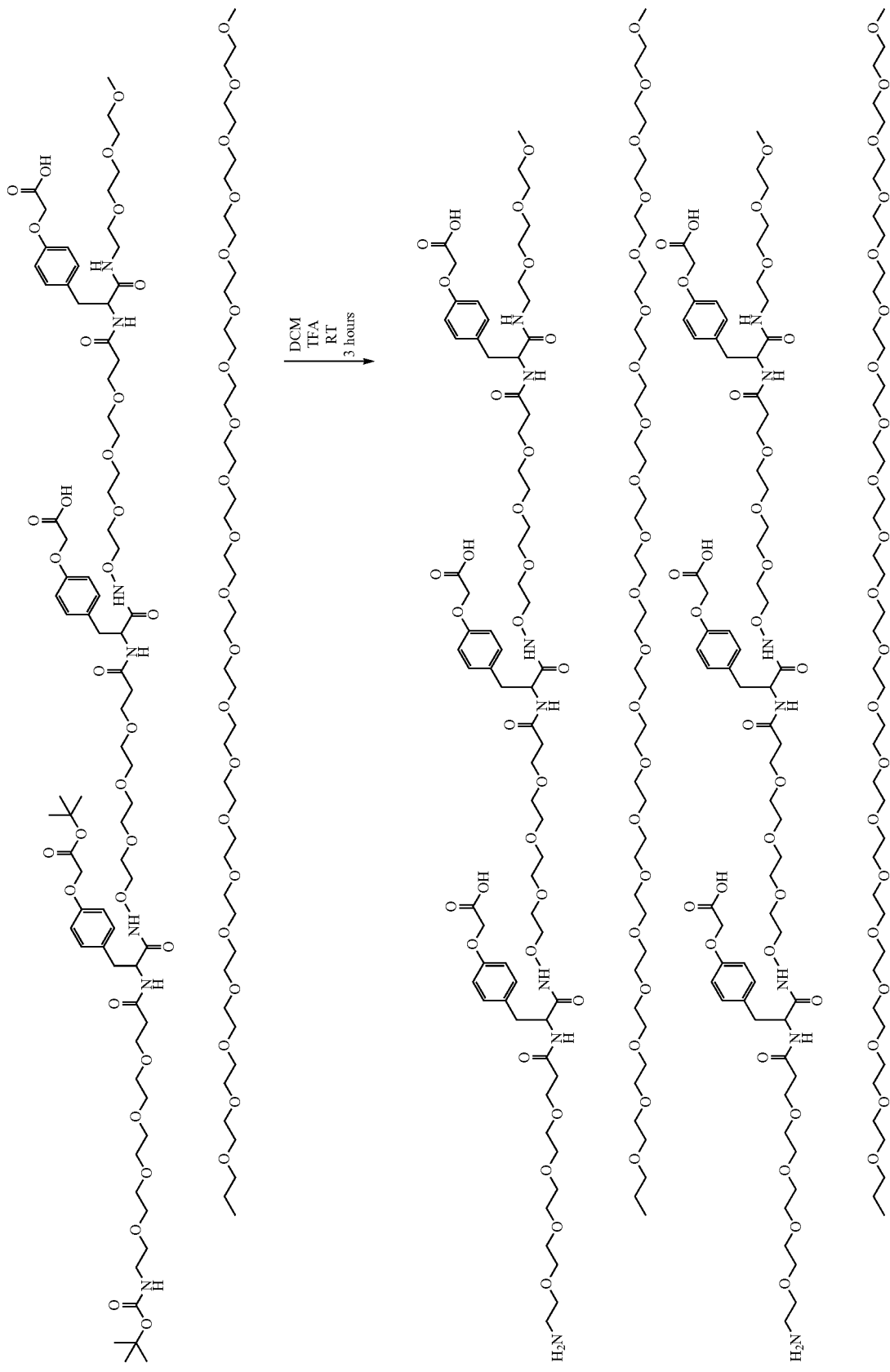

To a 100 mL 1-neck flask is charged with t-boc-NH-dPEG$_4$-CO-Tyr(-OTBA)-dPEG$_4$-CO-Tyr(-OAA)-dPEG$_4$-CO-Tyr(-OAA)-NH-m-dPEG$_{24}$ (5 g, 1.89 mmol) in 7 mL CH$_2$Cl$_2$. The flask is cooled to 5° C. in an ice/water bath. To the flask TFA (5 mL, 56.6 mmol) is added via syringe drop wise. The reaction was let stir for 3 hours and TLC (CH$_2$Cl$_2$/MeOH 9/1) was checked to show no starting material. The CH$_2$Cl$_2$ was removed under reduced pressure. The resultant viscous oil was stirred and 75 mL MTBE was added and decanted twice. To the flask 10 mL CH$_2$Cl$_2$ was added and then dried under reduced pressure. Yield: 2.9 g, 62% light amber viscous oil.

$^1$H NMR (400 MHz, CDCl$_3$, δ): 7.60-7.21 (m, 6H, HNCO), 7.01 and 6.72 (2d, 12H, aromatic, tyrosine), 4.54 (m, 12H, NCHCO and OCH$_2$CO), 3.90-3.40 (m, 142H, CH$_2$O), 3.47 (s, 3H, CH$_3$O), 3.02-2.80 (m, 8H, CH$_2$ in tyrosine, and CH$_2$NH$_2$), 2.42 (m, 6H, CH$_2$CO).

PhthN-dPEG$_4$(Tyr-OH)-OBn

Obtained solution was cooled to ~0° C., and coupling reagent EDC (72.7 g, 379 mmol) was added in one portion and the reaction was slowly allowed to warm to room temperature. The reaction was monitored by TLC (in CH$_2$Cl$_2$/MeOH=9/1), and after completion the solvent was removed under reduced pressure.

The residue was taken up in 1 L H$_2$O and extracted with EtOAc (3×100 mL). TLC indicated the product had been extracted. Extracts were washed with 10% HCl (1×200 mL), saturated aqueous NaHCO$_3$ (1×200 mL), brine (200 mL), dried over Na$_2$SO$_4$, filtered, and concentrated under reduced pressure to give 142.5 g of a viscous yellow oil.

The crude material was purified by silica plug (850 g of silica was used) using gradient elution with dichloromethane-ethanol with gradient from 100% CH$_2$Cl$_2$ to 90% CH$_2$Cl$_2$. After concentration of clean fractions the product (111.6 g, 68% yield) was obtained as viscous clear oil $^1$H NMR (400 MHz, CDCl$_3$, δ): 9.22 (s, 1H, OH), 8.22 (d, 1H, HNCO), 7.84 (m, 5H, phenyl), 7.26 (m, 4H, aromatic,

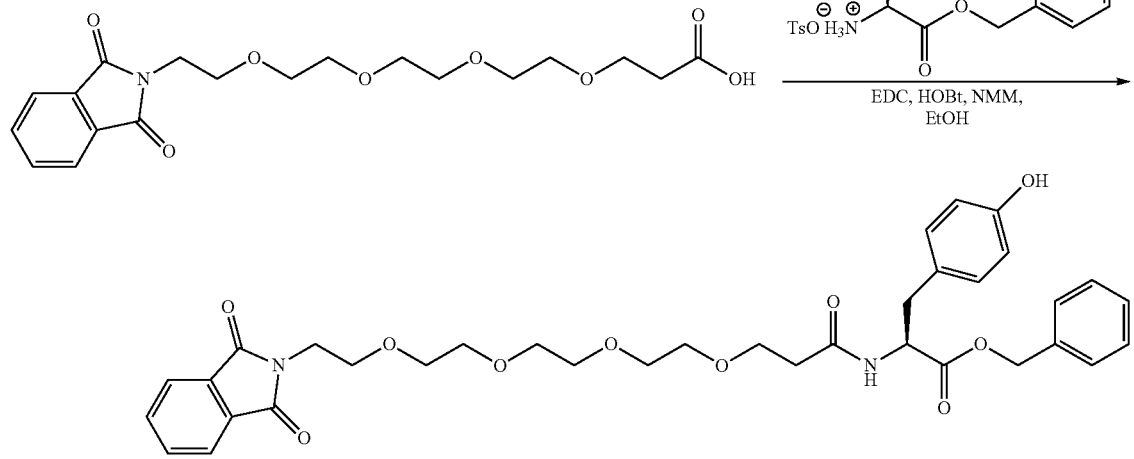

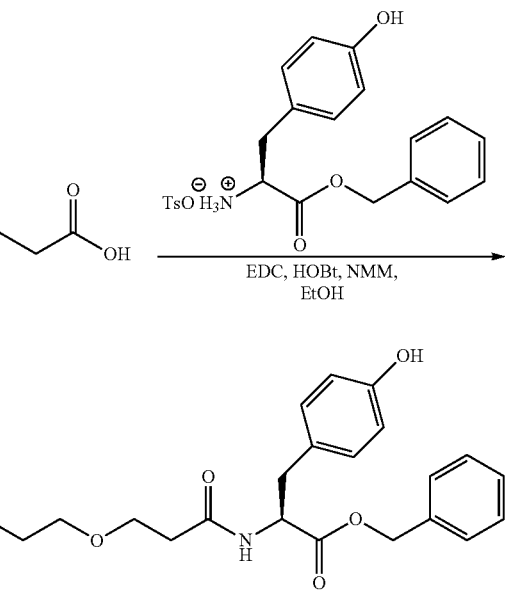

A mixture of PhthN-dPEG$_4$ acid (100 g, 253 mmol), M-methylmorpholine (82 g, 809 mmol), HOBt (6.41 g, 37.9 mmol) and benzyl ester of tyrosine tosylate (123 g, 278 mmol) in 1.5 L of 200 proof ethanol was charged in a 2 L 3-neck round bottom flask equipped with an overhead stirrer, thermocouple, N$_2$-filled balloon and cooling ice bath.

phthalimido), 7.00 and 6.66 (2d, 4H, aromatic, tyrosine), 5.00 (s, 2H, CH$_2$O), 4.48 (m, 1H, NCHCO), 3.90-3.50 (m, 18H, CH$_2$O, CH2N), 2.85 (m, 2H, CH$_2$ in tyrosine), 2.34 (t, 2H, CH$_2$CO).

PhthN-dPEG$_4$(Tyr-OTBA)-OBn

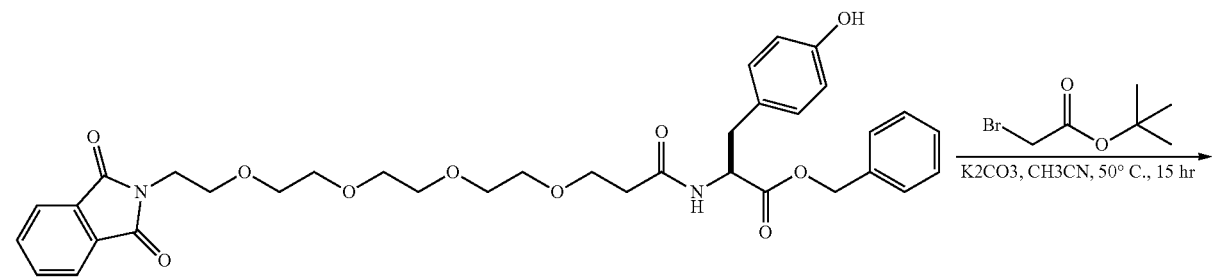

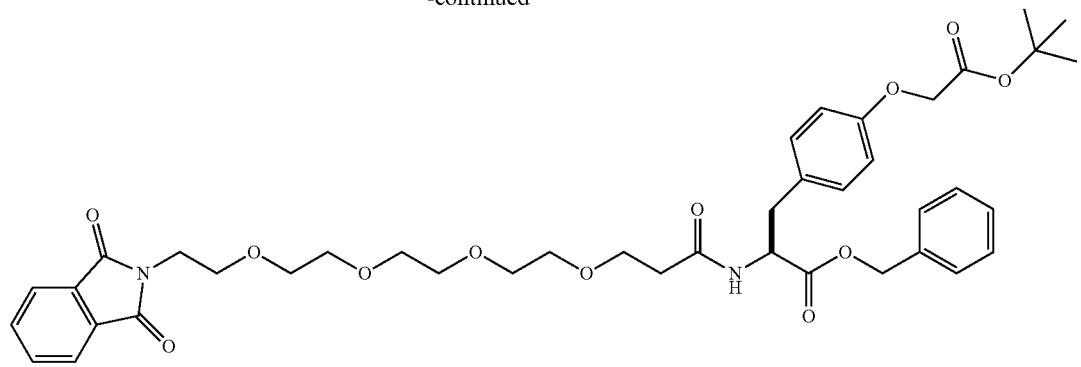

A mixture of Phth-dPEG4-(Tyr-OH)OBn ester (92.9 g, 143 mmol), anhydrous K$_2$CO$_3$ (24.74 g, 97 mmol) in 400 mL of acetonitrile was placed in a 1 L 3-neck round bottom flask equipped with a magnetic stirrer, thermocouple, N$_2$-filled balloon and heating mantle. An excess of t-butyl-2-bromo acetate (27.5 mL, 186 mmol) was added via syringe, and obtained mixture was stirred at 50° C. for 15 hrs.

The reaction was monitored by TLC (in CH$_2$Cl$_2$/MeOH=9/1), and after completion the potassium carbonate was removed by filtration, solvent was removed under reduced pressure to give product (100 g, 92% yield) as viscous yellow oil.

$^1$H NMR (400 MHz, CDCl$_3$, δ): 7.87 and 7.70 (m, 4H, aromatic, phthalimido), 7.15 and 6.86 (2d, 4H, aromatic, tyrosine), 7.78 (m, 5H, phenyl), 6.95 (d, 1H, HNCO), 5.02 (s, 2H, CH$_2$O), 4.80 (m, 1H, NCHCO), 4.43 (s, 2H, OCH$_2$CO), 3.90-3.50 (m, 18H, CH$_2$O, CH$_2$N), 3.12 (m, 2H, CH$_2$ in tyrosine), 2.35 (m, 2H, CH$_2$CO), 1.49 (s, 9H, t-Bu).

PhthN-dPEG$_4$(Tyr-OTBA)-OH

A mixture of Phth-dPEG4-(Tyr-OTBA)OBn ester (24 g, 31.5 mmol), activated charcoal (1.2 g, Darco) and palladium acetate (240 mg, 1.06 mmol) in 400 mL of degassed methanol was placed in a 1 L 3-neck round bottom flask equipped with a magnetic stirrer, thermocouple, H$_2$-inlet tube. Hydrogen was slowly bubbled through the mixture until the starting material was consumed (required about 5 hrs, the reaction was monitored by TLC in CH$_2$Cl$_2$/MeOH=9/1). After completion the reaction, the mixture was filtered over celite, washed with dichloromethane, and combined filtrates were concentrated on rotavap to give 22 g (~100% yield) of the product as viscous colorless oil.

$^1$H NMR (400 MHz, CDCl$_3$, δ): 7.83 and 7.71 (m, 4H, aromatic, phthalimido), 7.12 and 6.80 (2d, 4H, aromatic, tyrosine), 6.91 (d, 1H, HNCO), 4.78 (m, 1H, NCHCO), 4.47 (s, 2H, OCH$_2$CO), 3.90-3.45 (m, 18H, CH$_2$O, CH$_2$N), 3.10 (m, 2H, CH$_2$ in tyrosine), 2.49 (m, 2H, CH$_2$CO), 1.48 (s, 9H, t-Bu).

PhthN-dPEG$_4$(Tyr-OTBA)-NH-m-dPEG$_{12}$

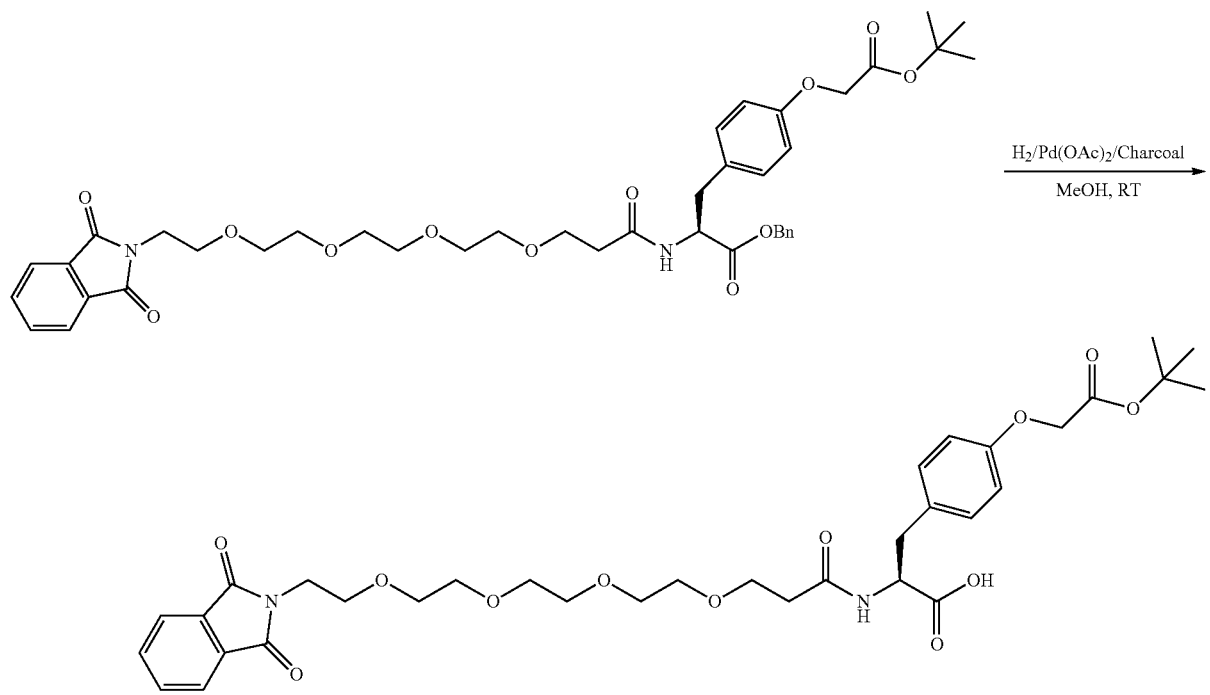

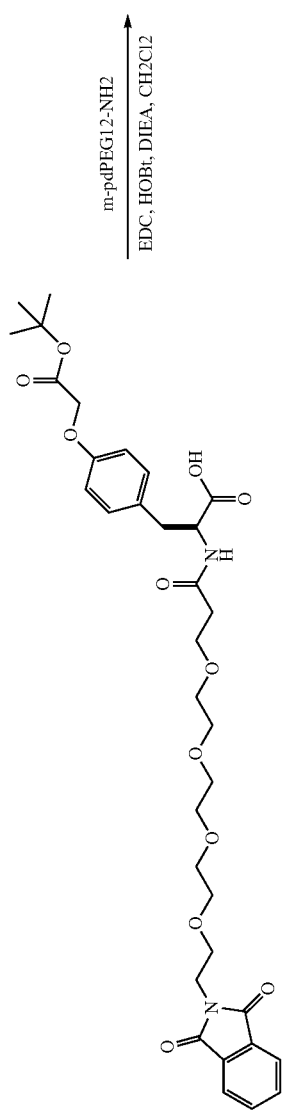

A mixture of m-dPEG12-NH$_2$ (11.59 g, 20.71 mmol), disopropylethyl amine (6.34 g, 49.1 mmol) and HOBt (0.74 g, 5.48 mmol) in 45 mL of anhydrous dichloromethane was charged in a 500 mL 3-neck round bottom flask equipped with a magnetic stirrer, thermocouple, N$_2$-filled balloon and cooling ice-methanol bath. Obtained solution was cooled to −7.6° C., and a solution of phthalimido-dPEG4-tyrosine (OTBE) acid (12.7 g, 18.88 mmol) in 20 mL in anhydrous dichloromethane was added via syringe at 0° C. in 5 min. Solid EDC (5.58 g, 29.1 mmol) was added at −2.5° C., cooling bath was removed and resulting mixture was allowed to warm up to ambient temperature and stirred overnight. The obtained mixture was quenched with cold 10% HCl (2×30 mL), organic bottom layer was separated and aqueous phase extracted with dichloromethane (2×80 mL). Combined extracts were washed with brine (1×80 mL) and dried over anhydrous Na$_2$SO$_4$, and concentrated under rediced pressure to give 22.54 g (98% yield) of clear viscous oil.

$^1$H NMR (400 MHz, CDCl$_3$, δ): 7.73 and 7.71 (m, 4H, aromatic, phthalimido), 7.12 and 6.80 (2d, 4H, aromatic, tyrosine), 6.91 (d, 1H, HNCO), 6.42 (m, 1H, HNCO), 4.58 (m, 1H, NCHCO), 4.47 (s, 2H, OCH$_2$CO), 3.90-3.50 (m, 66H, CH$_2$O, CH$_2$N), 3.38 (s, 3H, CH$_3$O), 3.00 (m, 2H, CH$_2$ in tyrosine), 2.43 (t, 2H, CH$_2$CO), 1.48 (s, 9H, t-Bu).

PhthN-dPEG$_4$(Tyr-OTBA)-m-dPEG$_4$

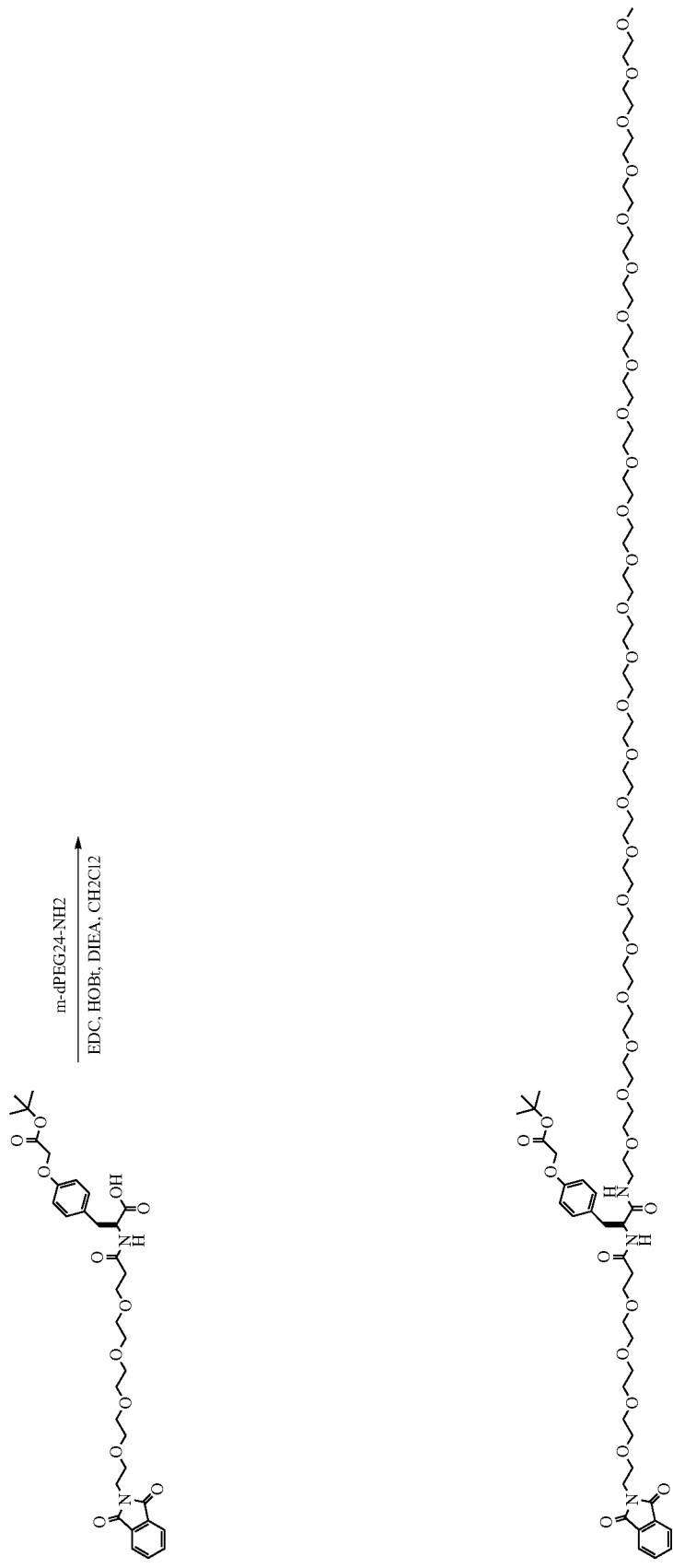

21.38 mmol) and HOBt (0.433 g, 3.21 mmol) in 40 mL of anhydrous dichloromethane was charged in a 100 mL 3-neck round bottom flask equipped with a magnetic stirrer, thermocouple, $N_2$-filled balloon and cooling ice-methanol bath. Obtained solution was cooled to −2.3° C., and a solution of phthalimido-dPEG4-tyrosine(OTBE) acid (7.19 g, 10.69 mmol) in 15 mL in anhydrous dichloromethane was added via syringe at 0° C. in 5 min. Solid EDC (2.56 g, 13.36 mmol) was added at −5° C., cooling bath was removed and resulting mixture was allowed to warm up to ambient temperature and stirred overnight. The obtained mixture was quenched with cold 10% HCl (2×30 mL), organic bottom layer was separated and aqueous phase extracted with dichloromethane (2×80 mL). Combined extracts were washed with brine (1×80 mL) and dried over anhydrous $Na_2SO_4$, and concentrated on rotavap to give 17 g (91% yield) of soft white solid.

$^1$H NMR (400 MHz, $CDCl_3$, δ): 7.73 and 7.71 (m, 4H, aromatic, phthalimido), 7.12 and 6.80 (2d, 4H, aromatic, tyrosine), 6.91 (d, 1H, HNCO), 6.42 (m, 1H, HNCO), 4.58 (m, 1H, NCHCO), 4.47 (s, 2H, $OCH_2CO$), 3.90-3.50 (m, 114H, $CH_2O$, $CH_2N$), 3.38 (s, 3H, $CH_3O$), 3.00 (m, 2H, $CH_2$ in tyrosine), 2.43 (t, 2H, $CH_2CO$), 1.48 (s, 9H, t-Bu).

PhthN-dPEG$_4$(Tyr-OAA)-NH-m-dPEG$_{12}$

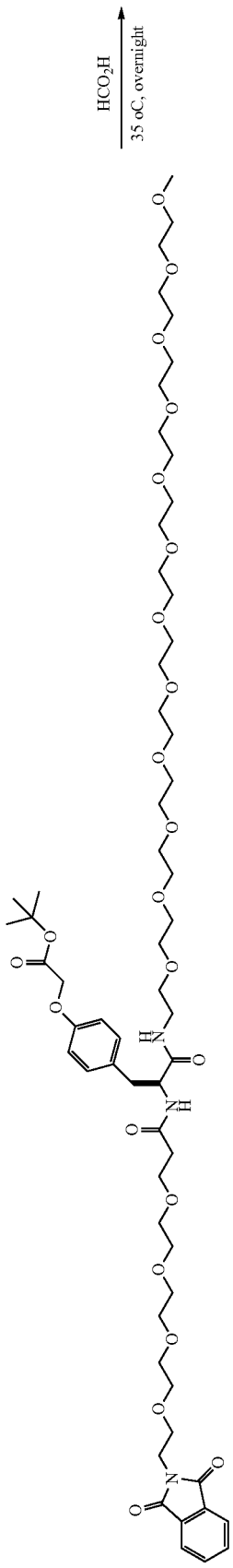
$\xrightarrow[35\ ^oC,\ \text{overnight}]{HCO_2H}$
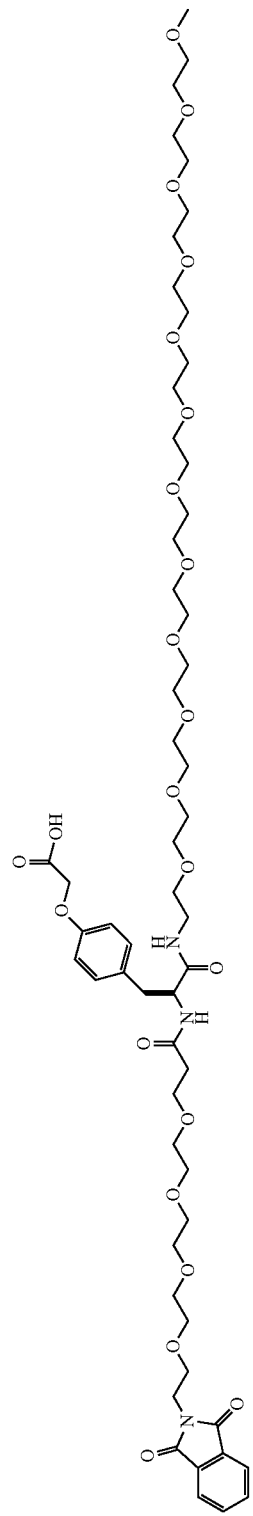

A mixture of PhthN-dPEG4-(Tyr-OTBE)-NH-m-dPEG12 (16.76 g, 13.80 mmol), and neat formic acid (31 g, 48.8 mmol) was charged in a 250 mL 3-neck round bottom flask equipped with a magnetic stirrer, thermocouple, $N_2$-filled balloon and heating mantle. The temperature of the obtained solution was maintained at 35° C., and the reaction stirred overnight. After the reaction was complete, an excess of formic acid was removed under reduced pressure, obtained oil was diluted with dichloromethane (150 mL), washed with water (2×40 mL) and brine (30 mL). Organic phase was dried over anhydrous $Na_2SO_4$ for 1 hr, filter over celite, concentrated and dried further on high vacuum pump to give 13.6 g (85% yield) of viscous yellow oil.

$^1$H NMR (400 MHz, $CDCl_3$, δ): 7.73 and 7.71 (m, 4H, aromatic, phthalimido), 7.12 and 6.80 (2d, 4H, aromatic, tyrosine), 6.91 (d, 1H, HNCO), 6.42 (m, 1H, HNCO), 4.58 (m, 1H, NCHCO), 4.47 (s, 2H, $OCH_2CO$), 3.90-3.50 (m, 66H, $CH_2O$), 3.38 (s, 3H, $CH_3O$), 3.00 (m, 2H, $CH_2$ in tyrosine), 2.43 (t, 2H, $CH_2CO$).

PhthN-dPEG$_4$(Tyr-OAA)-NH-m-dPEG$_{24}$

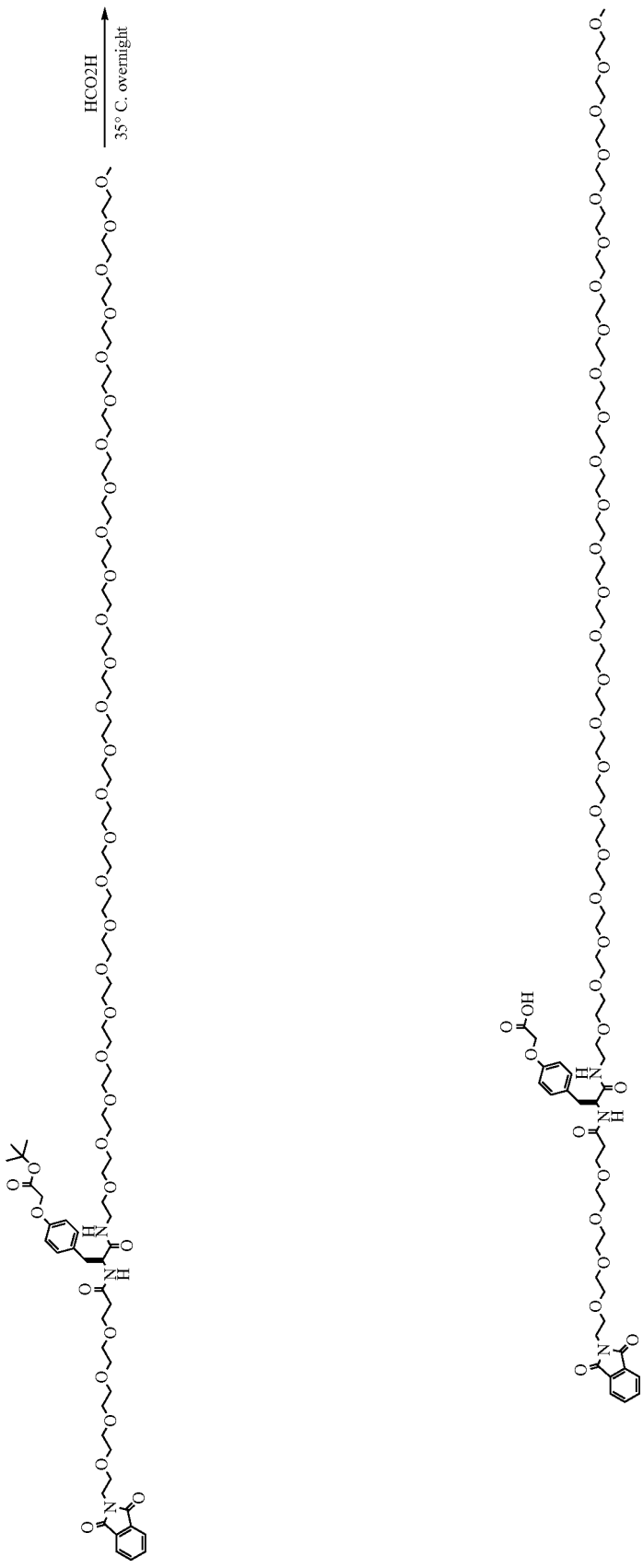

A mixture of PhthN-dPEG4-(Tyr-OTBE)-NH-m-dPEG24 (17 g, 9.75 mmol), and neat formic acid (31 g, 69.1 mmol) was charged in a 250 mL 3-neck round bottom flask equipped with a magnetic stirrer, thermocouple, $N_2$-filled balloon and heating mantle. The temperature of the obtained solution was maintained at 35° C., and the reaction stirred overnight. After the reaction was complete, an excess of formic acid was removed under reduced pressure, obtained oil was diluted with dichloromethane (180 mL), washed with water (2×50 mL) and brine (50 mL). Organic phase was dried over anhydrous $Na_2SO_4$ for 1 hr, filter over celite, concentrated and dried further on high vacuum pump to give 15.2 g (92% yield) of viscous yellow oil.

$^1$H NMR (400 MHz, $CDCl_3$, δ): 7.76 and 7.64 (m, 4H, aromatic, phthalimido), 7.05 and 6.76 (2d, 4H, aromatic, tyrosine), 6.97 (d, 1H, HNCO), 6.31 (m, 1H, HNCO), 4.51 (s, 2H, $OCH_2CO$), 4.50 (m, 1H, NCHCO), 3.82-3.35 (m, 114H, $CH_2O$), 3.32 (s, 3H, $CH_3O$), 2.90 (m, 2H, $CH_2$ in tyrosine), 2.38 (t, 2H, $CH_2CO$).

$H_2N$-$dPEG_4$(Tyr-OAA)-NH-m-$dPEG_{12}$

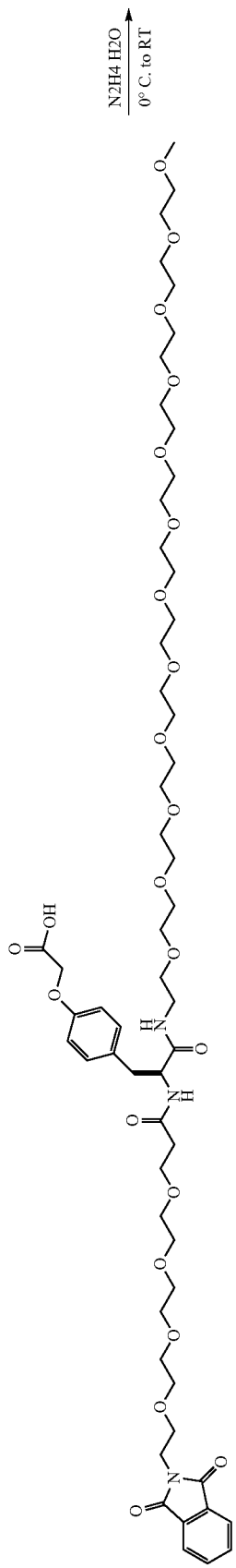

A solution of PhthN-dPEG4-(Tyr-OAA)-NH-m-dPEG12 (13 g, 11.22 mmol) in 25 mL of dichloromethane was placed in a 100 mL three-neck round bottom flask equipped with a magnetic stirrer, thermocouple, $N_2$-filled balloon and cooling ice bath. Hydrazine monohydrate (4.01 g, 80 mmol) was added drop wise via syringe at ~0° C., and obtained solution allowed to warm to ambient temperature overnight. Obtained white suspension was filtered over celite, washed with copious amount of dichloromethane (4×40 mL), clear filtrate was concentrated on rotavap following drying on high vacuum pump to give 10.6 g (92% yield) of very viscous yellow oil. According to TLC (in 90% DCM-10% MeOH) obtained crude material is quite clean, but contains some residual hydrazine (after visualization with ninhydrine). Therefore, this material was purify on silica gel (120 g biotage column) using gradient elution with $CH_2Cl_2$-MeOH from 100% $CH_2Cl_2$ to 85% $CH_2Cl_2$. Fractions were checked in 85% $CH_2Cl_2$-15% MeOH and pure were combined and concentrated to give 4.61 g (40% yield) of product as clear glassy material.

$^1$H NMR (400 MHz, $CDCl_3$, δ): 7.59 (d, 1H, HNCO), 7.30 (t, 1H, HNCO), 7.05 and 6.76 (2d, 4H, aromatic, tyrosine), 4.59 (m, 1H, NCHCO), 4.37 (s, 2H, $OCH_2CO$), 3.90-3.40 (m, 64H, $CH_2O$), 3.75 (s, 3H, $CH_3O$), 3.05-2.85 (m, 4H, $CH_2$ in tyrosine, and $C\underline{H}_2NH_2$), 2.42 (m, 2H, $CH_2CO$).

$H_2N$-dPEG$_4$(Tyr-OAA)-NH-m-dPEG$_{24}$

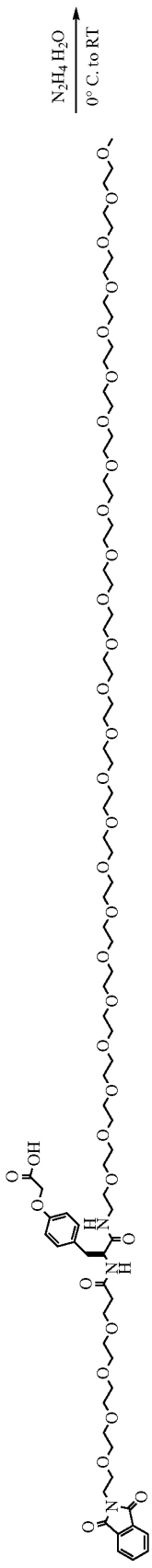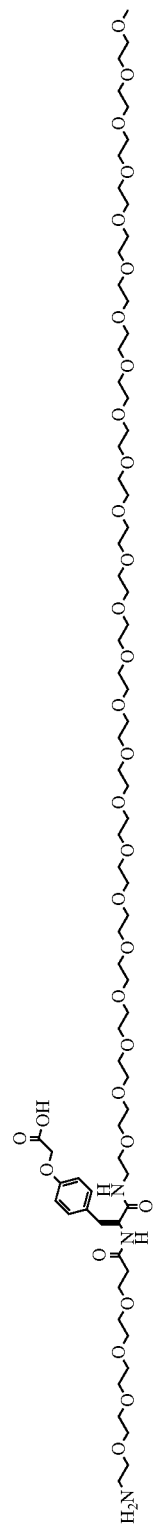

A solution of PhthN-dPEG4-(Tyr-OAA)-NH-m-dPEG24 (15 g, 8.89 mmol) in 35 mL of dichloromethane was placed in a 100 mL three-neck round bottom flask equipped with a magnetic stirrer, thermocouple, $N_2$-filled balloon and cooling ice bath. Hydrazine monohydrate (3.61 g, 72.1 mmol) was added drop wise via syringe at ~0° C., and obtained solution allowed to warm to ambient temperature overnight. Obtained white suspension was filtered over celite, washed with copious amount of dichloromethane (5×80 mL), clear filtrate was concentrated on rotavap following drying on high vacuum pump to give 19 g (92% yield) of clear viscous oil. This crude was triturated with 400 mL of methyl-t-butyl ether to give white suspension. The product filtered via a sintered glass funnel, washed with methyl-t-butyl ether (2×120 mL), dried under N2/suction following drying on high vacuum pump to give 13.1 g (95% yield) of white solid.

According to TLC (in 90% DCM-10% MeOH) obtained crude material is quite clean, but still contains some residual hydrazine (after visualization with ninhydrine). Therefore, this material was purify on silica gel (220 g biotage column) using gradient elution with $CH_2Cl_2$-MeOH from 100% $CH_2Cl_2$ to 80% $CH_2Cl_2$. Fractions were checked in 90% $CH_2Cl_2$-10% MeOH and pure were combined and concentrated to give 6.92 g (50% yield) of product as clear oil which slowly crystallizes into white solid.

$^1$H NMR (400 MHz, $CDCl_3$, δ): 7.53 (d, 1H, HNCO), 7.25 (m, 1H, HNCO), 7.05 and 6.76 (2d, 4H, aromatic, tyrosine), 4.60 (m, 1H, NCHCO), 4.40 (s, 2H, $OCH_2CO$), 3.90-3.40 (m, 112H, $CH_2O$), 3.40 (s, 3H, $CH_3O$), 3.02-2.80 (m, 4H, $CH_2$ in tyrosine, and $CH_2NH_2$), 2.42 (m, 2H, $CH_2CO$).

MAL-dPEG$_4$(Tyr-OAA)-NH-m-dPEG$_{12}$

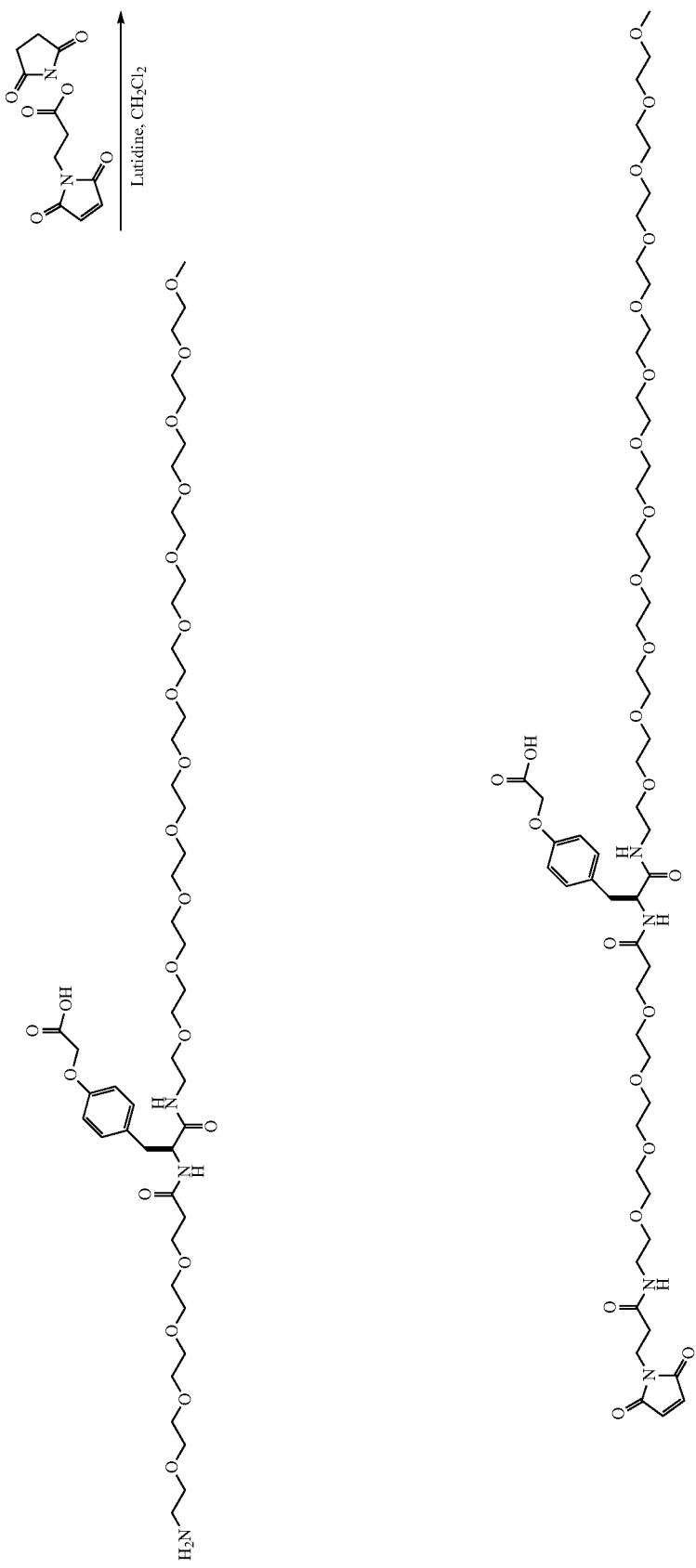

A suspension of NHS-ester of maleimidopropionic acid (MPS, 1.41 g, 5.3 mmol) in 20 mL of anhydrous dichloromethane was charged into a 100 mL three-neck round bottom flask equipped with a magnetic stirrer, $N_2$-filled balloon, cooling ice bath and thermocouple. In a separate 100 mL one-neck round bottom flask a solution of amino-dPEG4-(Tyr-OAA)-NH-m-dPEG12 (4.38 g, 4.26 mmol) and lutidine (1.24 g, 11.57 mmol) was prepared in 15 mL of anhydrous $CH_2Cl_2$. This solution was added drop wise via syringe to the suspension of MPS/$CH_2Cl_2$ at ~0° C. and the reaction was allowed to warm to ambient temperature overnight. The reaction was monitored by TLC (in CH2Cl2-MeOH=9/1) and after completion was diluted with DCM (100 mL) and washed with cold 5% HCl (2×20 mL) and brine (1×20 mL). Organic phase was separated, aqueous was extracted with $CH_2Cl_2$ (3×30 mL) and combined extracts were dried over anhydrous $Na_2SO_4$ for 1 hour at stirring. Drying agent was removed and clear filtrate was concentrated under reduced pressure to give 6.5 g of cloudy viscous oil. Obtained crude was purified on silica gel (120 g biotage column) using gradient elution with $CH_2Cl_2$-MeOH from 100% $CH_2Cl_2$ to 85% $CH_2Cl_2$. Fractions were checked by TLC in 90% $CH_2Cl_2$-10% MeOH, pure were combined and concentrated to give 3 g of colorless viscous oil. The purified material contains some residual NHS by NMR, and which has very close $R_f$-value with the product. Therefore, in order to remove NHS, the product was precipitated on celite using methyl-t-butyl ether. In order to do that, it was dissolved in 15 mL of ethyl acetate obtained solution was placed in a 0.5 L three-neck round bottom flask equipped with a magnetic stirrer and addition funnel, and clear solution was slowly diluted with t-BuOCH$_3$ until cloudiness was achieved. Celite (6 g) was added and drop wise addition of t-BuOCH$_3$ was resumed (a total 150 mL of t-BuOCH$_3$ was added). Obtained suspension was filtered, washed with t-BuOCH$_3$ (2×50 mL), and filtrate was discarded. The product was removed from celite with $CH_2Cl_2$ (5×40 mL). Obtained clear filtrate was concentrated under reduced pressure, dried on high vacuum pump for 3 hours to give 3.18 g (63% yield) of product as viscous yellow oil.

$^1$H NMR (400 MHz, CDCl$_3$, δ): 7.13 and 6.83 (2d, 4H, aromatic, tyrosine), 7.04 (d, 1H, HNCO), 6.70 (s, 2H, CH=CH), 6.68 (m, 1H, HNCO), 6.52 (m, 1H, HNCO), 4.61 (s, 2H, OCH$_2$CO), 4.58 (m, 1H, NCHCO), 3.90-3.40 (m, 64H, CH$_2$O), 3.83 (t, 2H, CH$_2$N), 3.38 (s, 3H, CH$_3$O), 3.00 (m, 2H, CH$_2$ in tyrosine), 2.53 (t, 2H, CH$_2$CO), 2.46 (t, 2H, CH$_2$CO).

MAL-dPEG$_4$(Tyr-OAA)-m-dPEG$_4$

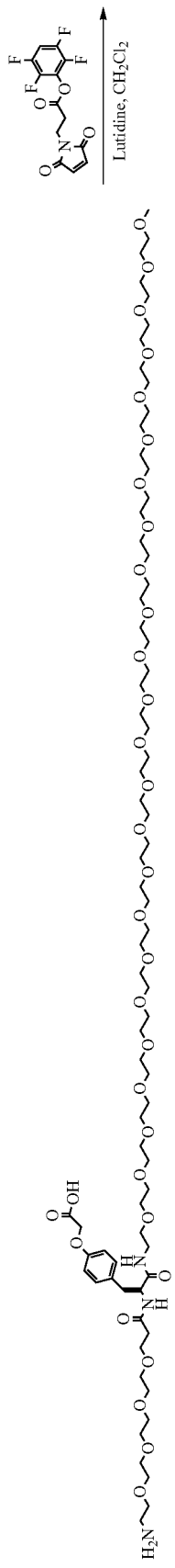

A solution of TFP-ester of maleimidopropionic acid (MPS-TFP, 2.38 g, 7.50 mmol) in 20 mL of anhydrous dichloromethane was charged into a 100 mL three-neck round bottom flask equipped with a magnetic stirrer, $N_2$-filled balloon, cooling ice bath and thermocouple. In a separate 100 mL one-neck round bottom flask a solution of amino-dPEG4-(Tyr-OAA)-NH-m-dPEG24 (8.4 g, 5.4 mmol) and lutidine (1.79 g, 16.71 mmol) was prepared in 20 mL of anhydrous $CH_2Cl_2$. This solution was added drop wise via syringe to the suspension of MPS-TFP/$CH_2Cl_2$ at ~0° C. and the reaction was allowed to warm to ambient temperature overnight. The reaction was monitored by TLC (in CH2Cl2-MeOH=9/1). After completion the reaction was diluted with DCM (100 mL) and washed with cold 5% HCl (2×20 mL) and brine (1×20 mL). Organic phase was separated, aqueous was extracted with $CH_2Cl_2$ (3×30 mL) and combined extracts were dried over anhydrous $Na_2SO_4$ for 1 hour at stirring. Drying agent was removed and clear filtrate was concentrated under reduced pressure to give 12 g of crude as viscous oil. This crude was purified on silica gel (120 g biotage column) using gradient elution with $CH_2Cl_2$-MeOH from 100% $CH_2Cl_2$ to 85% $CH_2Cl_2$. Fractions were checked by TLC in 90% $CH_2Cl_2$-10% MeOH, pure were combined and concentrated to give 6.75 g of product as colorless viscous oil which slowly solidifies into white solid.

$^1$H NMR (400 MHz, $CDCl_3$, δ): 7.05 and 6.76 (2d, 4H, aromatic, tyrosine), 6.90 (broad d, 1H, HNCO), 6.66 (m, 1H, HNCO), 6.63 (s, 2H, C=C), 6.49 (m, 1H NHCO), 4.53 (s, 2H, $OCH_2CO$), 4.51 (m, 1H, NCHCO), 3.75 (t, 2H, CH2N), 3.70-3.35 (m, 112H, $CH_2O$), 3.31 (s, 3H, $CH_3O$), 2.92 (m, 2H, CH2 in tyrosine), 2.48 (t, 2H, $CH_2CO$), 2.38 (t, 2H, $CH_2CO$).

MAL-dPEG$_4$(Tyr-TFP ester)-NH-m-dPEG$_{12}$

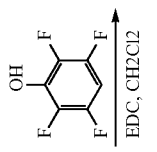 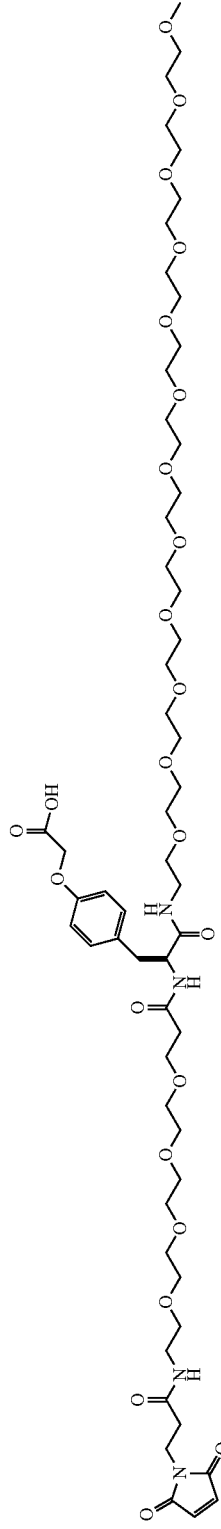 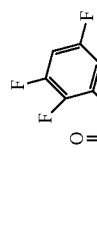 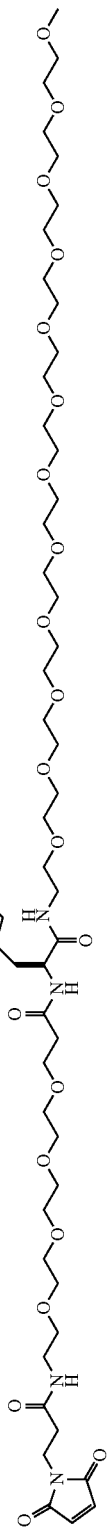

A mixture of Mal-dPEG4-(Tyr-OAA)-NH-mdPEG12 (3.04 g, 2.58 mmol) and tetrafluorophenol (TFP, 0.889 g, 5.83 mmol) was placed into a 250 mL 4-neckround bottom flask equipped with a thermocouple, magnetic stirrer, N2-filled balloon and cooling ice-water bath. Anhydrous dichloromethane (25 mL) was added, obtained solution was cooled to ~0° C., and solid EDC (0.863 g, 4.5 mmol) was added to the reaction in one portion. Reaction was allowed to warm up to ambient temperature under stirring overnight. The reaction was monitored by TLC (in $CH_2Cl_2$-MeOH=9/1) and after completion was diluted with DCM (80 mL) and quenched with cold water (1×50 mL). Organic phase was separated, aqueous layer extracted with $CH_2Cl_2$ (2×30 mL) and combined organic phases were washed with brine (1×50 mL) and died over anhydrous $Na_2SO_4$. Drying agent was removed by filtration over celite, and clear filtrate was concentrated under reduced pressure to give 4.48 g of viscous "tan" oil. This crude was purified by chromatography on silica gel (80 g biotage column) using gradient elution with $CH_2Cl_2$-EtOAc from 100% to 50% $CH_2Cl_2$ to remove an excess of TFP; after that the gradient was switched to $CH_2Cl_2$-IPA from 100% to 75% $CH_2Cl_2$. Pure fractions were combined and concentrated under reduced pressure at ambient temperature and kept under high vacuum for 2 days in order to remove residual isopropanol. Obtained 1.77 g (52% yield) of product as viscous oil.

$^1$H NMR (400 MHz, $CDCl_3$, δ): 7.20 and 6.90 (2d, 4H, aromatic, tyrosine), 7.08 (m, 1H, in TFP), 7.03 (d, 1H, HNCO), 6.70 (s, 2H, CH=CH), 6.53 (m, 2H, HNCO), 5.00 (s, 2H, $OCH_2CO$), 4.60 (m, 1H, NCHCO), 3.83 (t, 2H, CH2N), 3.80-3.40 (m, 64H, $CH_2O$), 3.38 (s, 3H, $CH_3O$), 3.05 (m, 2H, $CH_2$ in tyrosine), 2.52 (t, 2H, $CH_2CO$), 2.47 (m, 2H, $CH_2CO$).

MAL-dPEG$_4$(Tyr-TFP ester)-NH-m-dPEG$_{24}$

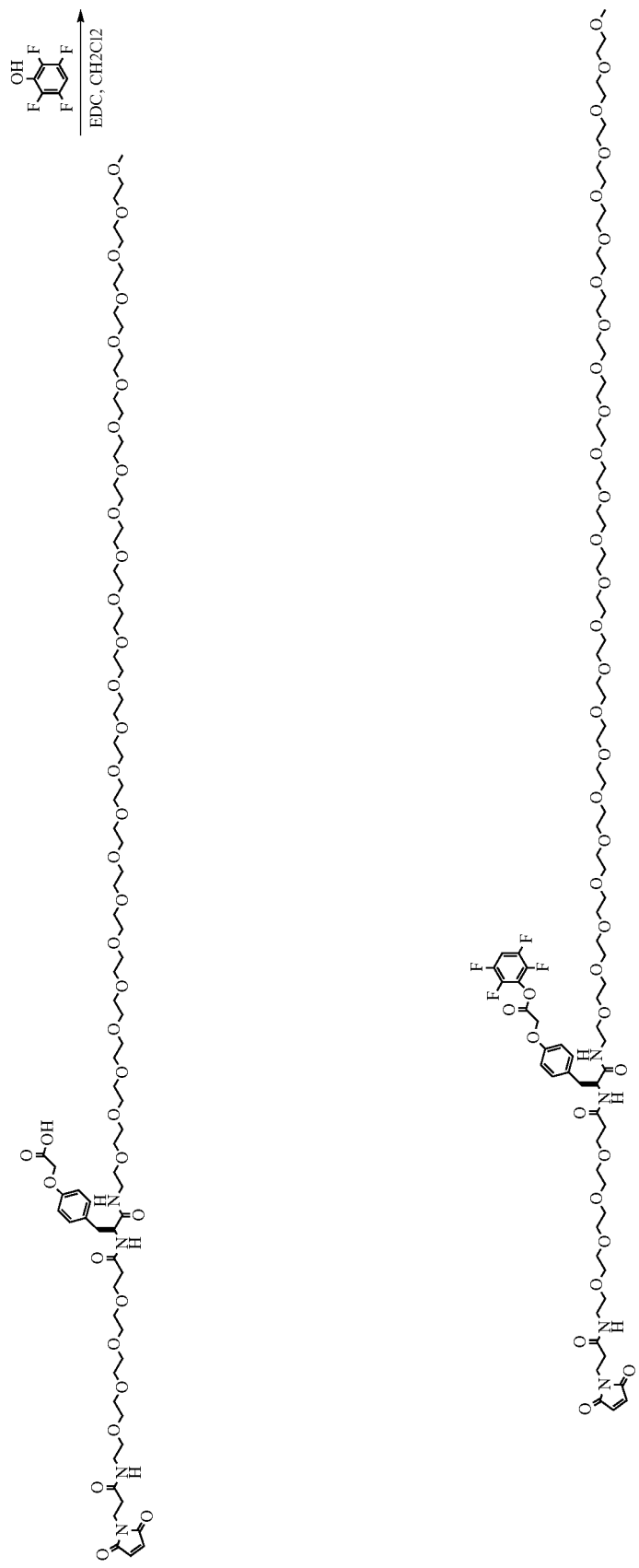

A mixture of Mal-dPEG4-(Tyr-OAA)-NH-mdPEG24 (3.60 g, 2.108 mmol) and tetrafluorophenol (TFP, 0.85 g, 5.12 mmol) was placed into a 250 mL 4-neckround bottom flask equipped with a thermocouple, magnetic stirrer, N2-filled balloon and cooling ice-water bath. Anhydrous dichloromethane (25 mL) was added, obtained solution was cooled to ~0° C., and solid EDC (0.747 g, 3.90 mmol) was added to the reaction in one portion. Reaction was allowed to warm up to ambient temperature under stirring overnight. The reaction was monitored by TLC (in $CH_2Cl_2$-MeOH=9/1) and after completion was diluted with DCM (100 mL) and quenched with cold water (60 mL). Organic phase was separated, aqueous layer extracted with $CH_2Cl_2$ (2×30 mL) and combined organic phases were washed with brine (60 mL) and died over anhydrous $Na_2SO_4$. Drying agent was removed by filtration over celite, and clear filtrate was concentrated under reduced pressure to give 5.32 of viscous oil. This crude was purified by chromatography on silica gel (80 g biotage column) using gradient elution with $CH_2Cl_2$-EtOAc from 100% to 50% $CH_2Cl_2$ to remove an excess of TFP; after that the gradient was switched to $CH_2Cl_2$-IPA from 100% to 75% $CH_2Cl_2$. Pure fractions were combined and concentrated under reduced pressure at ambient temperature and kept under high vacuum for 2 days in order to remove residual isopropanol. Obtained 3.32 g (85% yield) of product as viscous oil which slowly solidifies into white solid.

$^1$H NMR (400 MHz, $CDCl_3$, δ): 7.20 and 6.90 (2d, 4H, aromatic, tyrosine), 7.07 (m, 1H, in TFP), 7.03 (m, 1H, HNCO), 6.71 (s, 2H, CH=CH), 6.55 (broad m, 2H, HNCO), 5.01 (s, 2H, $OCH_2CO$), 4.61 (dd, 1H, NCHCO), 3.85 (t, 2H, $CH_2N$), 3.80-3.40 (m, 112H, $CH_2O$), 3.39 (s, 3H, $CH_3O$), 3.05 (m, 2H, $CH_2$ in tyrosine), 2.57 (t, 2H, $CH_2CO$), 2.48 (m, 2H, $CH_2CO$).

7-(4-m-dPEG$_4$)-piperazidyl)-CIPRO; 7-(4-(2,5,8,11-tetraoxatetradecan-14-oyl)piperazin-1-yl)-1-cyclopropyl-6-fluoro-4-oxo-1,4-dihydroquinoline-3-carboxylic acid Ciprofloxacin (2.135 g, 6.44 mmol) was charged in a 100 mL 3-neck round bottom flask equipped with a magnetic stirrer, thermocouple, cooling ice/water bath and $N_2$-filled balloon. Anhydrous dichloromethane (25 mL) was added to the flask following by addition of lutidine (1.39 g, 12.97 mmol) and the reaction cooled on an ice bath. A solution of m-dPEG$_4$-NHS (2.21 g, 6.63 mmol) in 6 mL of anhydrous $CH_2Cl_2$ was added at 10° C. to the reaction, cooling bath was removed and reaction stirred overnight. The reaction was monitored by TLC ($CH_2Cl_2$/MeOH=9/1), and after completion it was quenched with cold 5% HCl (10 mL) and brine (15 mL). The organic phase (bottom) was separated, aqueous extracted with $CH_2Cl_2$ (1×50 mL) and combined organic phases were washed with brine (1×30 mL), dried over anhydrous $Na_2SO_4$ under stirring for 30 min, filtered over celite bed (5 g) and concentrated under reduced pressure to give 5.54 g of white solid. Methyl-t-butyl ether (MTBE, 120 mL) was added to the solid, and obtained suspension was filtered via sintered glass filter funnel, washed with MTBE (3×25 mL) and dried under $N_2$-flow for 30 min to give 3.48 g of fluffy white solid. It was re-dissolved in dichloromethane and purified on silica gel (80 g biotage column) using gradient elution with $CH_2Cl_2$-MeOH from 100% to 95% $CH_2Cl_2$. Pure fractions were combined and concentrated on under reduced pressure to give white solid which was dried further on high vacuum pump for 3 hrs to give 3.18 g (90% yield) of product as white solid.

$^1$H NMR (400 MHz, DMSO-d6, δ): 8.64 (s, 1H, NCH=C), 7.89 (d, 1H, aromatic), 7.55 (d, 1H, aromatic), 3.81 (m, 1H, NCH in cyclopropyl), 3.75-3.40 (m, 18H, 14CH$_2$O, and 4H in piperazine), 3.40-3.25 (two m, 4H in piperazine), 3.22 (s, 3H, $CH_3$), 2.65 (t, 2H, $CH_2CO$), 1.33 and 1.19 (two m, 4H, cyclopropyl).

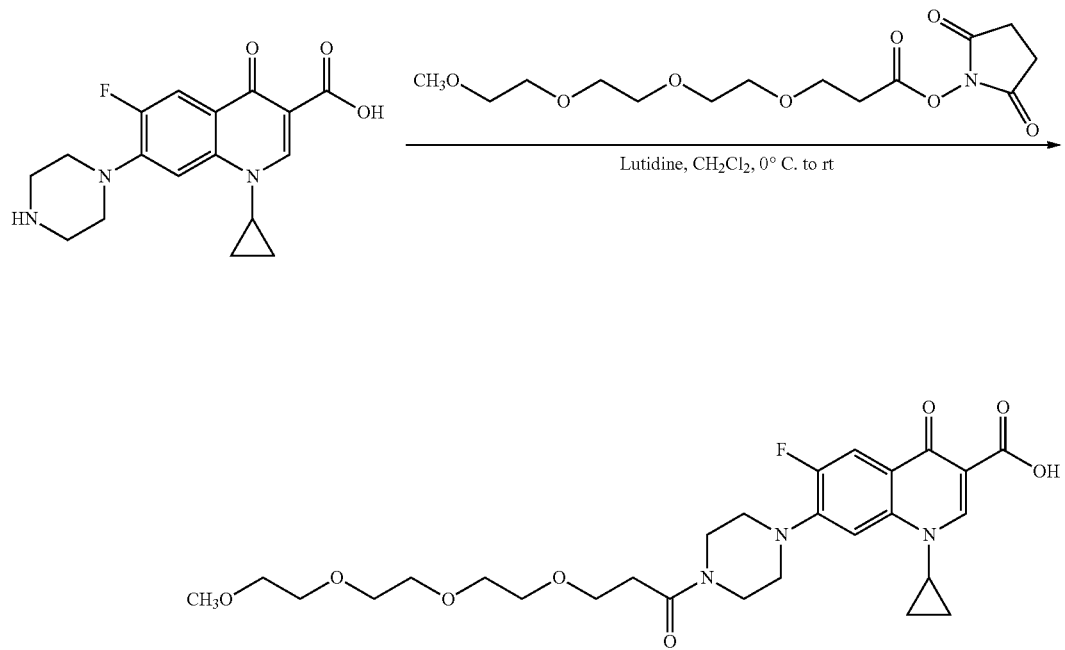

7-(4-(m-dPEG12)-piperazidyl)-CIPRO; 7-(4-(2,5,8,11,14,17,20,23,26,29,32,35-dodecaoxaoctatriacontan-38-oyl)piperazin-1-yl)-1-cyclopropyl-6-fluoro-4-oxo-1,4-dihydroquinoline-3-carboxylic acid

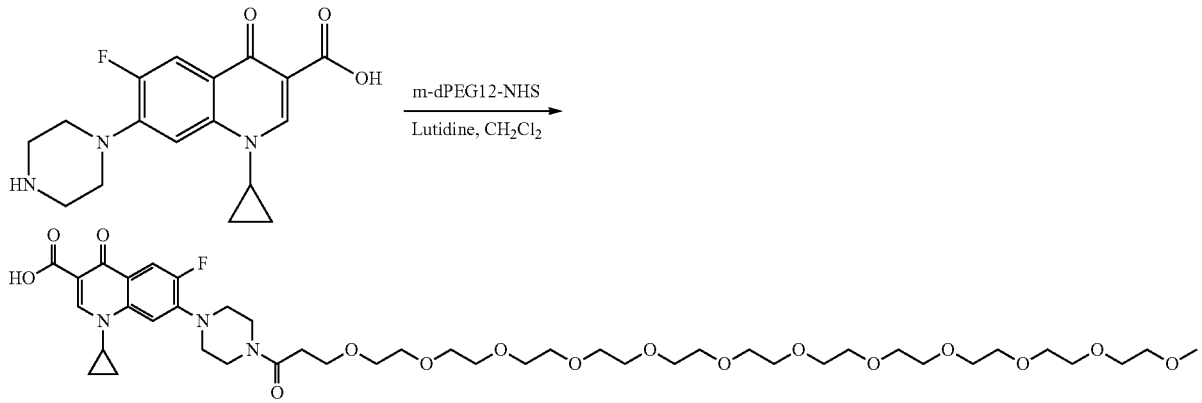

Ciprofloxacin (3.465 g, 10.46 mmol) was charged in a 250 mL 3-neck round bottom flask equipped with a magnetic stirrer, thermocouple, cooling ice/water bath and $N_2$-filled balloon. Anhydrous $CH_2Cl_2$ (40 mL) was added to the flask following by addition of lutidine (2.289 g, 21.36 mmol) and the reaction cooled on an ice bath. A solution of m-dPEG$_{12}$-NHS (7.98 g, 11.64 mmol) in 15 mL of anhydrous $CH_2Cl_2$ was added at 0° C. to the reaction, cooling bath was removed and reaction stirred overnight. The reaction was monitored by TLC ($CH_2Cl_2$/MeOH=9/1), and after completion it was quenched with cold 5% HCl (20 mL) and brine (20 mL). The organic phase (bottom) was separated, aqueous extracted with $CH_2Cl_2$ (3×50 mL) and combined organic phases were washed with brine (1×30 mL), dried over anhydrous $Na_2SO_4$ under stirring for 30 min, filtered over celite bed and concentrated under reduced pressure to give 12 g solid. This crude was purified on silica gel (120 g biotage column) using gradient elution with $CH_2Cl_2$-MeOH from 100% to 90% $CH_2Cl_2$. Pure fractions were combined and concentrated on under reduced pressure to give 8 g of white waxy. This material was triturated with methyl-t-butyl ether (100 mL), obtained white powder dried on a high vacuum pump for 4 hrs to give 6.74 g (71.5% yield) of the product as white sticky solid.

$^1$H NMR (400 MHz, DMSO-d6, δ): 8.66 (s, 1H, NCH=C), 7.90 (d, 1H, aromatic), 7.57 (d, 1H, aromatic), 3.82 (m, 1H, NCH in cyclopropyl), 3.75-3.65 (m, 6H, $CH_2O$, and in piperazine), 3.60-3.25 (m, 48H, $CH_2O$ and in piperazine), 3.24 (s, 3H, $CH_3O$), 2.65 (t, 2H, $CH_2CO$), 1.33 and 1.20 (two m, 4H, cyclopropyl).

m-dPEG$_4$-CIPRO (ester); 2,5,8,11-tetraoxatridecan-13-yl 1-cyclopropyl-6-fluoro-4-oxo-7-(piperazin-1-yl)-1,4-dihydroquinoline-3-carboxylate

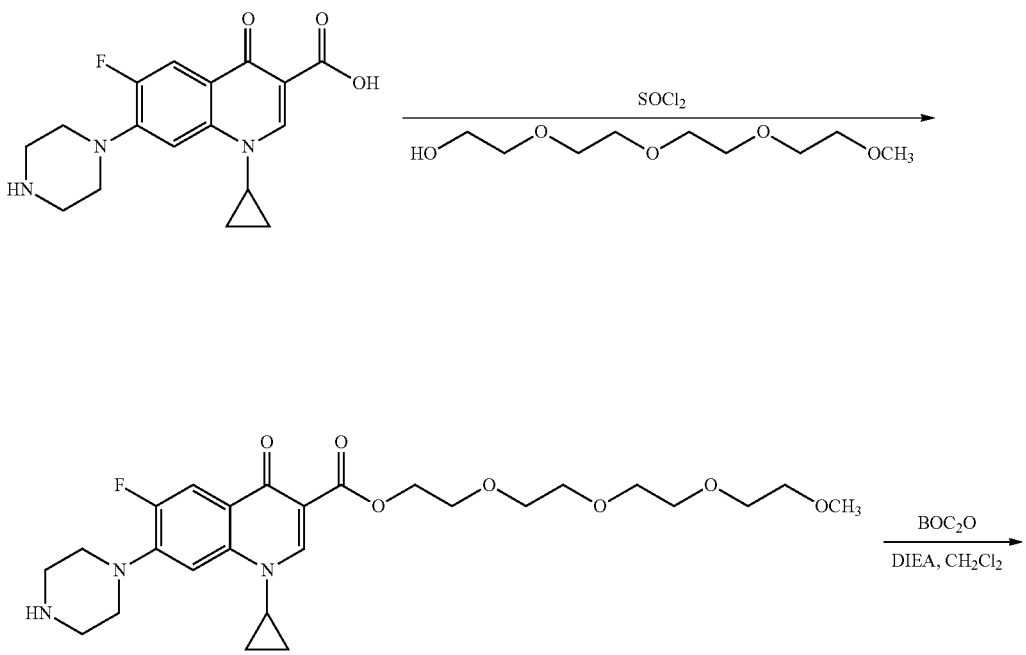

-continued

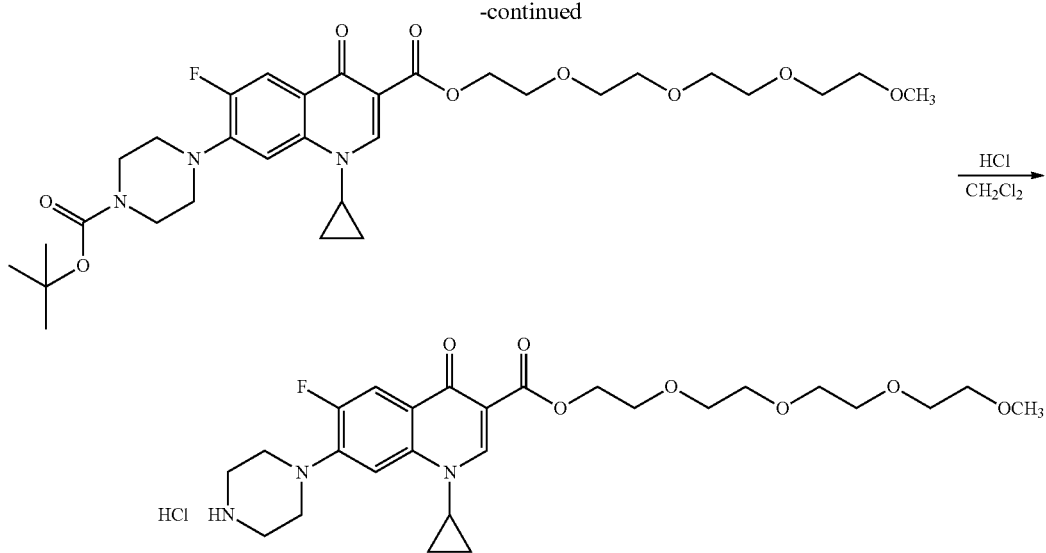

Neat thionyl chloride (7.93 g, 66.7 mmol) was placed in a 50 mL one-neck RBF equipped with a magnetic stirrer and $N_2$-filled balloon, and cooled on ice bath to ~0° C. Ciprofloxacin (2.15 g, 6.49 mmol) was added portion wise resulting in immediate thick orange-colored sticky suspension formation. Ice bath was removed and this suspension stirred for 2 hours at ambient temperature. After this period of time, the suspension was diluted with 12 mL of anhydrous $CH_2Cl_2$ and concentrated to dryness in order to remove an excess of thionyl chloride. It was repeated 2 times, and anhydrous $CH_2Cl_2$ (40 mL) was added to obtained orange-red material which is not soluble with dichloromethane. The reaction was cooled on ice bath, and neat m-dPEG$_4$-OH (4.64 g, 22.28 mmol) was added. Obtained suspension stirred at ambient temperature until all solids gradually dissolved and clear deep yellow solution was obtained. The reaction concentrated under reduced pressure and the residue was kept on high vacuum pump for 4 hours in order to remove all residual hydrogen chloride.

Obtained oil was re-dissolved in 30 mL of anhydrous $CH_2Cl_2$, and placed in 3-neck round bottom flask equipped with a magnetic stirrer, $N_2$-filled balloon, thermocouple and cooling ice-water bath. The reaction cooled to 2° C., and a solution of BOC-anhydride (2.75 g, 12.6 mmol) in 12 mL of anhydrous dichloromethane was added via syringe. Neat triethylamine (2.03 g, 20.06 mmol) was added drop wise via syringe at this temperature, and after completion of addition cooling bath was removed and resulting dark yellow suspension stirred at ambient temperature for 3 hours. The reaction mixture was diluted with $CH_2Cl_2$ (50 mL), and quenched with cold water (2×50 mL) containing brine (10 mL). Dark yellow phase was separated and dried over anhydrous $Na_2SO_4$ under stirring for 1 hr, filtered and concentrated under reduced pressure to give 8.5 g of brownish oil. This crude was purified on silica gel (120 g biotage column) using gradient elution with $CH_2Cl_2$-EtOH from 100% to 90% CH2Cl2. Fractions were checked by TLC in 90% $CH_2Cl_2$-10% MeOH and pure gfractions were concentrated to give after drying on high vacuum pump 1 g (25% yield) off-white/pale yellow.

$^1$H NMR (400 MHz, CDCl$_3$, δ): 8.48 (s, 1H, NCH═C), 7.98 (d, 1H, aromatic), 7.24 (d, 1H, aromatic), 4.45 (t, 2H, CH2O), 3.84 (t, 2H, CH2O), 3.75-3.50 (m, 20H, CH2O, and CH2N in piperazine), 3.42 (m, 1H, NCH in cyclopropyl), 3.38 (s, 3H, CH3O), 3.21 (m, 4H in piperazine), 1.50 (s, 9H, t-Bu), 1.31 and 1.13 (two m, 4H in cyclopropyl).

A solution of boc-cipro-m-dPEG$_4$ ester (1 g, 1.609 mmol) in anhydrous $CH_2Cl_2$ (10 mL) was placed in a 100 mL 3-neck round bottom flask equipped with a magnetic stirrer, cooling ice/water bath, thermocouple and $N_2$-filled balloon. A solution of HCl in diethyl ether (5 mL of 2M solution) was added drop wise at 0° C., cooling bath was removed and the reaction stirred at ambient temperature overnight. Obtained clear yellow solution was concentrated on under reduced pressure, oily residue was dissolved in $CH_2Cl_2$ (8 mL), and methyl-t-butyl ether (50 mL) was added drop wise to this solution resulting in precipitation of bulky yellowish material. Obtained suspension was stirred for 30 min and filtered over sintered glass filter under $N_2$ blanket. Isolated product dried further on high vacuum pump for 8 hours to give 0.7 g (78% yield) of yellow solid.

$^1$H NMR (400 MHz, CDCl$_3$, δ): 10.4 (broad s, 2H, $NH_2$—HCl), 8.79 (s, 1H, NCH═C), 7.94 (d, 1H, aromatic), 7.66 (broad s, 1H, aromatic), 4.52 (t, 2H, $CH_2O$), 4.05 (broad s, 1H), 3.95-3.80 (m, 6H, $CH_2O$, $CH_2N$ in piperazine), 3.75-3.50 (m, 10H, CH2O), 3.55-3.40 (m, 6H, in piperazine), 3.35 (s, 3H, $CH_3O$), 1.55 and 1.20 (two m, 4H in cyclopropyl).

m-dPEG$_{23}$-CIPRO (ester); 2,5,8,11,14,17,20,23,26,29,32,35,38,41,44,47,50,53,56,59,62,65,68-tricosaoxaheptacontan-70-yl 1-cyclopropyl-6-fluoro-4-oxo-7-(piperazin-1-yl)-1,2,3,4-tetrahydroquinoline-3-carboxylate

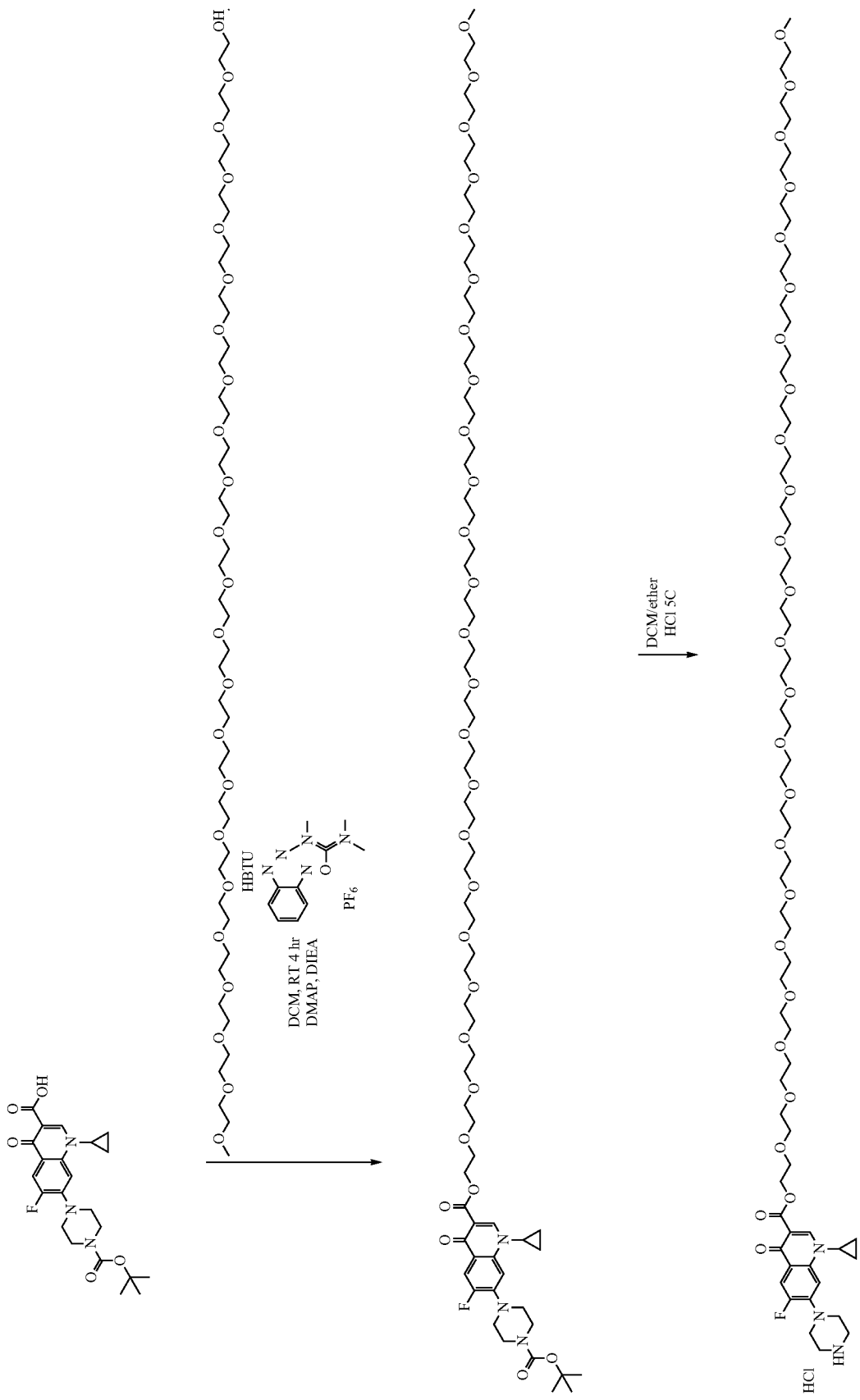

The Boc-Cipro (1.5 g, 3.48 mmol) was weighed into a 100 mL 1-neck round bottom flask charged with a stir bar and thermo probe. The flask anhydrous $CH_2Cl_2$ (30 mL) was added to create a suspension. The DMAP (85 mg, 0.7 mmol) was added followed immediately by HBTU (3.3 g, 8.7 mmol). The suspension was let stir for 2.5 hours. To the suspension m-dPEG$_{23}$-OH (10.9 g, 10.4 mmol) and DIEA (2.25 g, 17.4 mmol) dissolved in $CH_2Cl_2$ (15 mL) and added via syringe. The reaction was stirred at RT for 1 hour and progress checked by TLC ($CH_2Cl_2$/MeOH=9/1). TLC showed minimal starting material remaining and the formation of a more polar product (blue under UV). The reaction TLC showed completion after 4 hours. The reaction was diluted with $CH_2Cl_2$ (40 mL) and washed with 10% aq. Sodium bicarbonate (1×40 mL), water (1–30 mL), brine (lx 30 mL). The organic layer was dried over magnesium sulphate for 1 hour, filtered and then concentrated under reduced pressure to yield 11 g of dark yellow oil. The oil was dissolved in $CH_2Cl_2$ (10 mL) and washed with MTBE (50 mL) to give an off white waxy solid. The MTBE was decanted and the solid was washed a second time with MTBE (50 mL). 8.1 g of the crude solid was absorbed on 17 g silica gel and purified on the Rf using a 120 g column $CH_2Cl_2$/EtOH. 0% EtOH for 2CV, up to 5% EtOH over 5CV, 5% for 3CV, up to 10% EtOH over 3CV. pure fractions were combined and concentrated under reduced pressure. Yield: 1.6 g, 31.6% viscous yellow oil.

$^1$H NMR (400 MHz, CDCl$_3$, δ): 8.65 (s, 1H, NCH), 7.86, (d, 1H, FCCH), 7.38 (d, 1H, CH), 4.48 (t, 2H, $CH_2O$), 3.77 (t, 2H, $CH_2O$), 3.67 (t, 2H, $CH_2O$), 3.69 (t, 4H, $CH_2N$), 3.56 (m, 91H, $CH_2O$, $CH_2N$, CHN), 3.29 (s, 3H, $CH_3$), 3.21 (t, 4H, $CH_2N$), 1.45 (s, 9H, $CH_3$), 1.33 and 1.09 (m, 4H, $CH_2CH$)

A 100 mL 1-neck round bottom flask was charged with stir bar, thermo probe, and Boc-CIPRO-m-dPEG$_{23}$ ester (1.4 g, 0.96 mmol) in $CH_2Cl_2$ (5 mL) which stirred until the oil went into solution. This solution was added drop wise via syringe to a 100 mL 1-neck round bottom flask containing HCl (4 mL, 8.0 mmol) in ether in an ice/water bath at 5° C. Once addition was complete the ice/water bath was removed and reaction was allowed to warm to room temperature and stir for 15 hours. The reaction was checked via TLC ($CH_2Cl_2$/MeOH=9/1) and showed the reaction was complete. The solution was concentrated under reduced pressure and then MTBE (50 mL) was added and stirred for 15 minutes. The product precipitated out of solution and was filtered over a nylon membrane filter. The resultant solid was collected into a round bottom flask and dried under reduced pressure. Yield: 0.936 g, 70% off-white solid.

$^1$H NMR (400 MHz, DMSO-d6, δ): 8.88 (s, 2H, $NH_2$), 8.47 (s, 1H, NCH), 7.82, (d, 1H, FCCH), 7.49 (d, 1H, CH), 4.29 (t, 2H, $CH_2O$) 3.71 (t, 2H, $CH_2O$) 3.69 (m, 1H, CHN), 3.50 (m, 90H, $CH_2O$, $CH_2N$), 3.34 (t, 4H, $CH_2N$), 3.24 (s, 3H, CH3O) 1.29 and 1.10 (m, 4H, $CH_2CH$)

I claim:

1. A substantially pure construct represented by:

where,
(a) AC is an amino acid attachment core;
(b) the linear hydrocarbon chains (~~~) contains a discrete PEG residue of between about 4 and 64 ethylene oxide residues;
(c) A is a chemically reactable group or a chemically reactive group;
(d) the terminal linear discrete PEG-containing chain (——) has between about 8 and 72 ethylene oxide residues and having a terminal non-reactive moiety; and
(e) n ranges between 1 and 10;
where A is biorthogonal;
where A biorthogonal.

2. The substantially pure compound of claim 1, wherein A is a cell surface and matrix antigen, transport protein, receptor protein, an antibody, antibody fragment, cytokine, aptamer, siRNA, vitamin, steroid, a nanoparticle, or microparticle.

3. The substantially pure compound of claim 1, wherein the wavy line, ~~~, contains between about 4 and 48 ethylene oxide groups.

4. The substantially pure compound of claim 1, wherein each solid line, ——, independently, contains between about 8 and 36 ethylene oxide groups.

5. The substantially pure compound of claim 4, wherein the wavy line, ~~~, attached to AC contains, between about 4 and 48 ethylene oxide groups.

6. The substantially pure compound of claim 1, where the non-reactive terminal moiety of the terminal linear discrete PEG-containing chain (——) is a methoxy group.

7. The substantially pure compound of claim 1, where the non-reactive terminal moiety of the terminal linear discrete PEG-containing chain (——) is a charged group.

8. A substantially pure construct represented by:

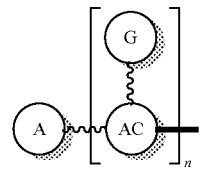

where,
(a) AC is an amino acid attachment core;
(b) the linear hydrocarbon chains (~~~) contain a discrete PEG residue of between about 4 and 64 ethylene oxide residues;
(c) G is a masked chemically reactive moiety;
(d) A is a chemically reactable group or a chemically reactive group;
(e) the terminal linear discrete PEG-containing chain (——)has between about 8 and 72 ethylene oxide residues and having a terminal non-reactive moiety; and
(f) n ranges between 1 and 10;
where A is biorthogonal; and
where A and G are independently reactive or reactable.

9. The substantially pure compound of claim 8, wherein G is one or more of:
(a) a diagnostic group, being one or more of radiolabels, chromogenic and fluorescent dyes, a biotin, and combinations thereof; or
(b) a therapeutic group being one or more of radionuclides, toxic drugs, cytokines, enzymes, antibiotic, and combinations thereof.

10. The substantially pure compound of claim 8, wherein A is a cell surface and matrix antigen, transport protein, receptor protein, an antibody, antibody fragment, peptide, peptide substrate, cytokine, aptamer, siRNA, vitamin, steroid, a nanoparticle, or microparticle.

11. The substantially pure compound of claim 8, wherein G is one or more of:
  (a) a diagnostic group, being one or more of radiolabels, chromogenic and fluorescent dyes, a biotin, and combinations thereof; or
  (b) a therapeutic group being one or more of radionuclides, toxic drugs, cytokines, enzymes, antibiotic, and combinations thereof.

12. A substantially pure construct represented by:

where,
  (a) AC is an amino acid attachment core;
  (b) the linear hydrocarbon chains ( ~~~ ) contains a discrete PEG residue of between about 4 and 64 ethylene oxide residues;
  (c) A is a biologically active group;
  (d) the terminal linear discrete PEG-containing chain (——)has between about 8 and 72 ethylene oxide residues and having a terminal non-reactive moiety; and
  (e) n ranges between 1 and 10;
where A is biorthogonal.

13. A substantially pure construct represented by:

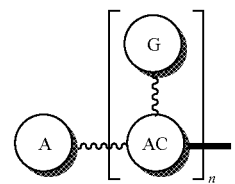

where,
  (a) AC is an amino acid attachment core;
  (b) the linear hydrocarbon chains ( ~~~ ) contains a discrete PEG residue of between about 4 and 64 ethylene oxide residues;
  (c) G is a biologically active group;
  (d) A is a chemically reactable group or a chemically reactive group;
  (e) the terminal linear discrete PEG-containing chain ( ——)has between about 8 and 72 ethylene oxide residues and having a terminal non-reactive moiety; and
  (f) n ranges between 1 and 10;
where A biorthogonal; and
where A and G are independently reactive or reactable.

* * * * *